United States Patent
Souers et al.

(10) Patent No.: US 7,049,307 B2
(45) Date of Patent: May 23, 2006

(54) ANTAGONISTS OF MELANIN CONCENTRATING HORMONE EFFECTS ON THE MELANIN CONCENTRATING HORMONE RECEPTOR

(75) Inventors: Andrew J. Souers, Evanston, IL (US); Christine A. Collins, Skokie, IL (US); Ju Gao, Gurnee, IL (US); Andrew S. Judd, Grayslake, IL (US); Philip R. Kym, Libertyville, IL (US); Mathew M. Mulhern, Hainesville, IL (US); Hing L. Sham, Vernon Hills, IL (US); Dariusz Wodka, Plainsboro, NJ (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 11/020,464

(22) Filed: Dec. 22, 2004

(65) Prior Publication Data

US 2005/0187279 A1   Aug. 25, 2005

Related U.S. Application Data

(60) Provisional application No. 60/532,112, filed on Dec. 23, 2003.

(51) Int. Cl.
*A61K 31/55* (2006.01)
*A61K 31/416* (2006.01)
*A61K 31/5377* (2006.01)
*A61K 31/438* (2006.01)
*A61K 31/454* (2006.01)

(52) U.S. Cl. .............. 514/210.21; 514/234.5; 514/278; 514/322; 514/403; 514/217.09; 540/603; 544/119; 546/19; 546/199; 548/360.1

(58) Field of Classification Search ............. 540/603; 544/119; 546/19, 199; 548/360.1
See application file for complete search history.

(56) References Cited

U.S. PATENT DOCUMENTS

2002/0052373 A1   5/2002   Zorn et al. ............. 514/248

FOREIGN PATENT DOCUMENTS

WO    98/30548    7/1998
WO    03/015769   2/2003

OTHER PUBLICATIONS

Zhao et al. (Zhurnal Obshchei Khimii 1959, 29, pp. 1012-1020) CAS Abstract Attached.*
Nahon, J-L, "The Melanin-Concentrating Hormone: From the Peptide to the Gene",*Critical Rev in Neurobiology*, 8(4):221-262 (1994).

* cited by examiner

*Primary Examiner*—Kamal A. Saeed
*Assistant Examiner*—Jason M. Nolan
(74) *Attorney, Agent, or Firm*—Johanna M. Corbin

(57) ABSTRACT

The present invention relates to the antagonism of the effects of melanin-concentrating hormone (MCH) through the melanin concentrating hormone receptor which is useful for the prevention or treatment of eating disorders, weight gain, obesity, abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders.

19 Claims, No Drawings

ANTAGONISTS OF MELANIN CONCENTRATING HORMONE EFFECTS ON THE MELANIN CONCENTRATING HORMONE RECEPTOR

This application claims priority to U.S. Provisional Patent Application Ser. No. 60/532,112, filed Dec. 23, 2003, which is incorporated herein by reference.

TECHNICAL FIELD

The present invention relates to the antagonism of the effects of melanin-concentrating hormone (MCH) through the melanin concentrating hormone receptor which is useful for the prevention or treatment of eating disorders, weight gain, obesity, abnormalities in reproduction and sexual behavior, thyroid hormone secretion, diuresis and water/electrolyte homeostasis, sensory processing, memory, sleeping, arousal, anxiety, depression, seizures, neurodegeneration and psychiatric disorders.

BACKGROUND OF THE INVENTION

Obesity is a major cause and contributor to health problems such as type II diabetes, coronary heart disease, increased incidence of certain forms of cancer and respiratory complications. It is a disease that is increasing at an alarming rate due to increased availability of high-fat diets, genetic susceptibility and a more sedentary way of life in modern society. Obesity can be defined as weight gain resulting from a mismatch of energy intake and energy expenditure. Food intake and energy metabolism are regulated, in part, by the interaction of neuropeptides and their receptors. Recently, the role that the hormone leptin plays in controlling appetite has been elucidated.

Leptin is a peptide hormone produced by fat cells, regulating both food intake and and metabolism by acting on leptin receptors in the hypothalamus. Increased fat stores leads to increased secretion of leptin, resulting in a signal to the hypothalamus to decrease food intake, whereas decreases in adiposity result in lower leptin levels and a stimulation of food intake. Melanin-concentrating hormone (MCH) has been identified as an orexigenic peptide that counterbalances the activity of leptin.

MCH is a cyclic 19 amino acid neuropeptide expressed in the zona incerta and lateral hypothalamus in response to both energy restriction and leptin deficiency. MCH is known to stimulate feeding when injected into the lateral ventricle of rats and the mRNA for MCH is upregulated in the hypothalamus of genetically obese mice (ob/ob) and in fasted control and ob/ob animals. Mice lacking MCH are hypophagic and lean with increased metabolic rate, whereas animals over-expressing MCH gain excess weight on both standard and high fat diets. MCH is thought to have effects on other nervous system functions as well (Nahon J L., The melanin-concentrating hormone: from the peptide to the gene. Crit Rev Neurobiol 8:221–262, 1994). An orphan G-protein coupled receptor (GPCR) was recently identified as a receptor for MCH.

Although there exists current pharmacologic therapies used to treat obesity, none of the current therapies achieve the U.S. Food and Drug Administration criteria for benefit measured by a 5% difference in mean weight loss, as weight loss efficacy is diminished by reduction of patient adherence to pharmacological therapy due to side effects of the drugs. Some of the side effects associated with current therapies include increased heart rate and blood pressure and uncontrolled excretion of fat in stools. Thus, there exists a medical need for agents capable of preventing or treating eating disorders, weight gain and obesity, that at the same time, have improved efficacy and safety.

SUMMARY OF THE INVENTION

The present invention is directed to compounds of formula (I),

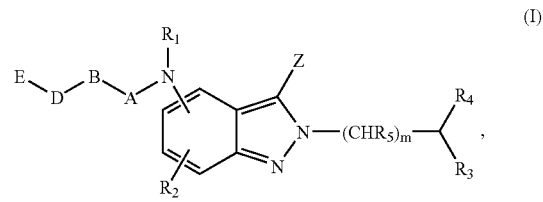

or a therapeutically acceptable salt or prodrug thereof, wherein

A is selected from the group consisting of —C(O)—, —S(O)—, —S(O)$_2$—, —C(=NR$_a$)— and —C(=S)—;

B is a bond or is selected from the group consisting of alkylene, alkenyl, carbonylalkyl, cycloalkyl, —NR$_b$— and —NR$_b$-alkyl;

D is a bond or is selected from the group consisting of alkylene, aryl, arylalkyl, heterocycle and heterocyclealkyl;

E is selected from the group consisting of alkyl, alkyl-C(O)—, alkyl-C(O)—NH—, alkyl-NH—, alkyl-NH—C(O)—, alkyl-NH—S(O)$_2$—, alkoxy, alkyl-S—, alkyl-S(O)$_2$—, alkyl-S(O)$_2$—NH—, aryl, aryl-C(O)—, aryl-C(O)—NH—, aryl-C=N—O—, aryl-NH—, aryl-NH—C(O)—, aryl-NH—S(O)$_2$—, aryloxy, aryl-S—, aryl-S-alkyl-C(O)—, aryl-S(O)$_2$—, aryl-S(O)$_2$—NH—, arylalkyl-C(O)—, arylalkyl-C(O)—NH—, arylalkyl-NH—, arylalkyl-NH—C(O)—, arylalkyl-NH—S(O)$_2$—, arylalkoxy, arylalkyl-S—, arylalkyl-S(O)$_2$—, arylalkyl-S(O)$_2$—NH—, cycloalkyl, cycloalkyl-C(O)—, cycloalkyl-C(O)—NH—, cycloalkyl-NH—, cycloalkyl-NH—C(O)—, cycloalkyl-NH—S(O)$_2$—, cycloalkoxy, cycloalkyl-S—, cycloalkyl-S(O)$_2$—, cycloalkyl-S(O)$_2$—NH—, cycloalkenyl, cycloalkenylalkyl, cycloalkenyl-C(O)—, cycloalkenyl-C(O)—NH—, cycloalkenyl-NH—, cycloalkenyl-NH—C(O)—, cycloalkenyl-NH—S(O)$_2$—, cycloalkenyloxy, cycloalkenyl-S—, cycloalkenyl-S(O)$_2$—, cycloalkenyl-S(O)—NH—, heterocycle, heterocycle-C(O)—, heterocycle-C(O)—NH—, heterocycle-NH—, heterocycle-NH—C(O)—, heterocycle-NH—S(O)$_2$—, heterocycle-O—, heterocycle-S—, heterocycle-S(O)$_2$—, heterocycle-S(O)$_2$—NH—, heterocycle-alkyl-C(O)—, heterocycle-alkyl-C(O)—NH—, heterocycle-alkyl-NH—, heterocycle-alkyl-NH—C(O)—, heterocycle-alkyl-NH—S(O)$_2$—, heterocycle-alkyl-O—, heterocycle-alkyl-S—, heterocycle-alkyl-S(O)$_2$— and heterocycle-alkyl-S(O)$_2$—NH—;

R$_1$ is selected from the group consisting of hydrogen and alkyl;

R$_2$ is selected from the group consisting of hydrogen, halogen, alkyl and alkoxy;

R$_3$ is R$_c$R$_d$N—;

R$_4$ is selected from the group consisting of hydrogen and alkyl, or R$_4$ and R$_c$ taken together with any intervening atoms form a heterocycle;

each occurrence of R$_5$ is independently selected from the group consisting of hydrogen and alkyl;

$R_a$ is selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ are each independently selected from the group consisting of hydrogen, alkyl, aryl, arylalkyl, cycloalkyl, cycloalkenylalkyl, heterocycle, heterocycle-alkyl and hydroxyalkyl, or $R_c$ and $R_d$ taken together with the atoms to which they are attached form a heterocycle;

Z is selected from the group consisting of hydrogen, alkyl and halogen; and m is 1, 2 or 3;

provided that:

if B is $NR_b$—, $NR_b$-alkyl or —O—, then

D is selected from the group consisting of alkyl, aryl, arylalkyl, heterocycle and heterocyclealkyl.

Another embodiment of the present invention encompasses the use of the compounds of the present invention for the treatment of obesity comprising administration of said compounds to a patient in need of such treatment.

A further embodiment of the present invention encompasses the use of the compounds of the present invention for the treatment of disorders that are mediated by MCH through the MCH receptor such as abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders comprising administering a therapeutically effective amount of a compound of formula (I) to a patient in need thereof.

According to another embodiment, the present invention is directed to a pharmaceutical composition comprising a therapeutically effective amount of a compound of formula (I) in combination with a pharmaceutically suitable carrier.

DETAILED DESCRIPTION OF THE INVENTION

The principal embodiment of the present invention is directed toward compounds of formula (I) and their use in the treatment of disorders mediated by MCH comprising administration of a therapeutically effective amount of a compound of formula (I) in need of such treatment.

Accordingly, the principle embodiment of the present invention is directed toward a compound of formula (I),

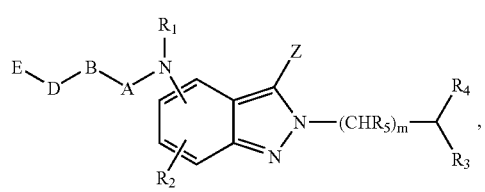

or a therapeutically acceptable salt or prodrug thereof, wherein A is selected from the group consisting of —C(O)—, —S(O)—, —S(O)$_2$—, —C(=NR$_a$)— and —C(=S)—; B is a bond or is selected from the group consisting of alkylene, alkenyl, carbonylalkyl, cycloalkyl, —NR$_b$— and —NR$_b$-alkyl; D is a bond or is selected from the group consisting of alkylene, aryl, arylalkyl, heterocycle and heterocyclealkyl; E is selected from the group consisting of alkyl, alkyl-C(O)—, alkyl-C(O)—NH—, alkyl-NH—, alkyl-NH—C(O)—, alkyl-NH—S(O)$_2$—, alkoxy, alkyl-S—, alkyl-S(O)$_2$—, alkyl-S(O)$_2$—NH—, aryl, aryl-C(O)—, aryl-C(O)—NH—, aryl-C=N—O—, aryl-NH—, aryl-NH—C(O)—, aryl-NH—S(O)$_2$—, aryloxy, aryl-S—, aryl-S-alkyl-C(O)—, aryl-S(O)$_2$—, aryl-S(O)$_2$—NH—, arylalkyl-C(O)—, arylalkyl-C(O)—NH—, arylalkyl-NH—, arylalkyl-NH—C(O)—, arylalkyl-NH—S(O)$_2$—, arylalkoxy, arylalkyl-S—, arylalkyl-S(O)$_2$—, arylalkyl-S(O)$_2$—NH—, cycloalkyl, cycloalkyl-C(O)—, cycloalkyl-C(O)—NH—, cycloalkyl-NH—, cycloalkyl-NH—C(O)—, cycloalkyl-NH—S(O)$_2$—, cycloalkoxy, cycloalkyl-S—, cycloalkyl-S(O)$_2$—, cycloalkyl-S(O)$_2$—NH—, cycloalkenyl, cycloalkenylalkyl, cycloalkenyl-C(O)—, cycloalkenyl-C(O)—NH—, cycloalkenyl-NH—, cycloalkenyl-NH—C(O)—, cycloalkenyl-NH—S(O)$_2$—, cycloalkenyloxy, cycloalkenyl-S—, cycloalkenyl-S(O)$_2$—, cycloalkenyl-S(O)$_2$—NH—, heterocycle, heterocycle-C(O)—, heterocycle-C(O)—NH—, heterocycle-NH—, heterocycle-NH—C(O)—, heterocycle-NH—S(O)$_2$—, heterocycle-O—, heterocycle-S—, heterocycle-S(O)$_2$—, heterocycle-S(O)$_2$—NH—, heterocycle-alkyl-C(O)—, heterocycle-alkyl-C(O)—NH—, heterocycle-alkyl-NH—, heterocycle-alkyl-NH—C(O)—, heterocycle-alkyl-NH—S(O)$_2$—, heterocycle-alkyl-O—, heterocycle-alkyl-S—, heterocycle-alkyl-S(O)$_2$— and heterocycle-alkyl-S(O)$_2$—NH—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocycle-alkyl and hydroxyalkyl, or $R_c$ and $R_d$ taken together with the atoms to which they are attached form a heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, alkyl-S(O)$_2$—, aryl-C(O)—, aryl-C=N—O—, aryl-NH—, aryloxy, aryl-S—, aryl-S-alkyl-C(O)—, aryl-S(O)$_2$—, arylalkyl-C(O)—, arylalkyl-NH—, arylalkoxy, arylalkyl-S(O)$_2$—, cycloalkyl, cycloalkyl-C(O)—, cycloalkyl-NH—, cycloalkoxy, cycloalkyl-S(O)$_2$—, cycloalkenylalkyl, heterocycle-C(O)—, heterocycle-NH—, heterocycle-O—, heterocycle-S(O)$_2$—, heterocycle-alkyl-C(O)—, heterocycle-alkyl-NH—, heterocycle-alkyl-O— and heterocycle-alkyl-S(O)$_2$—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocycle-alkyl and hydroxyalkyl or $R_c$ and $R_d$ taken together with the atoms to which they are attached form a heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocycle-alkyl and hydroxyalkyl or $R_c$ and $R_d$ taken together with the atoms to which they are attached form a heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl, aryl, arylalkyl, cycloalkyl, cycloalkenylalkyl, heterocycle, heterocycle-alkyl and hydroxyalkyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ are each independently selected from the group consisting of hydrogen, alkyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 4 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 5 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a pyrrolidine; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form an oxazolidinyl; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 2,3-dihydro-1H-indole; Z is selected from the group consisting of hydrogen, alkyl and halogen; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; R$_1$ is selected from the group consisting of hydrogen and alkyl; R$_2$ is selected from the group consisting of hydrogen, halogen, alkyl, alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ taken together with the atoms to which they are attached form Y is selected from the group consisting of —O—, —NRj-, —CHRj- and —C(O)—; Z is selected from the group consisting of hydrogen, alkyl and halogen; R$_8$ is selected from the group consisting of hydrogen and alkyl; and R$_9$ and R$_{10}$ are each individually selected from the group consisting of oxo, hydrogen and alkyl; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; R$_1$ is selected from the group consisting of hydrogen and alkyl; R$_2$ is selected from the group consisting of hydrogen, halogen, alkyl, alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ taken together with the atoms to which they are attached form a 6 membered heterocycle; Z is selected from the group consisting of hydrogen, alkyl and halogen; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; R$_1$ is selected from the group consisting of hydrogen and alkyl; R$_2$ is selected from the group consisting of hydrogen, halogen, alkyl, alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ taken together with the atoms to which they are attached form a morpholine ring; Z is selected from the group consisting of hydrogen, alkyl and halogen; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; R$_1$ is selected from the group consisting of hydrogen and alkyl; R$_2$ is selected from the group consisting of hydrogen, halogen, alkyl, alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ taken together with the atoms to which they are attached form a piperidine ring; Z is selected from the group consisting of hydrogen, alkyl and halogen; and m is 1, 2 or 3; provided that: if B is NR$_b$— or NR$_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —NR$_b$— and —NR$_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a piperazine ring; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form

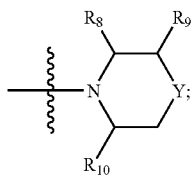

Y is selected from the group consisting of —O—, —NRj-, —CHRj- and —C(O)—; Z is selected from the group consisting of hydrogen, alkyl and halogen; $R_8$ is selected from the group consisting of hydrogen and alkyl; $R_9$ and $R_{10}$ are each individually selected from the group consisting of oxo, hydrogen and alkyl; and m is 1, 2 or 3; provided that:

if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form a 7 membered heterocycle; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; $R_1$ is selected from the group consisting of hydrogen and alkyl; $R_2$ is selected from the group consisting of hydrogen, halogen, alkyl, alkoxy; $R_3$ is $R_cR_dN$—; $R_4$ is selected from the group consisting of hydrogen and alkyl, or $R_4$ and $R_c$ taken together with any intervening atoms form a heterocycle; each occurrence of $R_5$ is independently selected from the group consisting of hydrogen and alkyl; $R_a$ is selected from the group consisting of hydrogen and alkyl; $R_b$ is selected from the group consisting of hydrogen and alkyl, or $R_b$ and $R_1$ taken together with any intervening atoms form a heterocycle; $R_c$ and $R_d$ taken together with the atoms to which they are attached form an azepan ring; Z is selected from the group consisting of hydrogen, alkyl and halogen; and m is 1, 2 or 3; provided that: if B is $NR_b$— or $NR_b$-alkyl, then D is selected from the group consisting of alkyl, aryl, arylalkyl, heterocycle and heterocyclealkyl.

Another embodiment of the present invention is directed toward a compound of formula (I), wherein A is —C(O)—; B is a bond or is selected from the group consisting of alkylene, alkenyl, —$NR_b$— and —$NR_b$alkyl; D is a bond or is selected from the group consisting of alkylene, aryl, arylalkyl, heterocycle and heterocyclealkyl; E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—; R$_1$ is selected from the group consisting of hydrogen and alkyl; R$_2$ is selected from the group consisting of hydrogen, halogen, alkyl, alkoxy; R$_3$ is R$_c$R$_d$N—; R$_4$ is selected from the group consisting of hydrogen and alkyl, or R$_4$ and R$_c$ taken together with any intervening atoms form a heterocycle; each occurrence of R$_5$ is independently selected from the group consisting of hydrogen and alkyl; R$_a$ is selected from the group consisting of hydrogen and alkyl; R$_b$ is selected from the group consisting of hydrogen and alkyl, or R$_b$ and R$_1$ taken together with any intervening atoms form a heterocycle; R$_c$ and R$_d$ taken together with the atoms to which they are attached form

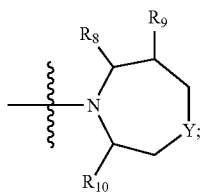

Y is selected from the group consisting of —O—, —NRj-, —CHRj- and —C(O)—; Z is selected from the group consisting of hydrogen, alkyl and halogen; R$_8$ is selected from the group consisting of hydrogen and alkyl; and R$_9$ and R$_{10}$ are each individually selected from the group consisting of oxo, hydrogen and alkyl; and m is 1, 2 or 3; provided that: if B is NR$_b$— or NR$_b$-alkyl, then D is selected from the group consisting of alkyl, aryl, arylalkyl, heterocycle and heterocyclealkyl.

The compounds of the present invention mediate the action of MCH through the MCH receptor, therefore, the compounds of the present invention are useful in treating disorders that are mediated by MCH. In the principal embodiment of the present invention there is provided a method of treating disorders mediated by MCH through the MCH receptor comprising administration of a therapeutically effective amount of a compound of formula (I). Disorders that are mediated by MCH through the MCH receptor are obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Therefore the compounds of the present invention are useful in treating obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders.

According to another embodiment of the present invention, there is provided a method of treating disorders by inhibiting the effects of melanin concentrating hormone (MCH) through the melanin concentrating hormone receptor, comprising administering a therapeutically effective amount of a compound of formula (I).

According to another embodiment of the present invention, there is provided a method of treating obesity by inhibiting the effects of melanin concentrating hormone (MCH) through the melanin concentrating hormone receptor, comprising administering a therapeutically effective amount of a compound of formula (I).

According to another embodiment of the present invention, there is provided a method of treating abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders by inhibiting the effects of melanin concentrating hormone (MCH) through the melanin concentrating hormone receptor, comprising administering a therapeutically effective amount of a compound of formula (I).

According to another embodiment of the present invention, there is provided a pharmaceutical composition comprising a therapeutically effective amount of a compound of formula (I) in combination with a pharmaceutically suitable carrier.

Definitions

As used throughout this specification and the appended claims, the following terms have the following meanings:

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy and hexyloxy.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl and 1-oxopentyl.

The term "alkyl-C(O)—," as used herein, refers to an alkyl group, as defined herein, appended to the parent molecular moiety through a C(O)— group, as defined herein.

The term "alkyl-C(O)—NH—," as used herein, refers to a alkyl-C(O) group, as defined herein, appended to the parent molecular moiety through a —NH-group, as defined herein.

The term "alkyl-NH—," as used herein, refers to a alkyl group, as defined herein, appended to the parent molecular moiety through an —NH-group, as defined herein.

The term "alkyl-NH—C(O)—," as used herein, refers to a alkyl-NH-group, as defined herein, appended to the parent molecular moiety through a —C(O)— group, as defined herein.

The term "alkyl-NH—S(O)$_2$—," as used herein, refers to a alkyl-NH-group, as defined herein, appended to the parent molecular moiety through a —S(O)$_2$— group, as defined herein.

The term "alkyl-S—," as used herein, refers to a alkyl group, as defined herein, appended to the parent molecular moiety through a —S— group, as defined herein.

The term "alkyl-S(O)$_2$—," as used herein, refers to an alkyl group, as defined herein, appended to the parent molecular moiety through a —S(O)$_2$— group, as defined herein.

The term "alkyl-S(O)$_2$—NH—," as used herein, refers to a alkyl-S(O)$_2$— group, as defined herein, appended to the parent molecular moiety through a —NH-group, as defined herein.

The term "alkylene," denotes a divalent group derived from a straight or branched chain hydrocarbon of from 1 to 10 carbon atoms. Representative examples of alkylene include, but are not limited to, —CH$_2$—, —CH$_2$CH$_2$—, —CH$_2$CH$_2$CH$_2$—, —CH$_2$CH$_2$CH$_2$CH$_2$— and —CH$_2$CH(CH$_3$)CH$_2$—.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl and tetrahydronaphthyl.

The aryl groups of this invention can be substituted with 0, 1, 2, or 3 substituents independently selected from alkenyl, alkoxy, alkoxyalkyl, alkoxycarbonyl, alkyl, alkylcarbonyl, alkylcarbonyloxy, alkynyl, aryloxy, arylalkenyl, carboxy, carboxyalkyl, cyano, cyanoalkyl, formyl, halogen, haloalkyl, haloalkoxy, heterocycle, hydroxy, hydroxyalkyl, nitro, R$_e$R$_f$N—, R$_e$R$_f$N—C(O)—, aryl and heterocycle, wherein the aryl of aryloxy, the substituent aryl and the substituent heterocycle can each be substituted with 0, 1, 2, or 3 substitutents selected from the group consisting of alkenyl, alkoxy, alkoxycarbonyl, alkyl, alkylcarbonyl, carboxy, carboxyalkyl, cyano, cyanoalkyl, halogen, haloalkyl, haloalkoxy, hydroxy, hydroxyalkyl and nitro, wherein R$_e$ and R$_f$ are each individually selected from the group consisting of hydrogen, alkyl and alkylcarbonyl.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl and and 2-naphth-2-ylethyl.

The term "arylalkenyl," as used herein, refers to an aryl group, as defined herein, appended to the parent molecular moiety through an alkenyl group, as defined herein. Representative examples of arylalkenyl include, but are not limited to, prop-1-enylbenzene, 1-(prop-1-enyl)naphthalene and the like.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "arylcarbonylalkyl" as used herein, refers to an arylcarbonyl group, as defined herein, appended to the parent molecular moiety through a carbonyl group, as defined herein. Representative examples of arylcarbonylalkyl include, but are not limited to, propiophenone, 1-(1-naphthyl)propan-1-one and the like.

The term "aryloxy," as used herein, refers to an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy and 3,5-dimethoxyphenoxy.

The term "aryloxyalkyl," as used herein, refers to an aryloxy group, as defined herein, appended to the parent molecular moiety through an alkyl group, as defined herein. Representative examples of aryloxyalkyl include, but are not limited to, 2-phenoxyethyl, 3-naphth-2-yloxypropyl and 3-bromophenoxymethyl.

The term "arylsulfonyl" as used herein, refers to an aryl group, as defined herein, appended to the parent molecular moiety through a sulfonyl group, as defined herein. Representative examples of arylsulfonyl include but are not limited to (ethylsulfonyl)benzene, 1-(ethylsulfonyl)naphthalene and the like.

The term "aryl-C(O)—," as used herein, refers to a aryl group, as defined herein, appended to the parent molecular moiety through an —C(O)— group, as defined herein.

The term "aryl-C(O)—NH—," as used herein, refers to a aryl-C(O)— group, as defined herein, appended to the parent molecular moiety through a —NH— group, as defined herein.

The term "aryl-C=N—O—," as used herein, refers to a aryl group, as defined herein, appended to the parent molecular moiety through a —C=N—O— group, as defined herein.

The term "aryl-NH—," as used herein, refers to a aryl group, as defined herein, appended to the parent molecular moiety through a —NH— group, as defined herein.

The term "aryl-NH—C(O)—," as used herein, refers to a aryl-NH-group, as defined herein, appended to the parent molecular moiety through an —C(O)— group, as defined herein.

The term "aryl-NH—S(O)$_2$—," as used herein, refers to a aryl-NH— group, as defined herein, appended to the parent molecular moiety through a —S(O)$_2$— group, as defined herein.

The term "aryloxy," as used herein, refers to an aryl group, as defined herein, appended to the parent molecular moiety through an oxy group, as defined herein.

The term "aryl-S—," as used herein, refers to a aryl group, as defined herein, appended to the parent molecular moiety through an —S— group, as defined herein.

The term "aryl-S-alkyl-C(O)—," as used herein, refers to a aryl-S-alkyl group, as defined herein, appended to the parent molecular moiety through a —C(O)— group, as defined herein.

The term "aryl-S(O)$_2$—," as used herein, refers to a aryl group, as defined herein, appended to the parent molecular moiety through a —S(O)$_2$— group, as defined herein.

The term "aryl-S(O)$_2$—NH—," as used herein, refers to a aryl-S(O)$_2$— group, as defined herein, appended to the parent molecular moiety through a —NH— group, as defined herein.

The term "arylalkyl-C(O)—," as used herein, refers to a arylalkyl group, as defined herein, appended to the parent molecular moiety through a —C(O)— group, as defined herein.

The term "arylalkyl-C(O)—NH—," as used herein, refers to a arylalkyl-C(O)— group, as defined herein, appended to the parent molecular moiety through a —NH— group, as defined herein.

The term "arylalkyl-NH—," as used herein, refers to a arylalkyl group, as defined herein, appended to the parent molecular moiety through a —NH— group, as defined herein.

The term "arylalkyl-NH—C(O)—," as used herein, refers to a arylalkyl-NH— group, as defined herein, appended to the parent molecular moiety through a —C(O)— group, as defined herein.

The term "arylalkyl-NH—S(O)$_2$—," as used herein, refers to a arylalkyl-NH— group, as defined herein, appended to the parent molecular moiety through a —S(O)$_2$— group, as defined herein.

The term "arylalkoxy," as used herein, refers to a aryl group, as defined herein, appended to the parent molecular moiety through a alkoxy group, as defined herein.

The term "arylalkyl-S—," as used herein, refers to a arylalkyl group, as defined herein, appended to the parent molecular moiety through a —S— group, as defined herein.

The term "arylalkyl-S(O)$_2$—," as used herein, refers to a arylalkyl group, as defined herein, appended to the parent molecular moiety through an —S(O)$_2$— group, as defined herein.

The term "arylalkyl-S(O)$_2$—NH—," as used herein, refers to an arylalkyl-S(O)$_2$—NH— group, as defined herein, appended to the parent molecular moiety through a —NH— group, as defined herein.

The term "biarylalkyl" as used herein, refers to two aryl groups, as defined herein, appended to the parent molecular moiety through an alkyl group, as defined herein. Representative examples of biarylalkyl include but are not limited to (1-phenylbutyl)benzene and the like.

The term "carbonyl," as used herein, refers to a —C(O)— group.

The term "carbonylalkyl," as used herein, refers to a carbonyl group, as defined herein, appended to the parent molecular moiety through an alkyl group, as defined herein.

The term "cycloalkyl," as used herein, refers to a mono-cyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo(3.1.1)heptane, bicyclo(2.2.1)heptane, bicyclo(2.2.2)octane, bicyclo(3.2.2)nonane, bicyclo(3.3.1)nonane and bicyclo(4.2.1)nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo(3.3.1.0$^{3,7}$)nonane and tricyclo(3.3.1.1$^{3,7}$)decane (adamantane).

The cycloalkyl groups of this invention can be substituted with 0, 1, 2, or 3 substituents independently selected from the group consisting of alkenyl, alkoxy, alkoxylalkyl, alkoxycarbonyl, alkyl, alkylcarbonyl, alkylcarbonyloxy, alkynyl, aryl, aryloxy, arylalkenyl, carboxy, carboxyalkyl, cyano, cyanoalkyl, formyl, halogen, haloalkyl, haloalkoxy, heterocycle, hydroxy, hydroxyalkyl, nitro, R$_e$R$_f$N— and R$_e$R$_f$N—C(O)—, wherein R$_e$ and R$_f$ are each individually selected from the group consisting of hydrogen, alkyl and alkylcarbonyl.

The term "cycloalkyl-C(O)—," as used herein, refers to a cycloalkyl group, as defined herein, appended to the parent molecular moiety through a —C(O)— group, as defined herein.

The term "cycloalkyl-C(O)—NH—," as used herein, refers to a cycloalkyl-C(O)— group, as defined herein, appended to the parent molecular moiety through a —NH— group, as defined herein.

The term "cycloalkyl-NH—," as used herein, refers to a cycloalkyl group, as defined herein, appended to the parent molecular moiety through a —NH—, group, as defined herein.

The term "cycloalkyl-NH—C(O)—," as used herein, refers to a cycloalkyl-NH— group, as defined herein, appended to the parent molecular moiety through a —C(O)— group, as defined herein.

The term "cycloalkyl-NH—S(O)$_2$—," as used herein, refers to a cycloalkyl-NH— group, as defined herein, appended to the parent molecular moiety through a —S(O)$_2$— group, as defined herein.

The term "cycloalkoxy," as used herein, refers to a cycloalkyl group, as defined herein, appended to the parent molecular moiety through an oxy group, as defined herein.

The term "cycloalkyl-S—," as used herein, refers to a cycloalkyl group, as defined herein, appended to the parent molecular moiety through an —S— group, as defined herein.

The term "cycloalkyl-S(O)$_2$—," as used herein, refers to a cycloalkyl group, as defined herein, appended to the parent molecular moiety through a —S(O)$_2$— group, as defined herein.

The term "cycloalkyl-S(O)$_2$—NH—," as used herein, refers to a cycloalkyl-S(O)$_2$— group, as defined herein, appended to the parent molecular moiety through a —NH— group, as defined herein.

The term "cycloalkenyl" as used herein, refers to a cycloalkyl group, as defined herein, which contains 1 or 2 double bonds. Examples of cycloalkenyl groups include cyclobutenyl, cyclopentenyl, cyclohexenyl, cycloheptenyl, and cyclooctenyl.

The cycloalkenyl groups of this invention can be substituted with 0, 1, 2, or 3 substituents independently selected from the group consisting of alkenyl, alkoxy, alkoxycarbonyl, alkyl, alkylcarbonyl, alkylcarbonyloxy, alkynyl, carboxy, carboxyalkyl, cyano, cyanoalkyl, formyl, halogen, haloalkyl, hydroxy, hydroxyalkyl, nitro, R$_e$R$_f$N— and R$_e$R$_f$N—C(O)—, wherein R$_e$ and R$_f$ are each individually selected from the group consisting of hydrogen, alkyl and alkylcarbonyl.

The term "cycloalkenylalkyl," as used herein, refers to a cycloalkenyl group, as defined herein, appended to the parent molecular moiety through an alkyl group, as defined herein.

The term "cycloalkenyl-C(O)—," as used herein, refers to a cycloalkenyl group, as defined herein, appended to the parent molecular moiety through a —C(O)— group, as defined herein.

The term "cycloalkenyl-C(O)—NH—," as used herein, refers to a cycloalkenyl-C(O)— group, as defined herein, appended to the parent molecular moiety through a —NH— group, as defined herein.

The term "cycloalkenyl-NH—," as used herein, refers to a cycloalkenyl group, as defined herein, appended to the parent molecular moiety through a —NH— group, as defined herein.

The term "cycloalkenyl-NH—C(O)—," as used herein, refers to a cycloalkenyl-NH— group, as defined herein, appended to the parent molecular moiety through a —C(O)— group, as defined herein.

The term "cycloalkenyl-NH—S(O)$_2$—," as used herein, refers to a cycloalkenyl-NH— group, as defined herein, appended to the parent molecular moiety through a —S(O)$_2$— group, as defined herein.

The term "cycloalkenyloxy," as used herein, refers to a cycloalkenyl group, as defined herein, appended to the parent molecular moiety through an oxy group, as defined herein.

The term "cycloalkenyl-S—," as used herein, refers to a cycloalkenyl group, as defined herein, appended to the parent molecular moiety through an —S— group, as defined herein.

The term "cycloalkenyl-S(O)$_2$—," as used herein, refers to a cycloalkenyl group, as defined herein, appended to the parent molecular moiety through a —S(O)$_2$— group, as defined herein.

The term "cycloalkenyl-S(O)$_2$—NH—," as used herein, refers to a cycloalkenyl-S(O)$_2$— group, as defined herein, appended to the parent molecular moiety through a —NH— group, as defined herein.

The term "halo" or "halogen," as used herein, refers to —Cl, —Br, —I or —F.

The term "haloalkoxy," as used herein, refers to at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy and pentafluoroethoxy.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl and 2-chloro-3-fluoropentyl.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from the group consisting of oxygen, nitrogen and sulfur; or a 5-, 6- or 7-membered ring containing one, two or three heteroatoms wherein the heteroatoms are independently selected from the group consisting of nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo(b,d)furanyl, dibenzo(b,d)thienyl, naphtho(2,3-b)furan, naphtho(2,3-b)thienyl, phenazinyl, phenothiazinyl, phenoxazinyl, thianthrenyl, thioxanthenyl and xanthenyl.

The heterocycles of this invention can be substituted with 0, 1, 2, or 3 substituents independently selected from the group consisting of alkenyl, alkoxy, alkoxyalkyl, alkoxycarbonyl, alkyl, alkylcarbonyl, alkylcarbonyloxy, alkynyl, aryl, aryloxy, arylalkenyl, carboxy, carboxyalkyl, cyano, cyanoalkyl, formyl, halogen, haloalkyl, haloalkoxy, heterocycle, hydroxy, hydroxyalkyl, nitro, R$_e$R$_f$N— and R$_e$R$_f$N—C(O)—, wherein the aryl of aryloxy, the the aryl of arylalkenyl, the substituent aryl and the substituent heterocycle can be substituted with 0, 1, 2, or 3 substitutents selected from the group consisting of alkenyl, alkoxy, alkoxycarbonyl, alkyl, alkylcarbonyl, carboxy, carboxyalkyl, cyano, cyanoalkyl, halogen, haloalkyl, haloalkoxy, hydroxy, hydroxyalkyl and nitro, wherein R$_e$ and R$_f$ are each individually selected from the group consisting of hydrogen, alkyl and alkylcarbonyl.

The term "heterocycle-alkyl," as used herein, refers to a heterocycle, as defined herein, appended to the parent molecular moiety through an alkyl group, as defined herein. Representative examples of heterocycle-alkyl include, but are not limited to, pyridin-3-ylmethyl and 2-pyrimidin-2-ylpropyl.

The term "heterocycle-C(O)—," as used herein, refers to a heterocycle group, as defined herein, appended to the parent molecular moiety through a —C(O)— group, as defined herein.

The term "heterocycle-C(O)—NH—," as used herein, refers to a heterocycle-C(O)— group, as defined herein, appended to the parent molecular moiety through a —NH— group, as defined herein.

The term "heterocycle-NH—," as used herein, refers to a heterocycle group, as defined herein, appended to the parent molecular moiety through a —NH— group, as defined herein.

The term "heterocycle-NH—C(O)—," as used herein, refers to a heterocycle-NH— group, as defined herein, appended to the parent molecular moiety through a —C(O)— group, as defined herein.

The term "heterocycle-NH—S(O)$_2$—," as used herein, refers to a heterocycle-NH— group, as defined herein, appended to the parent molecular moiety through a —S(O)$_2$— group, as defined herein.

The term "heterocycle-O—," as used herein, refers to a heterocycle group, as defined herein, appended to the parent molecular moiety through an —O— group, as defined herein.

The term "heterocycle-S—," as used herein, refers to a heterocycle group, as defined herein, appended to the parent molecular moiety through an —S— group, as defined herein.

The term "heterocycle-S(O)$_2$—," as used herein, refers to a heterocycle group, as defined herein, appended to the parent molecular moiety through a —S(O)$_2$— group, as defined herein.

The term "heterocycle-S(O)$_2$—NH—," as used herein, refers to a heterocycle-S(O)$_2$— group, as defined herein, appended to the parent molecular moiety through an —NH— group, as defined herein.

The term "heterocycle-alkyl-C(O)—," as used herein, refers to a heterocycle-alkyl group, as defined herein, appended to the parent molecular moiety through an —C(O)— group, as defined herein.

The term "heterocycle-alkyl-C(O)—NH—," as used herein, refers to a heterocycle-alkyl-C(O)— group, as defined herein, appended to the parent molecular moiety through a —NH— group, as defined herein.

The term "heterocycle-alkyl-NH—," as used herein, refers to a heterocycle-alkyl group, as defined herein, appended to the parent molecular moiety through a —NH— group, as defined herein.

The term "heterocycle-alkyl-NH—C(O)—," as used herein, refers to a heterocycle-alkyl-NH— group, as defined herein, appended to the parent molecular moiety through a —C(O)— group, as defined herein.

The term "heterocycle-alkyl-NH—S(O)$_2$—," as used herein, refers to a heterocycle-alkyl-NH— group, as defined herein, appended to the parent molecular moiety through a —S(O)$_2$— group, as defined herein.

The term "heterocycle-alkyl-O—," as used herein, refers to a heterocycle-alkyl group, as defined herein, appended to the parent molecular moiety through a —O— group, as defined herein.

The term "heterocycle-alkyl-S—," as used herein, refers to a heterocycle-alkyl group, as defined herein, appended to the parent molecular moiety through a —S— group, as defined herein.

The term "heterocycle-alkyl-S(O)$_2$—," as used herein, refers to a heterocycle-alkyl group, as defined herein, appended to the parent molecular moiety through a —S(O)$_2$— group, as defined herein.

The term "heterocycle-alkyl-S(O)$_2$—NH—," as used herein, refers to a heterocycle-alkyl-S(O)$_2$— group, as defined herein, appended to the parent molecular moiety through a —NH— group, as defined herein.

The term "hydroxy," as used herein, refers to an —OH group.

The term "hydroxyalkyl," as used herein, refers to a hydroxy group, as defined herein, appended to the parent molecular moiety through an alkyl group, as defined herein. Representative examples of hydroxyalkyl include, but are not limited to, hydroxybutyl, hydroxypentyl and hydroxyhexyl.

The term "—NR$_b$-alkyl," as used herein, refers to a —NR$_b$— group, as defined herein, appended to the parent molecular moiety through an alkyl group, as defined herein.

The term "oxo," as used herein, refers to a =O moiety.

The term "sulfonyl," as used herein, refers to a —SO$_2$— group.

The present compounds can exist as therapeutically suitable salts. The term "therapeutically suitable salt," refers to salts or zwitterions of the compounds which are water or oil-soluble or dispersible, suitable for treatment of disorders without undue toxicity, irritation and allergic response, commensurate with a reasonable benefit/risk ratio and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isothionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric and the like. The amino groups of the compounds can also be quaternized with alkyl chlorides, bromides and iodides such as methyl, ethyl, propyl, isopropyl, butyl, lauryl, myristyl, stearyl and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine and the like, are contemplated as being within the scope of the present invention.

The present compounds can also exist as therapeutically suitable esters and prodrugs. The term "therapeutically suitable esters and prodrug," refers to those esters and prodrugs or zwitterions which are suitable for use in contact with the tissues of patients without undue toxicity, irritation and allergic response, are commensurate with a reasonable benefit/risk ratio and are effective for their intended use. The term "prodrug," refers to compounds which are rapidly transformed in vivo to the parent compounds of formula (I-II) for example, by hydrolysis in blood. The term "therapeutically suitable ester," refers to compounds which are rapidly transformed in vivo to the parent compounds of formula (I-II) for example, by hydrolysis in blood. The term "therapeutically suitable ester," refers to alkoxycarbonyl groups appended to the parent molecule on an available carbon atom. More specifically, a "therapeutically suitable ester," may exist on one or more available aryl, cycloalkyl and heterocycle group as defined herein.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described herein below and resolved by techniques well-known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof; oils; glycols; solutions; buffering, coloring, releasing, coating, sweetening, flavoring and perfuming agents; and the like. These therapeutic compositions can be administered parenterally, intracistemally, orally, rectally, or intraperitoneally.

Liquid dosage forms for oral administration of the present compounds comprise formulations of the same as emulsions, microemulsions, solutions, suspensions, syrups and elixirs. In addition to the compounds, the liquid dosage forms can contain diluents and/or solubilizing or emulsifying agents. Besides inert diluents, the oral compositions can include wetting, emulsifying, sweetening, flavoring and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents which dissolve or disperse in the injectable media.

Antagonism of the effects of MCH through the MCH receptor by the compounds of the present invention can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders and granules. In such forms, the compound is mixed with at least one inert, therapeutically suitable excipient such as a carrier, filler, extender, disintegrating agent, solution retarding agent, wetting agent, absorbent, or lubricant. With capsules, tablets and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin and the rate of absorption can be controlled by providing a rate controlling membrane or by dispersing the compounds in a polymer matrix or gel.

Disorders caused or exacerbated by MCH are treated or prevented in a patient by administering to the patient, a therapeutically effective amount of compound of the present invention in such an amount and for such time as is necessary to achieve the desired result. The term "therapeutically effective amount," refers to a sufficient amount of a compound to effectively emeliorate disorders mediated by MCH, by antagonizing the effect of MCH through the MCH receptor at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. In general, treatment regimens comprise administration to a patient in need of such treatment from about 10 mg to about 1000 mg of the compounds per day in single or multiple doses.

Determination of Biological Activity

Assay for Release of Intracellular Calcium:

Activation of the melanin concentrating hormone receptor (MCHR) by MCH induces the release of $Ca^{++}$ from intracellular stores. This intracellular calcium release is measured using a fluorometric imaging plate reader (FLIPR™, Molecular Devices Corp.) in conjunction with the $Ca^{++}$-sensitive dye Fluo-4. Release of $Ca^{++}$ from intracellular stores causes an increase in fluorescence of the dye that is proportional to $Ca^{++}$ concentration. In particular, the assay is carried out as follows: The cells are cultured in MEM/10% fetal bovine serum/50 µg/mL gentamicin/200 µg/ml Zeocin. The cells are plated at 100,000 cells/well in poly-D-lysine coated, 96 FLIPR™ assay plates (BD Biosciences, Bedford, Mass. After two days, cells are loaded with the Calcium Assay Reagent for one hour at 37° C. Test compounds are prepared at 60 µM in 6% dimethyl sulfoxide. The cell plate is placed in the FLIPR™ and 50 µl/well of test compound is delivered. The calcium signal is followed for 3 minutes to assay for potential agonist activity by the test compounds. Then, 50 µl/well of 6 µM human MCH (in Dulbecco's phosphate-buffered saline (PBS) containing 0.1% bovine serum albumin (BSA)) is added and the ligand-induced calcium signal is followed for an additional 3 minutes. Antagonist activity, as determined by the test compound's ability to inhibit MCH-induced $Ca^{++}$ flux, is calculated as percent inhibition as described by the following formula:

$$\% \text{ inhibition} = [1 - ((fTC - fB)/(fMCH - fB))] \times 100$$

fTC=MCH-induced fluorescence in the presence of test compound;

fMCH=MCH-induced fluorescence in the absence of test compound; and fB=baseline fluorescence.

MCH (1 µM) usually elicits a response of 5,000–6,000 relative fluorescence units (RFU) with a baseline of approximately 700 RFU. Calcium Assay Reagent fluorescence is measured at 488 nm, with an exposure of 0.40 sec. and F-stop=2.0 and the laser set at 0.20–0.40 W constant light output. It should be noted that both antagonists and inverse agonists would be expected to produce similar results in this assay. Both types of agent have been found to be useful therapeutically for inhibition of signaling by various GPCR.

The compounds of the present invention inhibit MCH induced fluorescence at a dose of 10 μM. In a preferred range, compounds of the present invention inhibit MCH induced fluorescence in a range of 75–100% inhibition of MCH at a dose of 10 μM. In a more preferred range, compounds of the present invention inhibit MCH induced fluorescence in a range of 90–100% inhibition of MCH at a dose of 10 μM.

As antagonists of MCH action upon the MCH receptor, therefore, the compounds of the present invention are useful in treating disorders that are mediated by MCH through the MCH receptor. Disorders that are mediated by MCH through the MCH receptor are obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders. Therefore the compounds of the present invention are useful in treating obesity, abnormalities in reproduction and sexual behavior, thyroid hormone secretion, diuresis and water/electrolyte homeostasis, sensory processing, memory, sleeping and arousal, anxiety and depression, seizure and in treatment of neurodegeneration or psychiatric disorders.

Therapeutic agents acting through MCH receptor may also be useful in treatment of abnormalities in reproduction and sexual behavior (Murray, J. F.; Mercer J. G., Adan R. A., Datta J. J., Aldairy C, Moar K M, Baker B I, Stock M J, Wilson, C. A.; The effect of leptin on luteinizing hormone release is exerted in the zona incerta and mediated by melanin-concentrating hormone. J Neuroendocrinol 12:1133–1139, 2000.; Gonzalez, M. I., Baker, B. I., Wilson, C. A.; Stimulatory effect of melanin-concentrating hormone on luteinising hormone release. Neuroendocrinology 66:254–262, 1997.; Murray, J. F., Adan, R. A., Walker, R., Baker, B. I., Thody, A. J., Nijenhuis, W. A., Yukitake, J., Wilson, C. A.; Melanin-concentrating hormone, melanocortin receptors and regulation of luteinizing hormone release. J Neuroendocrinol 12:217–223, 2000.; Nahon, J. L.; The melanin-concentrating hormone: from the peptide to the gene. Crit Rev Neurobiol 8:221–262, 1994.)

Therapeutic agents acting through MCH receptor may also be useful in treatment of thyroid hormone secretion (Kennedy, A. R., Todd, J. F., Stanley, S. A., Abbott, C. R., Small, C. J., Ghatei, M. A., Bloom, S. R.; Melanin-concentrating hormone (MCH) suppresses thyroid stimulating hormone (TSH) release, in vivo and in vitro, via the hypothalamus and the pituitary. Endocrinology 142:3265–3268. 2001).

Therapeutic agents acting through MCH receptor may also be useful in treatment of diuresis and water/electrolyte homeostasis (Hervieu, G., Volant, K., Grishina, O., Descroix-Vagne, M., Nahon, J. L.; Similarities in cellular expression and functions of melanin-concentrating hormone and atrial natriuretic factor in the rat digestive tract. Endocrinology 137:561–571, 1996.; and Parkes, D. G.; Diuretic and natriuretic actions of melanin concentrating hormone in conscious sheep. J Neuroendocrinol 8:57–63, 1996).

Therapeutic agents acting through MCH receptor may also be useful in treatment of sensory processing (Miller, C. L., Hruby, V. J., Matsunaga, T. O., Bickford, P. C.; Alpha-MSH and MCH are functional antagonists in a CNS auditory gating paradigm. Peptides 14:431–440, 1993.; Kokkotou, E. G., Tritos, N. A., Mastaitis, J. W., Slieker, L., Maratos-Flier, E.; Melanin-concentrating hormone receptor is a target of leptin action in the mouse brain. Endocrinology 142:680–686, 2001).

Therapeutic agents acting through MCH receptor may also be useful in treatment of memory (Monzon, M. E., De Barioglio, S. R.; Response to novelty after i.c.v. injection of melanin-concentrating hormone (MCH) in rats. Physiol Behav 67:813–817, 1999).

Therapeutic agents acting through MCH receptor may also be useful in treatment of sleeping and arousal (Bittencourt, J. C., Presse, F., Arias, C., Peto, C., Vaughan, J., Nahon, J. L., Vale, W., Sawchenko, P. E.; The melanin-concentrating hormone system of the rat brain: an immuno- and hybridization histochemical characterization. J Comp Neurol 319:218–245, 1992.; Nahon, J. L.; The melanin-concentrating hormone: from the peptide to the gene. Crit Rev Neurobiol 8:221–262, 1994).

Therapeutic agents acting through MCH receptor may also be useful in treatment of anxiety and depression (Monzon, M. E., Varas, M. M., De Barioglio, S. R.; Anxiogenesis induced by nitric oxide synthase inhibition and anxiolytic effect of melanin-concentrating hormone (MCH) in rat brain. Peptides 22:1043–1047, 2001.; Monzon, M. E., De Barioglio, S. R.; Response to novelty after i.c.v. injection of melanin-concentrating hormone (MCH) in rats. Physiol Behav 67:813–817, 1999.; Borowsky, B., Durkin, M. M., Ogozalek, K., Marzabadi, M. R., DeLeon, J., Lagu, B., Heurich, R., Lichtblau, H., Shaposhnik, Z., Daniewska, I., Blackburn, T. P., Branchek, T. A., Gerald, C., Vaysse, P. J., Forray, C.; Antidepressant, anxiolytic and anorectic effects of a melanin-concentrating hormone-1 receptor antagonist. Nat. Med. 8:825–830, 2002).

Therapeutic agents acting through MCH receptor may also be useful in treatment of seizure (Knigge, K. M., Wagner, J. E.; Melanin-concentrating hormone (MCH) involvement in pentylenetetrazole (PTZ)-induced seizure in rat and guinea pig. Peptides 18:1095–1097, 1997) and in treatment of neurodegeneration or psychiatric disorders (Nahon, J. L.; The melanin-concentrating hormone: from the peptide to the gene. Crit Rev Neurobiol 8:221–262, 1994).

Synthetic Methods

Abbreviations which have been used in the descriptions of the scheme and the examples that follow are: AcOH for acetic acid, dba for dibenzylideneacetone; DMSO for dimethylsulfoxide; NMP for N-methylpyrrolidinone; DMF for N,N-dimethylformamide; DCC for 1,3-dicyclohexylcarbodiimide, DIC for 2-dimethylaminoisopropyl chloride hydrochloride, EtOH for ethanol, EtOAc for ethyl acetate, HATU for O-(7-azabenzotriazol-1-yl)-N,N,N',N'-tetramethyluronium hexafluorophosphate, HBTU for O-benzotriazole-1-yl)-N,N,N',N'-tetramethyluronium hexafluorophosphate, MeOH for methanol, TFA for trifluoroacetic acid; THF for tetrahydrofuran; EDCI for 1-(3-dimethylaminopropyl)-3-ethylcarbodiimide hydrochloride; HOAt for 1-hydroxy-7-azabenzotriazole and HOBt for 1-hydroxybenzotriazole hydrate.

The compounds and processes of the present invention will be better understood in connection with the following synthetic schemes which together illustrate the methods by which the compounds of the invention may be prepared. The groups $R_1$, $R_2$, $R_3$, $R_4$, $R_5$, $R_6$, $R_7$, $R_8$, $R_9$, $R_{10}$ are as defined above unless otherwise noted below.

Scheme 1

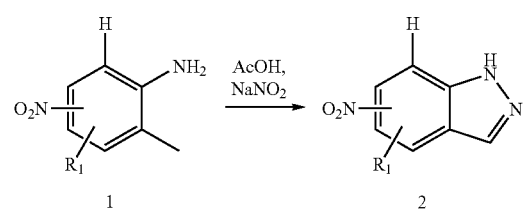

As shown in Scheme 1, compounds of formula 1 (wherein $R_1$ is hydrogen, halogen, alkyl or alkoxy) can be treated with acetic acid and $NaNO_2$ at room temperature to provide compounds of formula 2.

Scheme 2

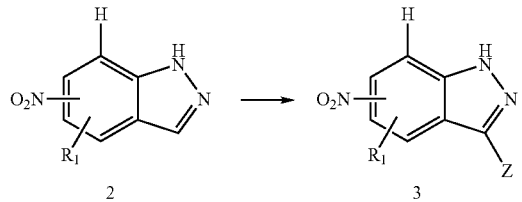

As shown in Scheme 2, compounds of formula 2 can be treated with sodium hydroxide and reagents such as but not limited to sodium hypochlorite or bromine to provide compounds of formula 3, where Z is chlorine or bromine respectively.

Scheme 3

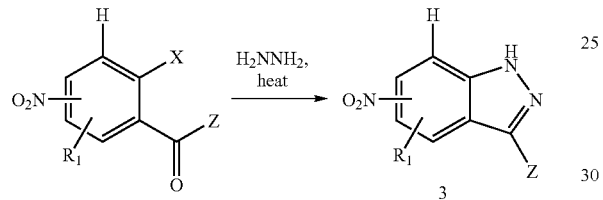

As shown in Scheme 3, nitro benzene compounds (wherein X is halogen and $R_1$ is alkoxy or alkyl) can be treated with hydrazine hydrate under heated conditions to provide compounds of formula 3 where Z is alkyl or hydrogen.

Scheme 4

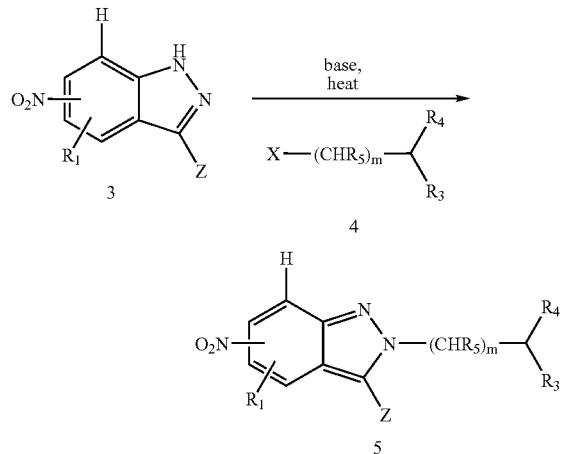

As shown in Scheme 4, compounds of formula 2 or 3 can be treated under heated conditions with base and compounds of formula 4 (wherein $R_3$, $R_4$ and m are described herein and X is halogen, methanesulfonate, toluenesulfonate or triflourosulfonate), to provide compounds of formula 5. Typical bases include but are not limited to cesium carbonate and potassium carbonate and solvents include but are not limited to N,N-dimethylformamide, N,N-dimethylacetamide and tetrahydrofuran.

Scheme 5

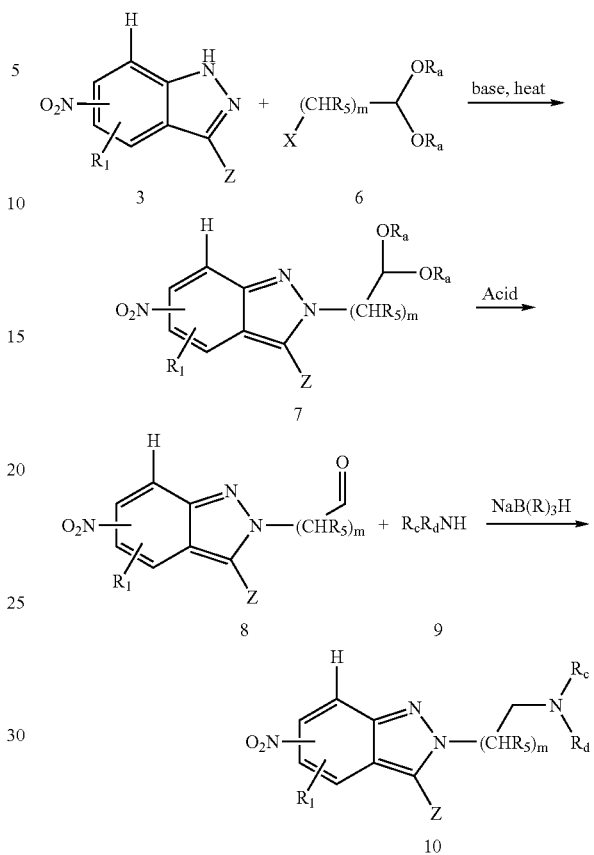

Alternatively, compounds of formula 3 can be treated under heated conditions with compounds of formula 6 (wherein $R_a$ is methyl or ethyl; X is halogen, methanesulfonate, toluenesulfonate or triflourosulfonate and m is defined herein) and base to provide compounds of formula 7. Typical bases include but are not limited to cesium carbonate and potassium carbonate and solvents include but are not limited to N,N-dimethylformamide, N,N-dimethylacetamide and tetrahydrofuran. Compounds of formula 7 can be treated under heated conditions with acid to afford compounds of formula 8. Typical acids include but are not limited to dilute hydrochloric acid or toluenesulfonic acid and the like, in solvents such as aqueous tetrahydrofuran or aqueous methanol. Compounds of formula 8 can then be treated with primary or secondary amines of formula 9 and a reducing agent to afford compounds of formula 10. Typical reducing agents include but are not limited to sodium triacetoxyborohydride, sodium cyanoborohydride and the like; and typical solvents include but are not limited to tetrahydrofuran, isopropyl acetate, methanol, dichloroethane and mixtures thereof.

Scheme 6

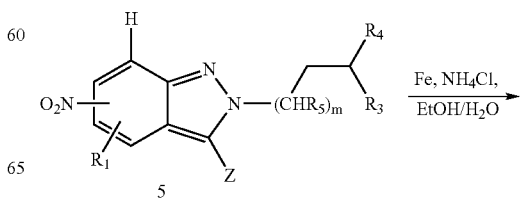

-continued

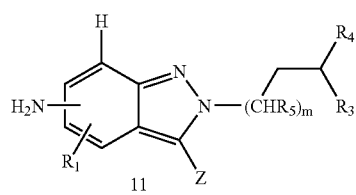

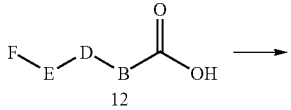

As shown in Scheme 6, compounds of formula 5 can be treated according to conditions commonly known to those skilled in the art that will reduce a nitro group to an amine group such as but not limited to ammonium chloride and iron, hydrogen and Pd/C and the like to afford compounds of formula 11. Solvents include but are not limited to ethanol, methanol, ethyl acetate, H$_2$O and mixtures thereof.

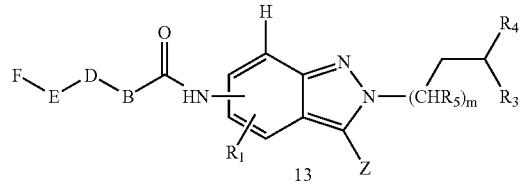

As shown in Scheme 7, amines of formula 11 can be treated with carboxylic acids of formula 12 under conditions know to those skilled in the art that will form amide bonds to provide compounds of formula 13 which are representative of compounds of the present invention. Typical reaction conditions include stirring a compound of formula 11 and a compound of formula 12 with a coupling reagent such as but not limited to EDCI, DCC, DIC, HATU, HBTU, an auxiliary nucleophile such as but not limited to HOBt and HOAt and a base such as but not limited to diisopropylethylamine, triethylamine, N-methylmorpholine in solvents such as but not limited to N,N-dimethylformamide and methylene chloride.

Scheme 7

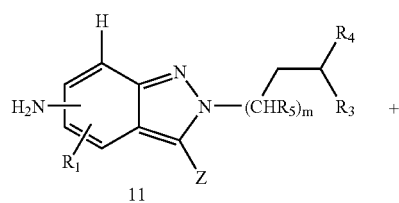

Scheme 8

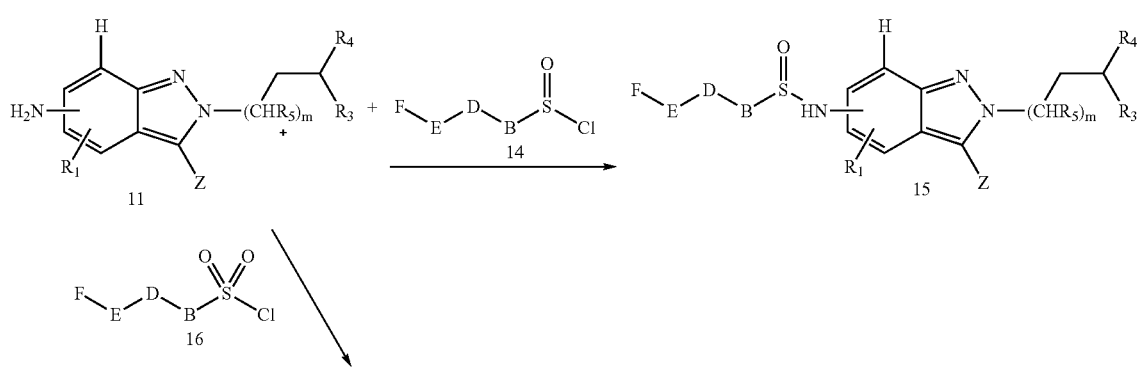

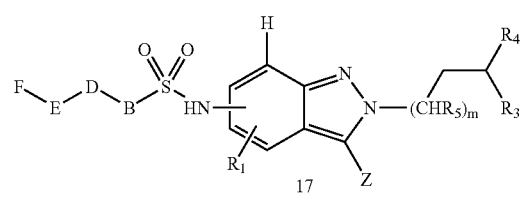

As shown in Scheme 8, compound of formula 11 may also be treated with compounds of formula 14 and a base such as triethylamine in solvents such as tetrahydrofuran to provide compounds of formula 15 which are representative of compounds of the present invention. Similarly, compounds of formula 11 may be treated with compounds of formula 16 and a base such as triethylamine in solvents such as tetrahydrofuran to provide compounds of formula 17 which are representative of compounds of the present invention.

As shown in Scheme 10, compounds of formula 20 which are representative of the compounds of the present invention, where D is a bond and E is —NH— can be prepared from the above mentioned schemes. Compounds of formula 20 can be treated according to conditions known to deprotect amine protecting groups such as hydrochloric acid in acetic acid or trifluoroacetic acid methylene chloride to provide compounds of formula 21.

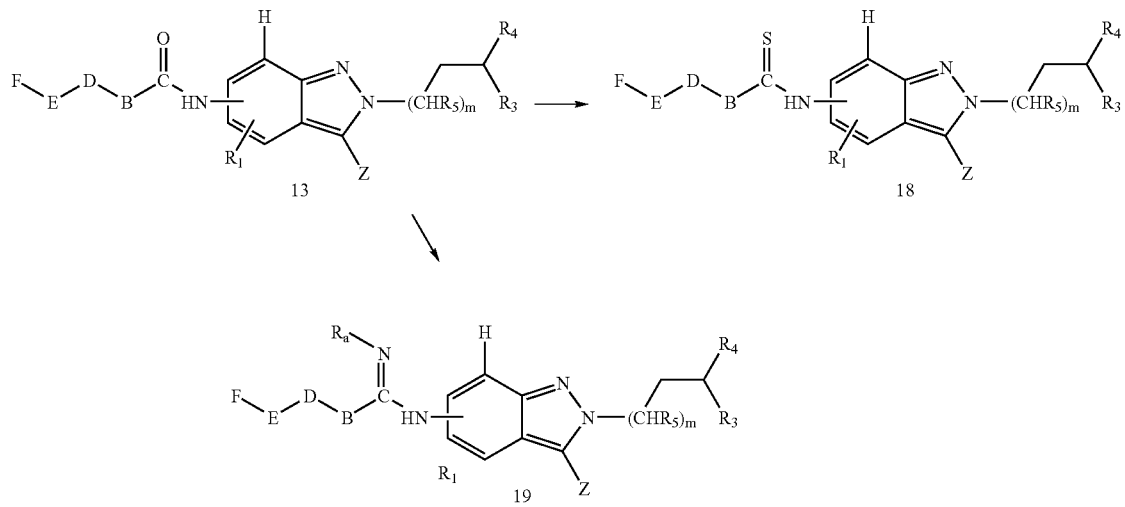

In addition, compounds of formula 13 may be further converted into compounds of formula 18 and 19 as described in Scheme 9. The treatment of compound of formula 13 with Lawessons reagent in solvents such as tetrahydrofuran or toluene will provide compounds of formula 18 which are representative of compounds of the present invention. Alternatively, the treatment of compounds of formula 13 with amines of formula $R_a$—$NH_2$ in a solvent such as toluene under refluxing conditions with a Dean-Stark trap will provide compounds of formula 19 which are a representative of compounds of the present invention.

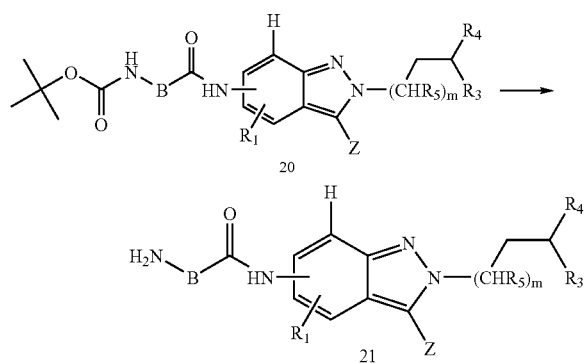

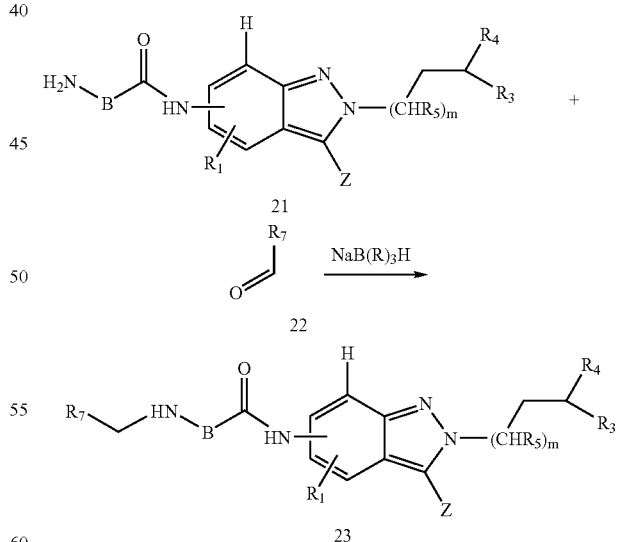

As shown in Scheme 11, compounds of formula 21 can be treated with compounds of formula 22 in the presence of a reducing agent such as but not limited to sodium triacetoxyborohydride, sodium cyanoborohydride to provide compounds of formula 23 which are representative of compounds of the present invention.

Scheme 12

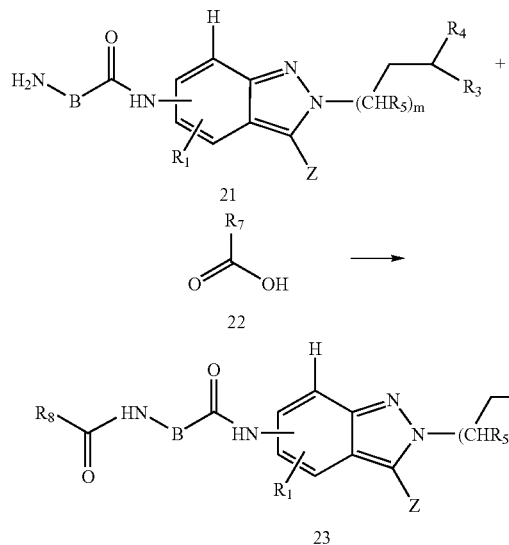

Alternatively, compounds of formula 21 can be treated with carboxylic acids of formula 22 under conditions for amide bond formation to afford compounds of formula 23 which are representative of compounds of the present invention. Typical coupling conditions include stirring compounds of formula 21 and compounds of formula 22 in the presence of EDCI, DCC, DIC, HATU, HBTU and an auxiliary nucleophile such as but not limited to HOBt and HO and a base such as diisopropylethylamine, triethylamine, N-methylmorpholine. Typical solvents include but are not limited to N,N-dimethylformamide and methylene chloride.

Scheme 13

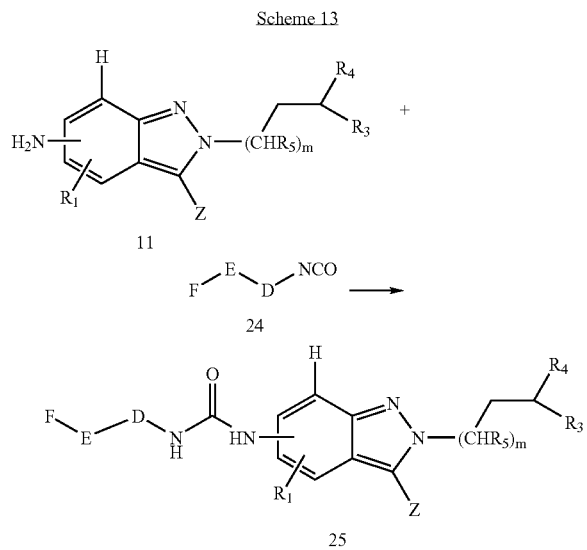

As shown in Scheme 13, compounds of formula 11 can be treated with isocyanates of formula 24 at elevated temperatures in solvents such as but not limited to tetrahydrofuran and dioxane to provide compounds of formula 25, which are representative of compounds of the present invention.

Scheme 14

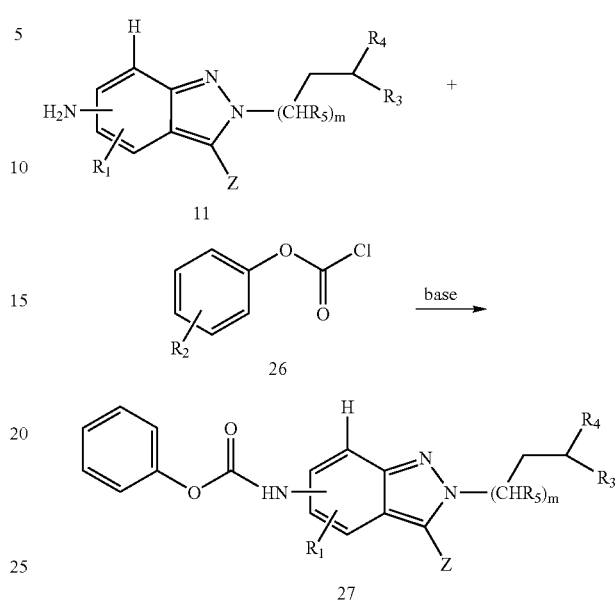

Alternatively, compounds of formula 11 can be treated with phenyl chloroformates of formula 26 in the presence of a base such as but not limited to triethylamine and potassium carbonate in solvents such as but not limited to dichloroethane, methylene chloride and chloroform to provide carbamates of formula 27.

Scheme 15

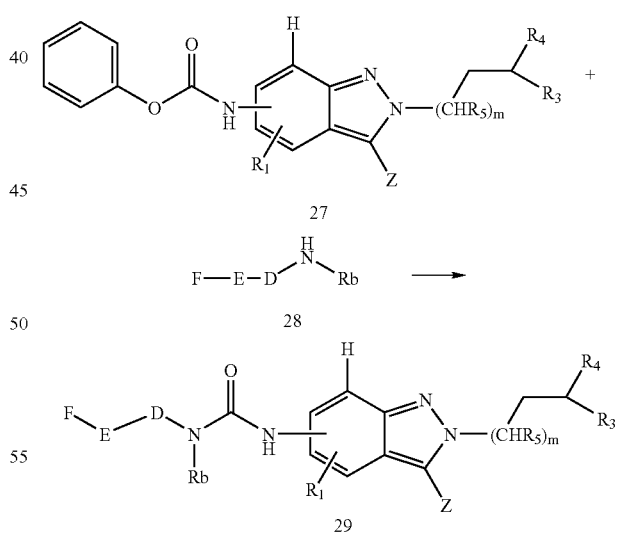

As shown in Scheme 15, carbamates of formula 27 can be treated with primary or secondary amines of formula 28 in the presence of a base such as triethylamine or potassium carbonate in solvents such as N-methylpyrrolidinone or tetrahydrofurane at elevated temperatures to afford compounds of formula 29, which are representative of compounds of the present invention.

Scheme 16

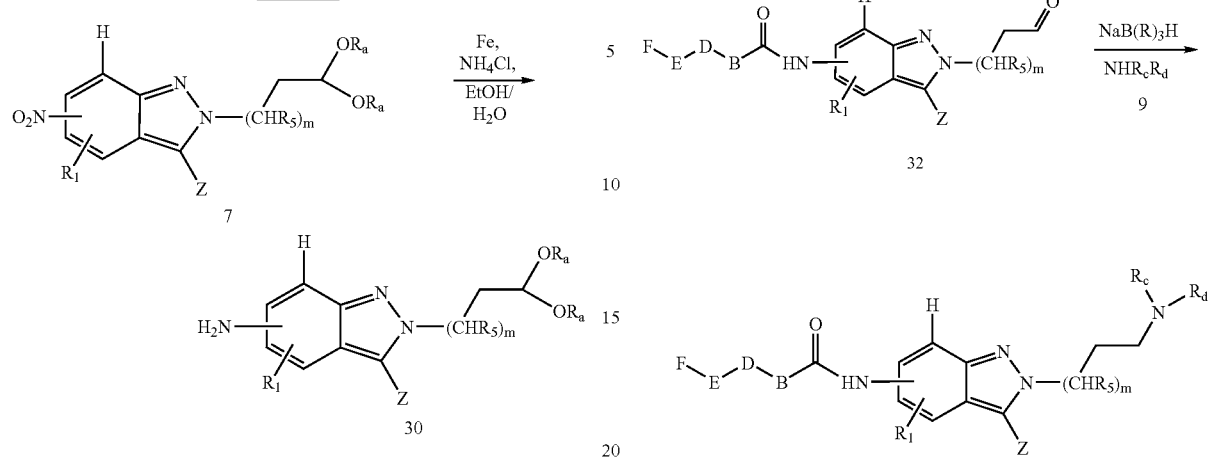

As shown in Scheme 16, the reduction of the nitro functional group of compounds of formula 7 can be achieved utilizing the same conditions described in Scheme 6 to provide compounds of formula 30.

Scheme 17

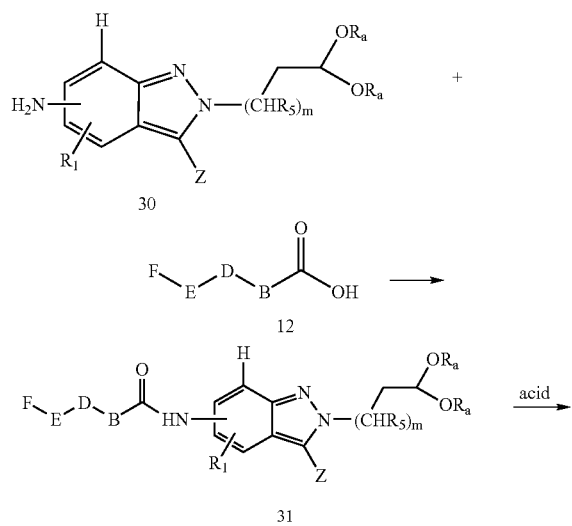

As shown in Scheme 17, compounds of formula 30 can be treated with carboxylic acids of formula 12 under conditions for amide bond formation to afford compounds of formula 31. Typical reaction conditions include stirring a compound of formula 30 and a compound of formula 12 with a coupling reagent such as but not limited to EDCI, DCC, DIC, HATU or HBTU, an auxiliary nucleophile such as but not limited to HOBt or HOAt and a base such as but not limited to diisopropylethylamine, triethylamine or N-methylmorpholine in solvents such as but not limited to N,N-dimethylformamide or methylene chloride. Compounds of formula 31 when treated with an acid such as but not limited to hydrochloric acid or toluenesulfonic acid under heated conditions will provide compounds of formula 32. Compounds of formula 32 can then be treated with primary or secondary amines of formula 9 and a reducing agent such as but not limited to sodium triacetoxyborohydride or sodium cyanoborohydride in solvents such as tetrahydrofuran, isopropanol, methanol or dichloroethane and mixtures thereof to provide compounds of formula 33 which are representative of the compounds of the present invention.

Scheme 18

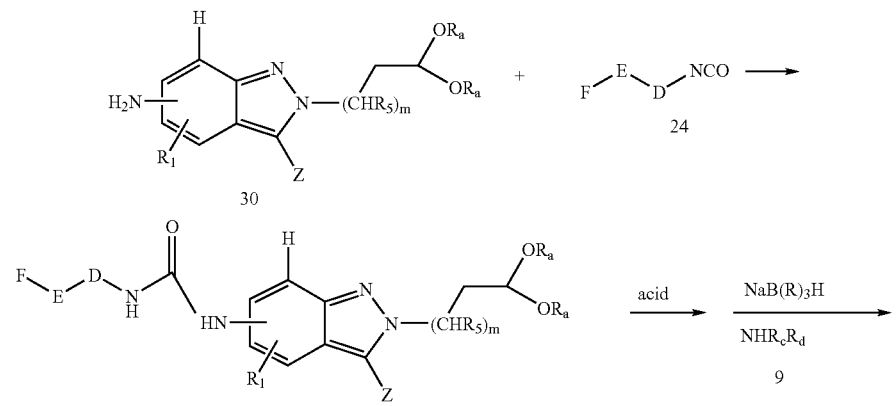

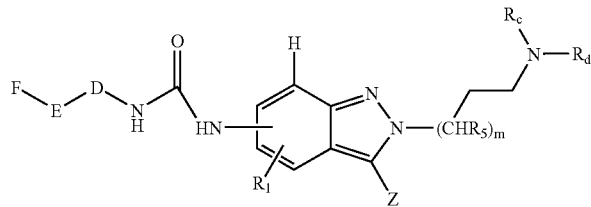

As shown in Scheme 18, compounds of formula 30 can be treated with isocyanates of formula 24 at elevated temperatures to afford compounds of formula 34. Solvents include but are not limited to tetrahydrofuran, dioxane or ether. Compounds of formula 34 can be sequentially treated with acid followed by treatment with compounds of formula 9 under reductive amination conditions as outlined in Scheme 17 to provide compounds of formula 35 which are representative of the compounds of the present invention.

Scheme 19

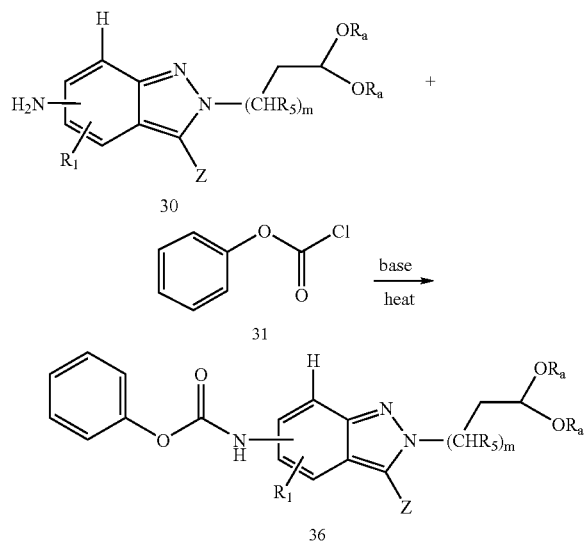

Alternatively, compounds of formula 30 can be treated with phenyl chloroformates of formula 31 in the presence of a base such as but not limited to triethylamine or $K_2CO_3$ in solvents such as but not limited to dichloroethane, methylene chloride or chloroform to provide carbamates of formula 36.

Scheme 20

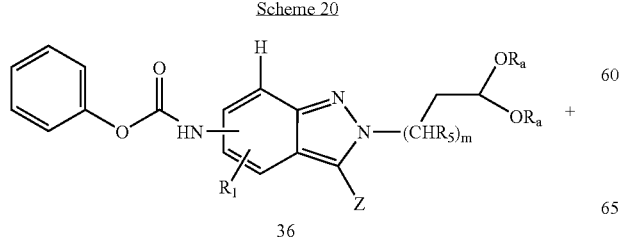

Carbamates of formula 36 can be treated with primary or secondary amines of formula 28 in elevated temperatures to provide ureas of formula 37, which are representative of the compounds of the present invention. Typical reaction conditions include heating a mixture of a compound of formula 36 and a compound of formula 28 in the presence of a base such as triethjylamine or potassium carbonate in solvents such as but not limited to N-methylpyrolidinone or tetrahydrofuran at temperatures between 25 to 200° C. for 1–8 hours.

Scheme 21

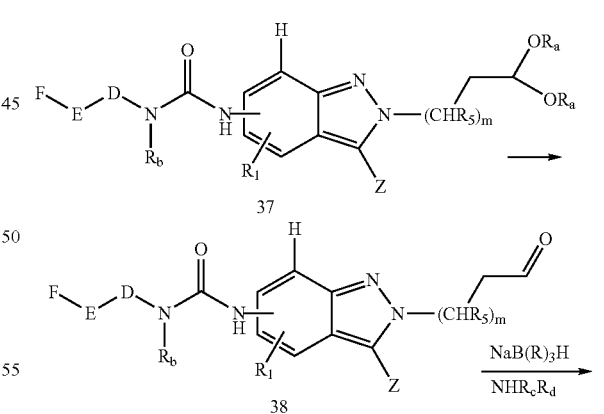

As shown in Scheme 21, compounds of formula 37 can be treated under heated conditions with an acid such as hydrochloric acid or toluenesulfonic acid to provide compounds of formula 38. Compounds of formula 37 can then be treated with a primary or a secondary amines of formula 9 and a reducing agent such as but not limited to sodium triacetoxyborohydride or sodium cyanoborohydride in solvents such as but not limited to tetrahydrofuran, isopropyl alcohol, methanol or dichloroetane or mixtures thereof, to provide compounds of formula 39, which are representative of compounds of the present invention.

Scheme 22

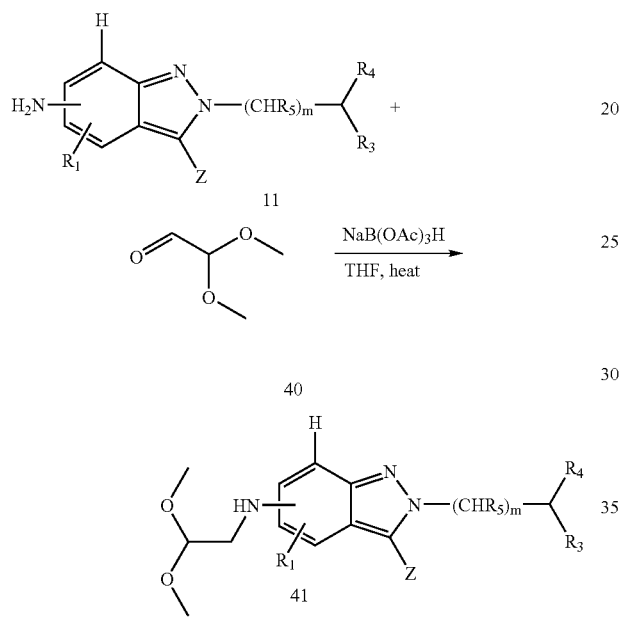

As shown in Scheme 22, compounds of formula 11 when treated with primary or secondary amines of formula 40 and a reducing agent will provide compounds of formula 41. Typical conditions include but are not limited to sodium triacetoxyborohydride or sodium cyanoborohydride in solvents such as but not limited to THF, IPA, MeOH, DCE and mixtures thereof.

Scheme 23

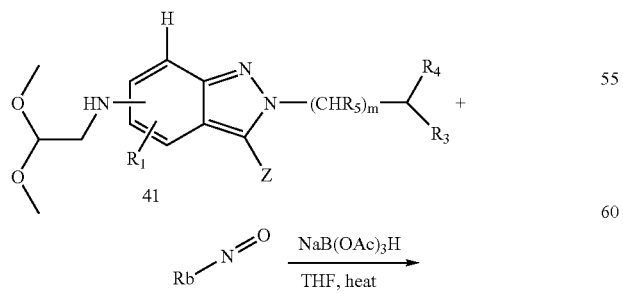

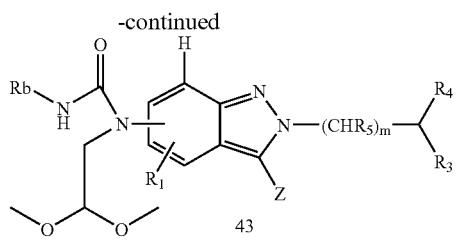

As shown in Scheme 23, compounds of formula 41 when treated with isocyanates of formula 42 in solvents such as but are not limited to THF, dioxane or ether, at elevated temperatures will provide compounds of formula 43.

Scheme 24

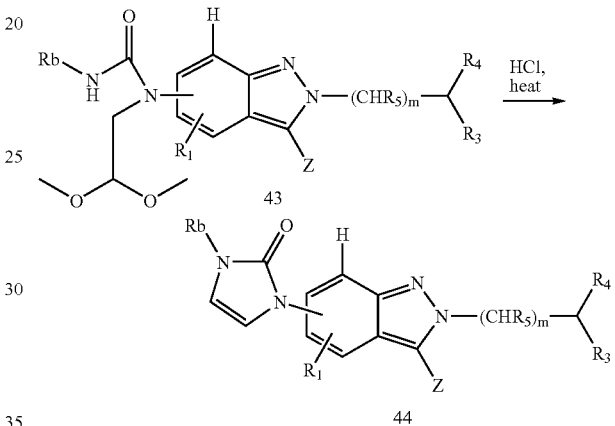

As shown in Scheme 24, compounds of formula 43 when heated in the presence of a catalytic amounts of acid such as but not limited to sulfuric acid or toluenesulfonic acid in solvents such as but not limited to THF, dioxane or ether will provide compounds of the formula 44.

Scheme 25

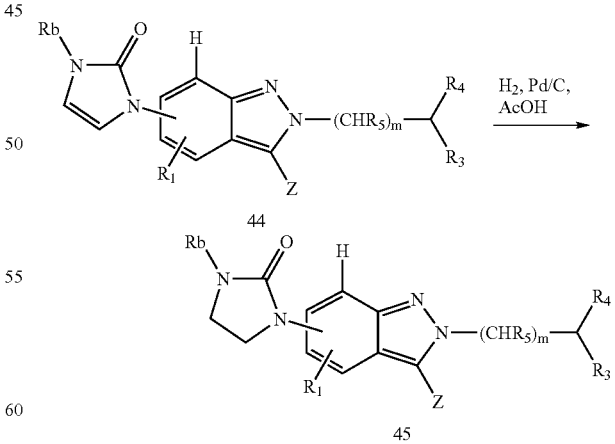

As shown in Scheme 25, compounds of formula 44 when treated to hydrogen gas at a pressure of 30–90 psi and in the presence of a catalyst such as but not limited to palladium on carbon and platinum on carbon in solvents such as but not limited to AcOH, EtOH, EtOAc or MeOH and mixtures thereof, will provide compounds of formula 45 which are representative of the compounds of the present invention.

The present invention will now be described in connection with certain preferred embodiments which are not intended to limit its scope. On the contrary, the present invention covers all alternatives, modifications and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

Compounds of the invention were named by ACD/ChemSketch version 5.01 (developed by Advanced Chemistry Development, Inc., Toronto, ON, Canada) or were given names which appeared to be consistent with ACD nomenclature.

EXPERIMENTALS

Example 1

2-[4-(benzyloxy)phenyl]-N-[2-(2-pyrrolidin-1-yl-ethyl)-2H-indazol-4-yl]acetamide Example 1A 4-nitro-1H-indazole A solution of 2-methyl-3-nitro-aniline (5.00 g, 32.9 mmol) in glacial acetic acid (750 mL) was treated with a solution of sodium nitrite (2.27 g, 32.9 mmol) in water (7.5 mL). The resultant solution was stirred for 15 minutes and allowed to stand at room temperature for 3 days. The acetic acid was removed in vacuo, leaving a pale yellow solid which was dissolved in ethyl acetate (250 mL) and filtered through a plug of silica gel, rinsing with ethyl acetate. The ethyl acetate was removed in vacuo to afford a pale yellow solid. $^1$H NMR (300 MHz, DMSO-$d_6$) δ ppm 7.65 (dd, 1H, $J_1$=7.46, $J_2$=8.48), 8.10 (d, 1H, J=8.48), 8.16 (d, 1H, J=7.46), 8.54 (s, 1H), 13.93 (s, 1H); MS (DCI/NH$_3$) m/z 164 [M+H]$^+$.

Example 1B 4-nitro-2-(2-pyrrolidin-1-yl-ethyl)-2H-indazole

4-Nitroindazole (3.00 g, 18.4 mmol) was dissolved in 60 mL of N,N-dimethylformamide and potassium carbonate (7.50 g, 54.3 mmol) was added. The mixture was stirred for 30 minutes and then 1-(2-chloro-ethyl)-pyrrolidine hydrochloride (4.80 g 28.2 mmol) was added. The reaction mixture was heated to 60° C. for 6 hours, cooled to room temperature and the mixture filtered through a plug of silica gel which was rinsed with triethylamine/ethyl acetate (1/4). The filtrate was concentrated in vacuo to remove N,N-dimethylformamide and the residue purified by flash chromatography (silica gel, triethylamine/ethyl acetate 1/30). $^1$H NMR (300 MHz, DMSO-$d_6$) δ ppm 1.64 (m, 4H), 2.48 (m, 4H), 3.01 (t, 2H, J=6.44), 4.67 (t, 2H, J=6.44), 7.49 (t, 1H, J=8.14), 8.19 (d, 2H, J=7.80), 8.92 (s, 1H); MS (DCI/NH$_3$) m/z 261 [M+H]$^+$.

Example 1C 2-(2-pyrrolidin-1-yl-ethyl)-2H-indazol-4-ylamine

4-Nitro-2-(2-pyrrolidin-1-yl-ethyl)-2H-indazole (1.20 g, 4.62 mmol), iron powder (2.60 g, 46.6 mmol) and ammonium chloride (0.125 g, 2.34 mmol) was suspended in a 4:1 ethanol/H$_2$O solution. The mixture was heated to reflux for 3 hours, cooled to room temperature and the solvent removed in vacuo. The residue was stirred in triethylamine/ethyl acetate (1/4, 30 mL) for 15 minutes and filtered through a plug of silica gel. After rinsing with triethylamine/ethyl acetate (1/4), the filtrate was concentrated to provide the title product. $^1$H NMR (300 MHz, DMSO-$d_6$) δ ppm 1.66 (m, 4H), 2.50 (m, 4H), 2.96 (t, 2H, J=6.44), 4.44 (t, 2H, J=6.44), 5.51 (s, 2H), 6.70 (m, 1H), 6.88 (d, 1H, J=8.48), 6.91 (m, 1H), 8.28 (s, 1H); MS (DCI/NH$_3$) m/z 231 [M+H]$^+$.

Example 1

2-[4-(benzyloxy)phenyl]-N-{[2-(2-pyrrolidin-1-yl-ethyl)-2H-indazol-4-yl]methyl}acetamide A 10 mL culture tube with screw cap was charged with 2-(2-pyrrolidin-1-yl-ethyl)-2H-indazol-4-ylamine (56.0 mg, 0.243 mmol), (4-benzyloxy-phenyl)-acetic acid (60.0 mg, 0.248 mmol), ethyldimethylpropylcarbodiimide hydrochloride (57.0 mg, 0.298 mmol), N-hydroxybenzotriazole (40.0 mg, 0.296 mmol), N-methyl morpholine (64.0 mg, 0.633 mmol), 2 mL of N,N-dimethylformamide and the reaction vessel placed on a shaker for 6 hours. After this time, the N,N-dimethylformamide was removed in vacuo and the residue was dissolved in 1.5 mL of a 1:1 mixture of dimethyl sulfoxide/methanol and purified by preparative reverse-phase HPLC. $^1$H NMR (300 MHz, DMSO-$d_6$) δ ppm 1.70 (m, 4H), 2.60 (m, 4H), 3.10 (s, 2H), 3.68 (s, 2H), 4.48 (t, 2H, J=6.44), 5.09 (s, 2H), 6.97 (m, 2H), 7.12–7.45 (m, 9H), 7.51 (m, 1H), 8.49 (s, 1H), 10.03 (s, 1H); MS (DCI/NH$_3$) m/z 455 [M+H]$^+$.

Example 2

4-oxo-4-(4-phenoxyphenyl)-N-[2-(2-pyrrolidin-1-ylethyl)-2H-indazol-4-yl]butanamide The title compound was prepared according to the procedure for Example 1 substituting 4-oxo-4-(4-phenoxy-phenyl)-butyric acid for (4-benzyloxy-phenyl)-acetic acid. $^1$H NMR (500 MHz, dmso-$d_6$) δ ppm 1.85 (m, 2H), 2.00 (m, 2H), 2.84 (t, 2H), 3.07 (m, 2H), 3.35 (t, 2H), 3.54 (m, 2H), 3.81 (m, 2H), 4.84 (t, 2H), 7.07 (m, 2H), 7.13 (m, 2H), 7.20 (m, 1H), 7.26 (m, 1H), 7.33 (m, 1H), 7.49 (m, 3H), 8.03 (m, 2H), 8.59 (s, 1H), 10.05 (s, 1H); MS (ESI) m/z 457 [M+H]$^+$.

Example 3

4-(1,1'-biphenyl-4-yl)-4-oxo-N-[2-(2-pyrrolidin-1-ylethyl)-2H-indazol-4-yl]butanamide The title compound was prepared according to the procedure for Example 1 substituting 4-biphenyl-4-yl-4-oxo-butyric acid for (4-benzyloxy-phenyl)-acetic acid. $^1$H NMR (500 MHz, dmso-$d_6$) δ ppm 1.84 (m, 2H), 2.01 (m, 2H), 2.88 (t, 2H), 3.08 (m, 2H), 3.43 (m, 2H), 3.56 (m, 2H), 3.82 (m, 2H), 4.84 (t, 2H), 7.21 (m, 1H), 7.34 (m, 1H), 7.44 (m, 1H), 7.52 (m, 3H), 7.76 (m, 2H), 7.85 (m, 2H), 8.10 (m, 2H), 8.61 (s, 1H), 10.08 (s, 1H); MS (ESI) m/z 467 [M+H]$^+$.

Example 4

2-(3-phenoxyphenyl)-N-[2-(2-pyrrolidin-1-ylethyl)-2H-indazol-4-yl]acetamide

The title compound was prepared according to the procedure for Example 1 substituting (3-phenoxy-phenyl)-acetic acid for (4-benzyloxy-phenyl)-acetic acid. $^1$H NMR (500 MHz, dmso-$d_6$) δ ppm 1.84 (m, 2H), 2.01 (m, 2H), 3.07 (m, 2H), 3.54 (m, 2H), 3.77 (s, 2H), 3.81 (m, 2H), 4.84 (t, 2H), 6.89 (m, 1H), 7.03 (m, 3H), 7.14 (m, 2H), 7.21 (m, 1H), 7.38 (m, 4H), 7.46 (m, 1H), 8.55 (s, 1H), 10.19 (s, 1H); MS (ESI) m/z 441 [M+H]$^+$.

Example 5

2-(4-phenoxyphenyl)-N-[2-(2-pyrrolidin-1-ylethyl)-2H-indazol-4-yl]acetamide

The title compound was prepared according to the procedure for Example 1 substituting (4-phenoxy-phenyl)-acetic acid for (4-benzyloxy-phenyl)-acetic acid. $^1$H NMR (300 MHz, DMSO-$d_6$) δ ppm 1.83 (m, 2H), 2.00 (m, 2H), 3.07(m, 2H), 3.51 (m, 2H), 3.69 (t, 2H, J=6.24), 3.71 (s, 2H), 4.65 (t, 2H, J=6.24), 6.97–7.01 (m, 4H), 7.11–7.15 (m, 1H), 7.22 (m, 1H), 7.36–7.40 (m, 4H), 7.64 (m, 1H), 8.34 (s, 1H), 9.56 (s, 1H), 10.53 (s, 1H); MS (DCI/NH$_3$) m/z 441 [M+H]$^+$.

Example 6

2-[4-(benzyloxy)phenyl]-N-[2-(2-piperidin-1-yl-ethyl)-2H-indazol-4-yl]acetamide

Example 6A

4-nitro-2-(2-piperidin-1-ylethyl)-2H-indazole

4-Nitroindazole (1.00 g, 6.14 mmol) was dissolved in 20 mL of N,N-dimethylformamide and potassium carbonate (2.50 g, 18.1 mmol) was added. The mixture was stirred for 30 minutes and then 1-(2-chloro-ethyl)-piperidine hydrochloride (1.73 g, 9.40 mmol) was added. The mixture was heated to 60° C. for 6 hours, cooled to room temperature, the mixture was filtered through a plug of silica gel and rinsed with triethylamine/ethyl acetate (1/4). The filtrate was concentrated in vacuo to remove N,N-dimethylformamide and the residue purified by flash chromatography (silica gel, triethylamine/ethyl acetate 1/30). 1H NMR (300 MHz, DMSO-D6) δ ppm 1.37 (m, 2 H) 1.45 (m, 4 H) 2.42 (m, 4 H) 2.85 (t, J=6.44 Hz, 2 H) 4.66 (t, J=6.61 Hz, 2 H) 7.49 (m, 1 H) 8.19 (m, 2 H) 8.91 (s, 1 H); MS (DCI/NH$_3$) m/z 275 [M+H]$^+$.

Example 6

2-[4-(benzyloxy)phenyl]-N-[2-(2-piperidin-1-yl-ethyl)-2H-indazol-4-yl]acetamide

4-Nitro-2-(2-piperidin-1-yl-ethyl)-2H-indazole (0.160 g, 0.583 mmol), iron powder (0.326 g, 5.84 mmol) and ammonium chloride (0.0185 g, 0.346 mmol) was suspended in a 4:1 ethanol/H$_2$O solution and heated to reflux for 3 hours. The mixture was cooled to room temperature, the solvents removed in vacuo and the residue stirred in triethylamine/ethyl acetate (1/4, 5 mL). The mixture was filtered through a plug of silica gel and rinsed with triethylamine/ethyl acetate (1/4) and the filtrate was concentrated to provide a pale white solid. The solid (40.0 mg, 0.164 mmol) was dissolved in 3 mL of N,N-dimethylformamide and (4-benzyloxy-phenyl)-acetic acid (0.0470 g, 0.194 mmol), PS-EDCI (1.30 mmol/g, 0.378 g, 3 equiv), N-Hydroxybenzotriazole (0.0330 g, 0.244 mmol) and diisopropylethylamine (0.0850 mL, 0.488 mmol) were added and the reaction vessel was placed on a shaker table for 6 hours. The mixture was concentrated under vacuo and the residue dissolved in 1.5 mL of a 1:1 mixture of dimethylsulfoxide/methanol and purified by preparative reverse-phase HPLC. 1H NMR (300 MHz, DMSO-D6) δ ppm 1.37 (m, 2 H) 1.46 (m, 4 H) 2.39 (m, 4 H) 2.79 (t, J=6.61 Hz, 2 H) 3.68 (s, 2 H) 4.51 (t, J=6.61 Hz, 2 H) 5.08 (s, 2 H) 6.92 (m, 2 H) 7.14 (m, 1 H) 7.39 (m, 9 H) 8.47 (m, 1 H) 10.02 (s, 1 H); MS (DCI/NH$_3$) m/z 469 [M+H]$^+$.

Example 7

2-(3-phenoxyphenyl)-N-[2-(2-piperidin-1-ylethyl)-2H-indazol-4-yl]acetamide

The title compound was prepared according to the procedure for Example 6 substituting 3-phenoxy-phenyl)-acetic acid for (4-benzyloxy-phenyl)-acetic acid. 1H NMR (300 MHz, DMSO-D6) δ ppm 1.37 (m, 2 H) 1.46 (m, 4 H) 2.38 (m, 4 H) 2.79 (t, J=6.61 Hz, 2 H) 3.75 (s, 2 H) 4.51 (t, J=6.61 Hz, 2 H) 6.88 (m, 1 H) 7.03 (m, 3 H) 7.14 (m, 3 H) 7.35 (m, 4 H) 7.50 (m, 1 H) 8.46 (m, 1 H) 10.07 (m, 1 H); MS (DCI/NH$_3$) m/z 455 [M+H]$^+$.

Example 8

4-(1,1'-biphenyl-4-yl)-4-oxo-N-[2-(2-piperidin-1-ylethyl)-2H-indazol-4-yl]butanamide

The title compound was prepared according to the procedure for Example 6 substituting 4-biphenyl-4-yl-4-oxo-butyric acid for (4-benzyloxy-phenyl)-acetic acid. 1H NMR (300 MHz, DMSO-D6) δ ppm 1.36 (m, 2 H), 1.50 (m, 4 H), 2.38 (m, 4 H), 2.82 (m, 4 H), 3.16 (m, 2 H), 4.51 (m, 2 H), 7.13 (m, 1 H), 7.28 (m, 1 H), 7.45 (m, 1 H), 7.54 (m, 3 H), 7.76 (m, 2 H), 7.86 (m, 2 H), 8.12 (m, 2 H), 8.53 (m, 1 H), 9.99 (m, 1 H); MS (DCI/NH$_3$) m/z 481 [M+H]$^+$.

Example 9

2-[4-(benzyloxy)phenyl]-N-{2-[2-(dimethylamino)ethyl]-2H-indazol-4-yl}acetamide

Example 9A dimethyl-[2-(4-nitro-indazol-2-yl)-ethyl]-amine

4-Nitroindazole (1.00 g, 6.13 mmol) was dissolved in 20 mL of N,N-dimethylformamide and potassium carbonate (2.50 g, 18.1 mmol) was added. The mixture was stirred for 30 minutes and then (2-chloro-ethyl)-dimethyl-amine hydrochloride (1.33 g 9.23 mmol) was added. The reaction mixture was heated to 60° C. for 6 hours, cooled to room temperature. The mixture was filtered through a plug of silica gel and rinsed with triethylamine/ethyl acetate (1/4). The filtrate was concentrated in vacuo to remove N,N-dimethylformamide and the residue purified by flash chromatography (silica gel, triethylamine/ethyl acetate 1/30). $^1$H NMR (300 MHz, DMSO-$d_6$) ppm 2.19 (s, 6H), 2.84 (t, 2H, J=6.44) 4.65 (t, 2H, J=6.44), 7.49 (dd, 1H, $J_1$=8.48, $J_2$=7.8), 8.18(m, 1H), 8.20 (m, 1H), 8.91 (s, 1H); MS (DCI/NH$_3$) m/z 235 [M+H]$^+$.

Example 9

2-[4-(benzyloxy)phenyl]-N-{2-[2-(dimethylamino)ethyl]-2H-indazol-4-yl}acetamide Dimethyl-[2-(4-nitro-indazol-2-yl)-ethyl]-amine (0.340 g, 1.45 mmol), iron powder (0.800 g, 14.3 mmol) and ammonium chloride (0.0385 g, 0.720 mmol) was suspended in a 4:1 ethanol/$H_2O$ solution. The mixture was heated to reflux for 3 hours, cooled to room temperature and the mixture concentrated under vacuo. The residue was taken up and stirred in triethylamine/ethyl acetate (1/4, 30 mL) for 15 minutes and then filtered through a plug of silica gel. After rinsing the plug with triethylamine/ethyl acetate (1/4), the filtrate was concentrated under reduced pressure to provide a yellow solid. The solid was used as a substitute for 2-(2-Pyrrolidin-1-yl-ethyl)-2H-indazol-4-ylamine in the procedure described in Example 1 to provide the titled compound. $^1$H NMR (300 MHz, DMSO-$d_6$) ppm 2.86 (s, 6H), 3.69 (s, 2H), 3.72 (t, 2H, J=6.24), 4.87 (t, 2H, J=6.24), 5.09 (s, 2H), 6.97 (m, 2H), 7.19–7.48 (m, 9H), 8.59 (s, 1H), 9.54 (s, 1H), 10.15 (s, 1H); MS (DCI/$NH_3$) m/z 429 [M+H]$^+$.

Example 10

N-{2-[2-(dimethylamino)ethyl]-2H-indazol-5-yl}-N'-(4-phenoxyphenyl)urea

Example 10a dimethyl-[2-(5-nitro-indazol-2-yl)-ethyl]-amine

5-Nitroindazole (1.00 g, 6.13 mmol) was dissolved in 20 mL of N,N-dimethylformamide and potassium carbonate (2.50 g, 18.1 mmol) was added. The mixture was stirred for 30 minutes and then (2-chloro-ethyl)-dimethyl-amine hydrochloride (1.32 g 9.16 mmol) was added. The reaction mixture was heated to 60° C. for 6 hours, cooled to room temperature, filtered through a plug of silica gel and rinsed with triethylamine/ethyl acetate (1/4). The filtrate was concentrated in vacuo and the residue purified by flash chromatography (silica gel, triethylamine/ethyl acetate 1/30). $^1$H NMR (300 MHz, DMSO-$d_6$) ppm 2.18 (s, 6H), 2.81 (t, 2H, J=6.44), 4.60 (t, 2H, J=6.44), 7.78 (m, 1H), 8.00 (m, 1H), 8.82 (s, 1H), 8.89 (m, 1H); MS (DCI/$NH_3$) m/z 235 [M+H]$^+$.

Example 10B

2-(2-dimethylamino-ethyl)-2H-indazol-5-ylamine

Dimethyl-[2-(5-nitro-indazol-2-yl)-ethyl]-amine (0.300 g, 1.28 mmol), iron powder (0.715 g, 12.8 mmol) and ammonium chloride (0.0343 g, 0.641 mmol) was suspended in a 4:1 ethanol/$H_2O$ solution. The mixture was heated to reflux for 3 hours, cooled to room temperature and the solvents were removed under vacuo. The residue was stirred in triethylamine/ethyl acetate (1/4, 30 mL) for 15 minutes, filtered through a plug of silica gel followed by rinsing with triethylamine/ethyl acetate (1/4). The filtrate was concentrated to provide the titled product. $^1$H NMR (300 MHz, DMSO-$d_6$) ppm 2.16 (s, 6H) 2.72 (t, 2H, J=6.44), 4.35 (t, 2H, J=6.44), 4.74 (s, 2H), 6.55 (dm, 1H), 6.72 (m, 1H), 7.30 (m, 1H), 7.89 (s, 1H); MS (DCI/$NH_3$) m/z 205 [M+H]$^+$.

Example 10

N-{2-[2-(dimethylamino)ethyl]-2H-indazol-5-yl}-N'-(4-phenoxyphenyl)urea

A mixture of 2-(2-dimethylamino-ethyl)-2H-indazol-5-ylamine (42.0 mg, 0.206 mmol), 4-phenoxyphenyl isocyanate (43.4 mg, 0.206 mmol) and 2 mL of THF, was stirred at 50° C. for 6 hours. The solvents were removed under vacuo, the residue was dissolved in 1.5 mL of a 1:1 mixture of dimethylsulfoxide/methanol and purified by preparative reverse-phase HPLC. $^1$H NMR (300 MHz, DMSO-$d_6$) ppm 2.56 (s, 8H), 4.66 (m, 2H), 6.95–7.38 (m, 10H), 7.56 (m, 1H), 7.93 (m, 1H), 8.3 (s, 1H), 8.75 (m, 2H); MS (DCI/$NH_3$) m/z 416 [M+H]$^+$.

Example 11

N-(4-phenoxyphenyl)-N'-[2-(2-pyrrolidin-1-ylethyl)-2H-indazol-5-yl]urea

Example 11A

5-nitro-2-(2-pyrrolidin-1-yl-ethyl)-2H-indazole

A mixture of 5-Nitroindazole (1.00 g, 6.13 mmol) was dissolved in 20 mL of N,N-dimethylformamide and potassium carbonate (2.50 g, 18.1 mmol) was stirred for 30 minutes after which 1-(2-chloro-ethyl)-pyrrolidine hydrochloride (1.56 g 9.17 mmol) was added. The mixture was heated to 60° C. for 6 hours, cooled to room temperature. The mixture was filtered through a plug of silica gel and rinsed with triethylamine/ethyl acetate (1/4) and the filtrate concentrated in vacuo. The residue was purified by flash chromatography (silica gel, triethylamine/ethyl acetate 1/30). $^1$H NMR (300 MHz, DMSO-$d_6$) ppm 1.64 (m, 4H), 2.48 (m, 4H), 2.99 (t, 2H, J=6.44), 4.62 (t, 2H, J=6.44), 7.78 (m, 1H), 8.00 (m, 1H), 8.83(m, 1H), 8.88 (m, 1H); MS (DCI/$NH_3$) m/z 261 [M+H]$^+$.

Example 11B

2-(2-pyrrolidin-1-yl-ethyl)-2H-indazol-5-ylamine

A mixture of 5-Nitro-2-(2-pyrrolidin-1-yl-ethyl)-2H-indazole (0.250 g, 0.961 mmol), iron powder (0.536 g, 9.60 mmol) and ammonium chloride (0.0257 g, 0.480 mmol) in a 4:1 ethanol/$H_2O$ solution was heated to reflux for 3 hours and then cooled to room temperature. The solvent was removed under vacuo and the residue stirred in triethylamine/ethyl acetate (1/4, 30 mL) for 15 minutes and then filtered through a plug of silica gel. After rinsing with triethylamine/ethyl acetate (1/4), the filtrate was concentrated unde vacuo to provide the title product. $^1$H NMR (300 MHz, DMSO-$d_6$) ppm 1.79 (s, 4H), 2.48 (m, 4H), 2.88 (s, 2H), 3.26 (m, 2H), 4.58 (m, 2H), 6.57 (m, 1H), 6.76 (m, 1H), 7.34 (m, 1H), 7.96 (s, 1H); MS (DCI/$NH_3$) m/z 231 [M+H]$^+$.

Example 11

N-(4-phenoxyphenyl)-N'-[2-(2-pyrrolidin-1-ylethyl)-2H-indazol-5-yl]urea

A mixture of 2-(2-pyrrolidin-1-yl-ethyl)-2H-indazol-5-ylamine (0.100 g, 0.434 mmol), 4-phenoxyphenyl isocyanate (0.0917 g, 0.434 mmol) and 6 mL of THF was stirred at 50° C. for 1 hour. The mixture was cooled to room temperature and the solvents removed under vacuo. The resultant solid was triturated in ether and collected by filtration to provide the titled product. 1H NMR (300 MHz, DMSO-D6) δ ppm 1.66 (m, 4 H), 2.50 (m, 4 H), 2.96 (m, 2 H), 4.48 (t, J=5.93 Hz, 2 H), 6.97 (m, 4 H), 7.11 (m, 2 H), 7.36 (m, 2 H), 7.50 (m, 3 H), 7.88 (m, 1 H), 8.26 (s, 1 H), 8.54 (s, 1 H), 8.64 (s, 1 H); MS (DCI/NH$_3$) m/z 441 [M+H]$^+$.

Example 12

N-(4-bromophenyl)-N'-[2-(2-pyrrolidin-1-ylethyl)-2H-indazol-5-yl]urea

The title compound was prepared according to the procedure for Example 11 substituting 4-bromophenyl isocyanate for 4-phenoxyphenyl isocyanate. 1H NMR (300 MHz, DMSO-D6) δ ppm 1.65 (m, 4 H) 2.47 (m, 4 H) 2.95 (t, J=6.44 Hz, 2 H) 4.48 (t, J=6.44 Hz, 2 H) 7.13 (m, 1 H) 7.44 (m, 4 H) 7.55 (m, 1 H) 7.87 (m, 1 H) 8.25 (m, 1 H) 8.58 (m, 1 H) 8.77 (m, 1 H); MS (ESI) m/z 430 [M+H]$^+$.

Example 13

N-(4'-fluoro-1,1'-biphenyl-4-yl)-N'-[2-(2-pyrrolidin-1-ylethyl)-2H-indazol-5-yl]urea The title compound was prepared according to the procedure for Example 11 substituting 4'-fluoro-4-isocyanato-biphenyl for 4-phenoxyphenyl isocyanate 1H NMR (300 MHz, DMSO-D6) δ ppm 1.83 (m, 2 H), 2.00 (m, 2 H), 3.03 (m, 2 H), 3.53 (m, 2 H), 3.81 (m, 2 H), 4.78 (t, J=6.10 Hz, 2 H), 7.15 (m, 2 H), 7.45 (m, 4 H), 7.59 (m, 2 H), 7.83 (m, 1 H), 7.96 (m, 1 H), 8.36 (m, 1 H), 8.77 (m, 1 H), 8.90 (m, 1 H), 9.49 (m, 1 H); MS (ESI) m/z 444 [M+H]$^+$.

Example 14

2-(4-phenoxyphenyl)-N-[2-(2-pyrrolidin-1-ylethyl)-2H-indazol-5-yl]acetamide

A mixture of 2-(2-pyrrolidin-1-yl-ethyl)-2H-indazol-5-ylamine (56.0 mg, 0.243 mmol), (4-benzyloxy-phenyl)-acetic acid (60.0 mg, 0.248 mmol), ethyldimethypropylcarbodiimide hydrochloride (57.0 mg, 0.298 mmol), N-hydroxybenzotriazole (40.0 mg, 0.296 mmol), N-methylmorpholine (64.0 mg, 0.633 mmol) and 2 mL of N,N-dimethylformamide, were shaken for 6 hours. The solvents were removed under vacuo and the residue was dissolved in 1.5 mL of a 1:1 mixture of dimethylsulfoxide/methanol and purified by preparative reverse-phase HPLC. $^1$H NMR (300 MHz, DMSO-d$_6$) ppm 1.82(m, 2H), 1.99 (m, 2H), 3.03(m, 2H), 3.52 (m, 2H), 3.64 (s, 2H), 3.80 (m, 2H), 4.78 (t, 2H, J=6.24), 6.97–7.00 (m, 4H), 7.12 (m, 1H), 7.29–7.39 (m, 5H), 7.59 (m, 1H), 8.18 (s, 1H), 8.38 (s, 1H), 10.13 (s, 1H); MS (DCI/NH$_3$) m/z 441 [M+H]$^+$.

Example 15

N-{2-[2-(dimethylamino)ethyl]-2H-indazol-5-yl}-2-(4-phenoxyphenyl)acetamide

A mixture of 2-(2-Dimethylamino-ethyl)-2H-indazol-5-ylamine (49.0 mg, 0.243 mmol), (4-phenoxy-phenyl)-acetic acid (60.0 mg, 0.248 mmol), EDCI (57.0 mg, 0.298 mmol), N-hydroxybenzotriazole (40.0 mg, 0.296 mmol), N-methyl morpholine (64.0 mg, 0.633 mmol) and 2 mL of N,N-dimethylformamide was shaken for 6 hours. The solvents were removed under vacuo and the residue dissolved in 1.5 mL of a 1:1 mixture of dimethylsulfoxide/methanol was purified by preparative reverse-phase HPLC. $^1$H NMR (300 MHz, DMSO-d$_6$) ppm 2.49(s, 6H) 3.34 (t, 2H, J=6.44), 3.37 (s, 2H), 4.50 (t, 2H, J=6.44), 6.69–6.74 (m, 4H), 6.85 (m, 1H), 7.03 (m, 1H), 7.08–7.13 (m, 4H), 7.32 (m, 1H), 7.90 (s, 1H), 8.10 (s, 1H), 9.26 (s, 1H); MS (DCI/NH$_3$) m/z 415 [M+H]$^+$.

Example 16

(2E)-3-[4-(benzyloxy)phenyl]-N-{2-[2-(dimethylamino)ethyl]-2H-indazol-5-yl}acrylamide The title compound was prepared according to the procedure for Example 15 substituting 3-(4-benzyloxy-phenyl)-acrylic acid for (4-phenoxy-phenyl)-acetic acid. $^1$H NMR (500 MHz, dmso-d$_6$) δ ppm 1.89 (s, 6H), 2.49 (t, 2H), 4.17 (t, 2H), 4.88 (s, 2H), 6.42 (m, 1H), 6.80 (m, 2H), 7.04 (m, 2H), 7.11 (m, 2H), 7.17 (m, 2H), 7.26 (m, 4H), 7.96 (s, 1H), 8.01 (s, 1H), 9.75 (s, 1H); MS (ESI) m/z 441 [M+H]$^+$.

Example 17

(2E)-3-(1,1'-biphenyl-4-yl)-N-{2-[2-(dimethylamino)ethyl]-2H-indazol-5-yl}acrylamide The title compound was prepared according to the procedure for Example 15 substituting (3-phenoxy-phenyl)-acetic acid for (4-phenoxy-phenyl)-acetic acid. $^1$H NMR (500 MHz, dmso-d$_6$) δ ppm 2.17 (s, 6H), 2.78 (t, 2H), 4.46 (t, 2H), 6.90 (m, 1H), 7.32 (m, 1H), 7.39 (m, 1H), 7.48 (m, 2H), 7.59 (m, 2H), 7.73 (m, 6H), 8.27 (s, 1H), 8.31 (s, 1H), 10.15 (s, 1H); MS (ESI) m/z 411 [M+H]$^+$.

Example 18

4-benzyl-N-{2-[2-(dimethylamino)ethyl]-2H-indazol-5-yl}benzamide

The title compound was prepared according to the procedure for Example 15 substituting 3-biphenyl-4-yl-acrylic acid for (4-phenoxy-phenyl)-acetic acid. $^1$H NMR (500 MHz, dmso-d$_6$) δ ppm 2.17 (s, 6H), 2.77 (t, 2H), 4.02 (s, 2H), 4.46 (t, 2H), 7.20 (m, 1H), 7.28 (m, 4H), 7.37 (m, 2H), 7.44 (m, 1H), 7.55 (m, 1H), 7.88 (m, 2H), 8.18 (m, 1H), 8.31 (s, 1H), 10.06 (s, 1H); MS (ESI) m/z 399 [M+H]$^+$.

Example 19

N-{2-[2-(dimethylamino)ethyl]-2H-indazol-5-yl}-3-phenoxybenzamide

The title compound was prepared according to the procedure for Example 15 substituting 3-phenoxy-benzoic acid for (4-phenoxy-phenyl)-acetic acid. $^1$H NMR (500 MHz, dmso-d$_6$) δ ppm 2.17 (s, 6H), 2.77 (m, 2H), 4.46 (m, 2H), 7.07 (d, 2H), 7.20 (m, 2H), 7.44 (m, 3H), 7.55 (m, 3H), 7.76 (m, 1H), 8.17 (s, 1H), 8.32 (s, 1H), 10.17 (s, 1H); MS (ESI) m/z 401 [M+H]$^+$.

Example 20

4-(4-chlorophenyl)-N-{2-[2-(dimethylamino)ethyl]-2H-indazol-5-yl}cyclohexanecarboxamide The title compound was prepared according to the procedure for Example 15 substituting 4-(4-chloro-phenyl)-cyclohexanecarboxylic acid for (4-phenoxy-phenyl)-acetic acid. $^1$H NMR (500 MHz, dmso-d$_6$) δ ppm 1.47 (m, 2H), 1.63 (m, 2H), 1.89 (m, 2H), 1.96 (m, 2H), 2.42 (m, 1H), 2.57 (m, 1H), 2.84 (s, 6H), 3.72 (m, 2H), 4.81 (t, 2H), 7.32 (m, 5H), 7.57 (m, 1H), 8.20 (s, 1H), 8.38 (s, 1H), 9.82 (s, 1H); MS (ESI) m/z 425 [M+H]$^+$.

Example 21

N-{2-[2-(dimethylamino)ethyl]-2H-indazol-5-yl}-2-(3-phenoxyphenyl)acetamide

The title compound was prepared according to the procedure for Example 15 substituting (3-phenoxy-phenyl)-acetic acid for (4-phenoxy-phenyl)-acetic acid. $^1$H NMR (500 MHz, dmso-d$_6$) δ ppm 2.84 (s, 6H), 3.64 (s, 2H), 3.71 (t, 2H), 4.81 (m, 2H), 6.89 (m, 1H), 7.02 (m, 3H), 7.14 (m, 2H), 7.28 (m, 1H), 7.34 (m, 1H), 7.39 (m, 2H), 7.58 (m, 1H), 8.15 (d, 1H), 8.38 (s, 1H), 10.11 (s, 1H); MS (ESI) m/z 415 [M+H]$^+$.

Example 22

2-(4-phenoxyphenyl)-N-[2-(2-piperidin-1-ylethyl)-2H-indazol-5-yl]acetamide

Example 22A

5-Nitro-2-(2-piperidin-1-yl-ethyl)-2H-indazole

A mixture of 5-Nitroindazole (1.00 g, 6.13 mmol) and and potassium carbonate (2.50 g, 18.1 mmol) in 20 mL of N,N-dimethylformamide was stirred for 30 minutes and then 1-(2-chloro-ethyl)-piperidine hydrochloride (1.74 g 9.45 mmol) was added. The mixture was heated to 60° C. for 6 hours, cooled to room temperature, filtered through a plug of silica gel and rinsed with triethylamine/ethyl acetate (1/4). The filtrate was concentrated under vacuo and the residue purified by flash chromatography (silica gel, triethylamine/ethyl acetate 1/30). $^1$H NMR (300 MHz, DMSO-d$_6$) ppm 1.13–1.15 (m, 6H) 2.40 (m, 4H), 2.82 (t, 2H, J=6.44) 4.61 (t, 2H, J=6.44), 7.78 (m, 1H), 8.00 (m, 1H), 8.81 (s, 1H), 8.90 (d, 1H); MS (DCI/NH$_3$) m/z 275 [M+H]$^+$.

Example 22B

2-(2-piperidin-1-yl-ethyl)-2H-indazol-5-ylamine

5-Nitro-2-(2-pyrrolidin-1-yl-ethyl)-2H-indazole (0.325 g, 1.18 mmol), iron powder (0.659 g, 11.8 mmol) and ammonium chloride (0.0317 g, 0.592 mmol) was suspended in a 4:1 ethanol/H$_2$O solution and heated to reflux for 3 hours. The mixture was cooled to room temperature, the solvent were removed in vacuo and the residue stirred in triethylamine/ethyl acetate (1/4, 30 mL) for 15 minutes. The mixture was filtered through a plug of silica gel, rinsed with triethylamine/ethyl acetate (1/4) and the filtrate was concentrated to afford the title product. $^1$H NMR (300 MHz, DMSO-d$_6$) ppm 1.31–1.52 (m, 6H) 2.40 (m, 4H), 2.78 (m, 2H), 4.38 (t, 2H, J=6.78), 4.79 (s, 2H), 6.55 (m, 1H), 6.72 (m, 1H), 7.29 (s, 1H), 7.89 (s, 1H); MS (DCI/NH$_3$) m/z 245 [M+H]$^+$.

Example 22

2-(4-phenoxyphenyl)-N-[2-(2-piperidin-1-ylethyl)-2H-indazol-5-yl]acetamide

The titled compound was prepared according to the procedure described in Example 5 substituting 2-(2-Piperidin-1-yl-ethyl)-2H-indazol-5-ylamine for 2-(2-Pyrrolidin-1-yl-ethyl)-2H-indazol-4-ylamine. $^1$H NMR (300 MHz, DMSO-d$_6$) ppm 1.33–1.82(m, 8H) 2.92 (m, 2H), 3.27 (m, 2H), 3.64 (s, 2H), 4.79 (m, 2H), 6.97–7.00 (m, 4H), 7.12 (m, 1H), 7.28 (m, 1H), 7.35–7.40 (m, 4H), 7.57 (m, 1H), 8.16 (s, 1H), 8.35 (s, 1H), 10.10 (s, 1H); MS (DCI/NH$_3$) m/z 455 [M+H]$^+$.

Example 23

N-(4-phenoxyphenyl)-N'-[2-(2-piperidin-1-ylethyl)-2H-indazol-5-yl]urea

The titled compound was prepared according to the procedure described in Example 22 substituting 2-(2-piperidin-1-yl-ethyl)-2H-indazol-5-ylamine for 2-(2-dimethylamino-ethyl)-2H-indazol-5-ylamine. $^1$H NMR (300 MHz, DMSO-d$_6$) ppm 1.33–1.82(m, 6H), 2.97(m, 2H), 3.27 (m, 2H), 3.70 (m, 2H), 4.82 (d, 2H, J=6.45), 6.94–7.00 (m, 4H), 7.06–7.12 (m, 1H), 7.18 (m, 1H), 7.34–7.39 (m, 2H), 7.48 (m, 2H), 7.57 (m, 1H), 7.96 (m, 1H), 8.35 (s, 1H), 8.69 (s, 1H), 8.75 (s, 1H), 9.22 (s, 1H); MS (DCI/NH$_3$) m/z 456 [M+H]$^+$.

Example 24

N-[2-(2-azepan-1-ylethyl)-2H-indazol-5-yl]-N'-(4-phenoxyphenyl)urea

Example 24A

2-(2,2-dimethoxyethyl)-5-nitro-2H-indazole

To mixture of 3.00 g (18.4 mmol) of 5-nitroindazole and 5.08 g (36.9 mmol) of K$_2$CO$_3$ in 61 mL of N,N-dimethylformamide and was added 3.42 g (20.2 mmol) of 2-bromo-1,1-dimethoxy-ethane. The mixture was heated to 55° C. and allowed to stir for 12 hours. The reaction mixture was cooled to room temperature and the contents filtered through a bed of celite. The filtrate was then concentrated under reduced pressure and the residue purified via column chromatography (30–80% ethyl acetate/hexanes) to provide 1.08 g of the title product. 1H NMR (400 MHz, DMSO-D6) δ ppm 3.31 (s, 6 H), 4.67 (d, J=5.49 Hz, 2 H), 4.91 (t, J=5.42 Hz, 1 H), 7.81 (m, 1.92 Hz, 1 H), 7.98 (m, 1 H), 8.62 (m, 2 H); MS (DCI/NH$_3$) m/z 252 [M+H]$^+$.

Example 24B

2-(2,2-dimethoxyethyl)-2H-indazol-5-amine

A mixture of 1.00 g (3.98 mmol) of Example 24A, 0.105 g of NH4Cl (1.98 mmol) in 34.5 mL of 80% EtOH. was added 2.19 g (39.2 mmol) of Fe. The mixture was heated to reflux for 1 hour and the reaction mixture cooled to room temperature. The mixture was concentrated under reduced pressure and the residue taken up in 10:1 ethyl acetate:triethylamine and filtered through a plug of silica gel eluting additional eluent. Concentration under reduced pressure provided 0.900 mg of a pale yellow oil. 1H NMR (300 MHz, DMSO-D6) δ ppm 3.27 (s, 6 H), 4.38 (d, J=5.76 Hz, 2 H), 4.81 (m, 5.43 Hz, 3 H), 6.56 (m, 1 H), 6.75 (m, 2.03 Hz, 1 H), 7.33 (m, 1 H), 7.87 (s, 1 H); MS (DCI/NH$_3$) m/z 222 [M+H]$^+$.

Example 24C

N-[2-(2,2-dimethoxyethyl)-2H-indazol-5-yl]-N'-(4-phenoxyphenyl)urea

A mixture of 0.600 g of 24B (2.71 mmol) and 0.573 g of 4-phenoxyphenyl isocyanate in 36 mL of THF was heated to 60° C. for 1 hour. The mixture was cool to room temperature and concentrated under reduced pressure to provide a brown solid. The residue was triturated from boiling ether to provide 1.10 g of the title product. 1H NMR (300 MHz, DMSO-D6) δ ppm 3.29 (s, 6 H), 4.48 (d, J=5.42 Hz, 2 H), 4.86 (m, 1 H), 6.96 (m, 4 H), 7.12 (m, 2 H), 7.35 (m, 2 H), 7.51 (m, 3 H), 7.88 (m, 1 H), 8.21 (m, 1 H), 8.57 (m, 1 H), 8.66 (m, 1 H); MS (ESI) m/z 433 [M+H]$^+$.

Example 24

N-[2-(2-azepan-1-ylethyl)-2H-indazol-5-yl]-N'-(4-phenoxyphenyl)urea

A mixture of 0.750 g of Example 24C (1.74 mmol) and 8 mL of 2 N HCl in 8 mL of THF was heated to 60° C. for 6 hours after which the solvents were removed under vacuo. The residue taken up in toluene followed by concentration under vacuo three times. The residue, 40.0 mg (0.104 mmol) was taken up in 1.5 mL of 1:1 dichloroethane/methanol (1% acetic acid) and 12.9 mg (0.130 mmol) of hexamethyleneimine was added, followed by 0.155 g of macroporous cyanoborohydride resin (2.1 mmol/g, 3 equiv). The reaction mixture was shaken at 40° C. for 3 hours, cool to room temperature and filtered. The filtrate was concentrated under reduced pressure to provide a residue that was purified by preparative HPLC to provide the titled product. 1H NMR (300 MHz, DMSO-D6) δ ppm 1.61 (m, 4 H), 1.82 (m, 4 H), 3.21 (m, 2 H), 3.41 (m, 2 H), 3.76 (m, 2 H), 4.81 (m, 2 H), 6.97 (m, 4 H), 7.09 (m, 1 H), 7.18 (m, 1 H), 7.36 (m, 2 H), 7.48 (m, 2 H), 7.57 (m, 1 H), 7.97 (m, 1 H), 8.33 (m, 1 H), 8.63 (m, 2 H); MS (ESI) m/z 470 [M+H]$^+$.

Example 25

N-{2-[2-(4-methylpiperidin-1-yl)ethyl]-2H-indazol-5-yl}-N'-(4-phenoxyphenyl)urea The title compound was prepared according to the procedure for Example 24 substituting 4-methylpiperidine for hexamethyleneimine. 1H NMR (300 MHz, DMSO-D6) δ ppm 0.91 (d, J=6.44 Hz, 3 H), 1.30 (m, 2 H), 1.58 (m, 1 H), 1.80 (m, 2 H), 2.96 (m, 2 H), 3.52 (m, 2 H), 3.71 (m, 2 H), 4.82 (m, 2 H), 6.97 (m, 4 H), 7.09 (m, 1 H), 7.17 (m, 1 H), 7.36 (m, 2 H), 7.48 (m, 2 H), 7.58 (m, 1 H), 7.96 (m, 1 H), 8.35 (m, 1 H), 8.64 (m, 2 H); MS (ESI) m/z 470 [M+H]$^+$.

Example 26

N-{2-[2-(3-methylpiperidin-1-yl)ethyl]-2H-indazol-5-yl}-N'-(4-phenoxyphenyl)urea The title compound was prepared according to the procedure for Example 24 substituting 3-methylpiperidine for hexamethyleneimine. 1H NMR (300 MHz, DMSO-D6) δ ppm 0.89 (d, J=6.44 Hz, 3 H), 1.05 (m, 1 H), 1.71 (m, 2 H), 1.84 (m, 2 H), 2.63 (m, 1 H), 2.85 (m, 1 H), 3.20 (m, 1 H), 3.50 (m, 1 H), 3.69 (m, 2 H), 4.82 (m, 2 H), 6.97 (m, 4 H), 7.09 (m, 1 H), 7.18 (m, 1 H), 7.37 (m, 2 H), 7.48 (m, 2 H), 7.58 (m, 1 H), 7.97 (m, 1 H), 8.36 (m, 1 H), 8.67 (m, 2 H); MS (ESI) m/z 470 [M+H]$^+$.

Example 27

N-{2-[2-(2-methylpyrrolidin-1-yl)ethyl]-2H-indazol-5-yl}-N'-(4-phenoxyphenyl)urea The title compound was prepared according to the procedure for Example 24 substituting 2-methlypyrrolidine for hexamethyleneimine. 1H NMR (300 MHz, DMSO-D6) δ ppm 1.34 (d, J=6.44 Hz, 3 H), 1.57 (m, 1 H), 1.94 (m, 2 H), 2.19 (m, 1 H), 3.07 (m, 1 H), 3.52 (m, 2 H), 3.64 (m, 1 H), 3.95 (m, 1 H), 4.79 (m, 2 H), 6.97 (m, 4H), 7.08 (m, 1 H), 7.18 (m, 1 H), 7.36 (m, 2 H), 7.48 (m, 2 H), 7.58 (m, 1 H), 7.96 (m, 1 H), 8.36 (m, 1 H), 8.63 (m, 2 H); MS (ESI) m/z 456 [M+H]$^+$.

Example 28

N-(2-{2-[(2S)-2-(methoxymethyl)pyrrolidin-1-yl]ethyl}-2H-indazol-5-yl)-N'-(4-phenoxyphenyl)urea The title compound was prepared according to the procedure for Example 24 substituting (S)-2-methoxymethylpyrrolidine for hexamethyleneimine. 1H NMR (300 MHz, DMSO-D6) δ ppm 1.71 (m, 1 H), 1.86 (m, 1 H), 1.99 (m, 1 H), 2.13 (m, 1 H), 3.13 (m, 2 H), 3.38 (m, 3 H), 3.55 (m, 2 H), 3.66 (m, 1 H), 3.79 (m, 1 H), 3.97 (m, 1 H), 4.79 (m, 2 H), 6.94 (m, 4 H), 7.09 (m, 1 H), 7.18 (m, 1 H), 7.36 (m, 2 H), 7.48 (m, 2 H), 7.58 (m, 1 H), 7.96 (m, 1 H), 8.33 (m, 1 H), 8.64 (m, 2 H); MS (ESI) m/z 486 [M+H]$^+$.

Example 29

1-{2-[5-({[(4-phenoxyphenyl)amino]carbonyl}amino)-2H-indazol-2-yl]ethyl}piperidine-4-carboxamide The title compound was prepared according to the procedure for Example 24 substituting piperidine 4-carboxylic-acid amide for hexamethyleneimine. 1H NMR (300 MHz, DMSO-D6) δ ppm 1.73 (m, 2 H), 1.92 (m, 2 H), 2.32 (m, 1 H), 2.93 (m, 2 H), 3.59 (m, 2 H), 3.72 (m, 2 H), 4.79 (m, 2 H), 6.98 (m, 5 H) 7.09 (m, 1H) 7.38 (m, 3 H) 7.47 (m, 3 H) 7.67 (m, 1 H) 7.95 (m, 1 H) 8.10 (s, 1 H) 8.75 (s, 2 H); MS (ESI) m/z 499 [M+H]$^+$.

Example 30

N-[2-(2-azetidin-1-ylethyl)-2H-indazol-5-yl]-N'-(4-phenoxyphenyl)urea

The title compound was prepared according to the procedure for Example 24 substituting azetidine for hexamethyleneimine. $^1$H NMR (500 MHz, pyridine-d$_5$) δ ppm 2.07 (m, 2H), 3.64 (m, 6H), 4.72 (t, 2H), 7.08 (m, 5H), 7.32 (m, 2H), 7.75 (m, 2H), 8.02 (m, 2H), 8.14 (s, 1H), 8.51 (s, 1H), 9.96 (s, 1H), 10.03 (s, 1H); MS (ESI) m/z 428 [M+H]$^+$.

Example 31

N-(2-{2-[isobutyl(methyl)amino]ethyl}-2H-indazol-5-yl)-N'-(4-phenoxyphenyl)urea

The title compound was prepared according to the procedure for Example 24 substituting isobutyl-methyl-amine for hexamethyleneimine. $^1$H NMR (500 MHz, pyridine-d$_5$) δ ppm 0.76 (d, 6H), 1.59 (m, 1H), 2.04 (d, 2H), 2.17 (s, 3H), 2.93 (t, 2H), 4.52 (t, 2H), 7.09 (m, 5H), 7.33 (m, 2H), 7.56 (m, 1H), 7.87 (m, 1H), 7.90 (m, 2H), 8.13 (s, 1H), 8.57 (m, 1H), 9.42 (s, 1H), 9.50 (s, 1H); MS (ESI) m/z 458 [M+H]$^+$.

Example 32

N-{2-[2-(3-hydroxypyrrolidin-1-yl)ethyl]-2H-indazol-5-yl}-N'-(4-phenoxyphenyl)urea The title compound was prepared according to the procedure for Example 24 substituting 3-pyrrolidin-3-ol for hexamethyleneimine. $^1$H NMR (500 MHz, pyridine-d$_5$) δ ppm 1.96 (m, 1H), 2.13 (m, 1H), 2.85 (m, 1H), 3.10 (m, 3H), 3.44 (m, 2H), 4.59 (m, 1H), 4.73 (t, 2H), 7.08 (m, 5H), 7.33 (m, 2H), 7.68 (m, 1H), 7.79 (m, 1H), 7.99 (m, 2H), 8.14 (s, 1H), 8.51 (m, 1H), 9.77 (s, 1H), 9.85 (s, 1H); MS (ESI) m/z 458 [M+H]$^+$.

Example 33

N-(2-{2-[isopropyl(methyl)amino]ethyl}-2H-indazol-5-yl)-N'-(4-phenoxyphenyl)urea The title compound was prepared according to the procedure for Example 24 substituting isopropyl-methyl-amine for hexamethyleneimine. $^1$H NMR (500 MHz, pyridine-d$_5$) δ ppm 0.95 (d, 6H), 2.35 (s, 3H), 3.02 (m, 1H), 3.22 (t, 2H), 4.69 (t, 2H), 7.09 (m, 5H), 7.33 (m, 2H), 7.66 (m, 1H), 7.82 (m, 1H), 7.96 (m, 2H), 8.13 (s, 1H), 8.55 (m, 1H), 9.68 (s, 1H), 9.75 (s, 1H); MS (ESI) m/z 444 [M+H]$^+$.

Example 34

N-((2S)-1-{2-[5-({[(4-phenoxyphenyl)amino]carbonyl}amino)-2H-indazol-2-yl]ethyl}pyrrolidin-2-yl)acetamide The title compound was prepared according to the procedure for Example 24 substituting N-pyrrolidin-2-yl-acetamide for hexamethyleneimine. 1H NMR (500 MHz, PYRIDINE-D5) δ ppm 1.79 (m, 1 H) 2.01 (s, 3 H) 2.18 (m, 1 H) 2.50 (m, 1 H) 2.96 (m, 2H) 3.03 (m, 1 H) 3.27 (m, 2 H) 4.62 (m, 2 H) 4.68 (m, 1 H) 7.08 (m, 5 H) 7.32 (m, 2 H) 7.74 (m, 1 H) 7.81 (m, 1 H) 8.05 (m, 3 H) 8.55 (m, 1 H) 8.66 (m, 1 H) 9.96 (m, 2 H); MS (ESI) m/z 499 [M+H]$^+$.

Example 35

N-(2-{2-[(2S)-2-(hydroxymethyl)pyrrolidin-1-yl]ethyl}-2H-indazol-5-yl)-N'-(4-phenoxyphenyl)urea The title compound was prepared according to the procedure for Example 24 substituting (S)-pyrrolidin-2-yl-methanol for hexamethyleneimine. $^1$H NMR (500 MHz, pyridine-d$_5$) δ ppm 1.73 (m, 3H), 1.91 (m, 1H), 2.61 (m, 1H), 3.21 (m, 1H), 3.38 (m, 1H), 3.46 (m, 1H), 3.85 (d, 2H), 3.97 (m, 1H), 4.79 (m, 2H), 7.09 (m, 5H), 7.33 (m, 2H), 7.72 (m, 1H), 7.79 (m, 1H), 8.01 (m, 2H), 8.13 (s, 1H), 8.54 (m, 1H), 9.89 (s, 1H), 9.97 (s, 1H); MS (ESI) m/z 472 [M+H]$^+$.

Example 36

N-(2-{2-[(3R)-3-hydroxypiperidin-1-yl]ethyl}-2H-indazol-5-yl)-N'-(4-phenoxyphenyl)urea The title compound was prepared according to the procedure for Example 24 substituting (R)-piperidin-3-ol for hexamethyleneimine. $^1$H NMR (500 MHz, pyridine-d$_5$) δ ppm 1.49 (m, 2H), 1.66 (m, 1H), 1.98 (m, 1H), 2.16 (m, 1H), 2.40 (d, 1H), 2.69 (d, 1H), 3.07 (t, 2H), 3.20 (m, 1H), 3.99 (m, 1H), 4.61 (t, 2H), 7.09 (m, 5H), 7.33 (m, 2H), 7.58 (m, 1H), 7.83 (m, 1H), 7.94 (m, 2H), 8.12 (s, 1H), 8.53 (m, 1H), 9.53 (s, 1H), 9.61 (s, 1H); MS (ESI) m/z 472 [M+H]$^+$.

Example 37

N-{2-[2-(2-methylpiperidin-1-yl)ethyl]-2H-indazol-5-yl}-N'-(4-phenoxyphenyl)urea The title compound was prepared according to the procedure for Example 24 substituting 2-methyl-piperidine for hexamethyleneimine. $^1$H NMR (500 MHz, pyridine-d$_5$) δ ppm 1.01 (d, 3H), 1.23 (m, 2H), 1.48 (m, 4H), 2.34 (m, 1H), 2.51 (m, 1H), 2.91 (m, 1H), 3.08 (m, 1H), 3.42 (m, 1H), 4.64 (t, 2H), 7.09 (m, 5H), 7.33 (m, 2H), 7.62 (m, 1H), 7.84 (m, 1H), 7.94 (m, 2H), 8.14 (s, 1H), 8.55 (m, 1H), 9.55 (d, 1H), 9.63 (s, 1H); MS (ESI) m/z 470 [M+H]$^+$.

Example 38

1-{2-[5-({[(4-phenoxyphenyl)amino]carbonyl}amino)-2H-indazol-2-yl]ethyl}piperidine-3-carboxamide The title compound was prepared according to the procedure for Example 24 substituting piperidine 3-carboxylic-acid amide for hexamethyleneimine. $^1$H NMR (500 MHz, pyridine-d$_5$) δ ppm 2.02 (s, 3H), 2.32 (m, 4H), 2.88 (t, 2H), 3.24 (m, 2H), 3.63 (m, 2H), 4.54 (t, 2H), 7.09 (m, 5H), 7.33 (m, 2H), 7.60 (m, 1H), 7.87 (m, 1H), 7.93 (m, 2H), 8.14 (s, 1H), 8.58 (m, 1H), 9.50 (s, 1H), 9.56 (s, 1H); MS (ESI) m/z 499 [M+H]$^+$.

Example 39

N-{2-[2-(3,3-difluoropiperidin-1-yl)ethyl]-2H-indazol-5-yl}-N'-(4-phenoxyphenyl)urea The title compound was prepared according to the procedure for Example 24 substituting 3,3'-diflouro-piperidine for hexamethyleneimine. $^1$H NMR (500 MHz, pyridine-d$_5$) δ ppm 1.55 (m, 2H), 1.79 (m, 2H), 2.33 (m, 2H), 2.76 (t, 2H), 2.99 (t, 2H), 4.55 (t, 2H), 7.09 (m, 5H), 7.33 (m, 2H), 7.61 (m, 1H), 7.85 (m, 1H), 7.94 (m, 2H), 8.13 (s, 1H), 8.54 (m, 1H), 9.55 (s, 1H), 9.63 (s, 1H); MS (ESI) m/z 492 [M+H]$^+$.

Example 40

N-{2-[2-(4-hydroxypiperidin-1-yl)ethyl]-2H-indazol-5-yl}-N'-(4-phenoxyphenyl)urea The title compound was prepared according to the procedure for Example 24 substituting 4-piperidin-4-ol for hexamethyleneimine. $^1$H NMR (500 MHz, pyridine-d$_5$) δ ppm 1.87 (m, 2H), 2.07 (m, 2H), 2.65 (d, 2H), 3.17 (m, 2H), 3.37 (t, 2H), 3.95 (m, 1H), 4.80 (t, 2H), 7.09 (m, 5H), 7.33 (m, 3H), 7.71 (m, 1H), 7.81 (m, 1H), 8.01 (m, 2H), 8.15 (s, 1H), 8.55 (m, 1H), 9.84 (s, 1H), 9.92 (s, 1H); MS (ESI) m/z 472 [M+H]$^+$.

Example 41

N-{2-[2-(cyclohexylamino)ethyl]-2H-indazol-5-yl}-N-(4-phenoxyphenyl)urea

A solution of 0.750 g of Example 24C (1.74 mmol) and 8 mL of 2 N HCl in 8 mL of THF was heated to 60° C. for 6 hours after which the solvents were removed under vacuo and the residue taken up in toluene and concentrated under vacuo three times. The residue, 30.0 mg (0.078 mmol), cyclohexylamine (12 mg, 0.12 mmol) and BP-CNBH$_3$ (0.16 mmol) in 2 mL of methanol was heated to 50° C. for 6 hours after which the solvents were removed under reduced pressure. The residue was dissolved in 1.5 mL of a 1:1 mixture of dimethylsulfoxide/methanol and purified by preparative reverse-phase HPLC. $^1$H NMR (300 MHz, DMSO-d$_6$) ppm 1.03–1.30 (m, 5H) 1.59 (m, 1H), 1.75 (m, 2H), 2.0 (m, 2H), 3.04 (m, 1H), 3.56 (m, 2H), 4.70 (t, 2H, J=6.11), 6.95–6.99 (m, 4H), 7.09 (m, 1H), 7.20 (m, 1H), 7.36 (m, 2H), 7.58 (m, 2H), 7.97 (m, 1H), 8.32 (s, 1H), 8.60 (s, 2H), 8.84 (s, 1H), 8.90 (s, 1H); MS (DCI/NH$_3$) m/z 470 [M+H]$^+$.

Example 42

N-{2-[2-(cyclopentylamino)ethyl]-2H-indazol-5-yl}-N'-(4-phenoxyphenyl)urea

The titled compound was prepared according to the procedure described in Example 41 substituting cyclopentylamine for cyclohexylamine. $^1$H NMR (300 MHz, DMSO-d$_6$) ppm 1.50–1.72 (m, 6H), 1.96 (m, 2H), 3.55 (m, 2H), 4.70 (t, 2H, J=6.24), 6.95–6.99 (m, 3H), 7.00 (m, 1H), 7.20 (m, 1H7.36 (m, 2H), 7.49 (m, 2H), 7.58 (m, 1H,), 7.97 (m, 1H), 8.31 (s, 1H), 8.68 (s, 2H), 8.77 (s, 1H), 8.83 (s, 1H); MS (DCI/NH$_3$) m/z 456 [M+H]$^+$.

Example 43

N-(2-{2-[cyclohexyl(methyl)amino]ethyl}-2H-indazol-5-yl)-N'-(4-phenoxyphenyl)urea The titled compound was prepared according to the procedure described in Example 41 substituting cyclohexylmethyl-amine for cyclohexylamine. $^1$H NMR (300 MHz, DMSO-d$_6$) ppm 1.04–1.11 (m, 1H) 1.22 (m, 2H), 1.41 (m, 2H), 1.58 (d, 1H, J=12.57), 1.78 (m, 2H), 1.92 (m, 2H), 2.77 (s, 3H), 3.25 (t, 2H, J=11.74), 3.85 (m, 2H), 4.85 (m, 2H), 6.95–6.99 (m, 4H), 7.00 (t, 1H, J=7.48), 7.21 (m, 1H), 7.36 (m, 2H), 7.49 (d, 2H, J=9.05), 7.57 (m, 1H), 7.97 (m, 1H), 8.79 (s, 1H), 8.36 (s, 1H), 8.84 (s, 1H), 9.35 (s, 1H); MS (DCI/NH$_3$) m/z 484 [M+H]$^+$.

Example 44

N-{2-[2-(1,4-dioxa-8-azaspiro[4.5]dec-8-yl)ethyl]-2H-indazol-5-yl}-N'-(4-phenoxyphenyl)urea The titled compound was prepared according to the procedure described in Example 41 substituting 1,4-Dioxa-8-aza-spiro[4.5]decane for cyclohexylamine. $^1$H NMR (300 MHz, DMSO-d$_6$) ppm 1.90 (m, 4H) 3.15 (m, 1H), 3.70 (m, 3H), 3.80 (t, 2H, J=6.40), 3.93 (s, 4H), 4.83 (t, 2H, J=6.40), 6.95–7.00 (m, 4H), 7.00 (m, 1H), 7.20 (m, 1H), 7.36 (m, 2H), 7.49 (m, 2H), 7.58 (m, 1H), 7.97 (m, 1H), 8.34 (s, 1H), 8.80 (s, 1H), 8.86 (s, 1H); MS (DCI/NH$_3$) m/z 514 [M+H]$^+$.

Example 45

N-{2-[2-(2,6-dimethylmorpholin-4-yl)ethyl]-2H-indazol-5-yl}-N'-(4-phenoxyphenyl)urea The titled compound was prepared according to the procedure described in Example 41 substituting 2,6-Dimethyl-morpholine for cyclohexylamine. $^1$H NMR (300 MHz, DMSO-d$_6$) ppm 1.12 (d, 6H, J=6.55), 2.68 (m, 2H), 3.59 (m, 4H), 3.81 (m, 2H), 4.83 (t, 2H, J=6.24), 6.95–6.99 (m, 4H), 7.00 (m, 1H), 7.20 (m, 1H), 7.36 (m, 2H), 7.49 (m, 2H), 7.57 (m, 1H), 7.96 (m, 1H), 8.34 (s, 1H), 8.77 (s, 1H), 8.82 (s, 1H); MS (DCI/NH$_3$) m/z 486 [M+H]$^+$.

Example 46

N-{2-[2-(2,6-dimethylmorpholin-4-yl)ethyl]-2H-indazol-5-yl}-N'-(4-phenoxyphenyl)urea The titled compound was prepared according to the procedure described in Example 41 substituting 3,5-Dimethyl-piperidine for cyclohexylamine. $^1$H NMR (300 MHz, DMSO-d$_6$) ppm 0.75–0.83 (m, 1H) 0.88 (d, 6H, J=6.55), 1.15 (m, 1H), 1.74 (d, 1H, J=12.57), 1.86 (m, 1H), 2.54 (m, 2H), 3.44 (m, 2H), 3.68 (m, 2H), 4.85 (t, 2H, J=6.24), 6.95–6.99 (m, 4H), 7.09 (m, 1H), 7.20 (m, 1H), 7.36 (m, 2H), 7.49 (m, 2H), 7.57 (m, 1H), 7.96 (m, 1H), 8.34 (s, 1H), 8.76(s, 1H), 8.82 (s, 1H); MS (DCI/NH$_3$) m/z 484 [M+H]$^+$.

Example 47

2-[4-(benzyloxy)phenyl]-N-[2-(2-pyrrolidin-1-yl-ethyl)-2H-indazol-6-yl]acetamide

Example 47A 6-nitro-2-(2-pyrrolidin-1-yl-ethyl)-2H-indazole

6-Nitroindazole (2.00 g, 12.3 mmol) was treated with potassium carbonate (5.00 g 36.2 mmol) in N,N-dimethylformamide (40 mL) for 30 minutes and then 1-(2-chloroethyl)-pyrrolidine hydrochloride (3.20 g 18.8 mmol) was added. The reaction mixture was heated to 60° C. for 6 hours, then cooled to room temperature. The reaction mixture was filtered through a plug of silica gel and rinsed with triethylamine/ethyl acetate (1/4). The filtrate was concentrated in vacuo and purified by flash chromatography (silica gel, triethylamine/ethyl acetate 1/30) to afford the title compound. $^1$H NMR (300 MHz, DMSO-d$_6$) ppm 1.65 (m, 4H) 2.48 (m, 4H), 3.00 (t, 2H, J=6.44), 4.64 (t, 2H, J=6.44), 7.80 (m, 1H), 7.97 (m, 1H), 8.62 (s, 1H), 8.68 (s, 1H); MS (DCI/NH$_3$) m/z 261 [M+H]$^+$.

Example 47

2-[4-(benzyloxy)phenyl]-N-[2-(2-pyrrolidin-1-yl-ethyl)-2H-indazol-6-yl]acetamide 6-Nitro-1-(2-pyrrolidin-1-yl-ethyl)-1H-indazole (0.800 g, 3.07 mmol), iron powder (1.72 g, 30.7 mmol) and ammonium chloride (0.0822 g, 1.54 mmol) were suspended in a 4:1 solution of ethanol/$H_2O$. The reaction mixture was heated to reflux for 3 hours and then cooled to room temperature. The solvent was removed in vacuo and the residue stirred in Triethylamine/ethyl acetate (1/4, 30 mL) for 15 min and then filtered through a plug of silica gel. After rinsing with Triethylamine/ethyl acetate (1/4), the filtrate was concentrated to afford an oily solid. The titled compound was then prepared according to the procedure described in Example 1 substituting 2-(2-Pyrrolidin-1-yl-ethyl)-2H-indazol-6-ylamine for 2-(2-pyrrolidin-1-yl-ethyl)-2H-indazol-4-ylamine. $^1$H NMR (300 MHz, DMSO-$d_6$) ppm 1.64 (m, 4H), 2.46 (m, 4H), 2.93 (t, 2H, J=6.44), 3.56 (s, 2H), 4.46 (t, 2H, J=6.44), 5.09 (s, 2H), 6.97 (m, 2H), 7.06 (m, 1H), 7.26 (m, 2H), 7.31–7.48 (m, 5H), 7.59 (m, 2H), 8.03 (s, 1H), 9.28 (s, 1H); MS (DCI/$NH_3$) m/z 455 [M+H]$^+$.

Example 48

2-[4-(benzyloxy)phenyl]-N-{2-[2-(dimethylamino)ethyl]-2H-indazol-6-yl}acetamide

Example 48A dimethyl-[2-(6-nitro-indazol-2-yl)-ethyl]-amine

5-Nitroindazole (1.00 g, 6.13 mmol) was dissolved in 20 mL of N,N-dimethylformamide and potassium carbonate (2.50 g, 18.1 mmol) was added. The mixture was stirred for 30 minutes and then (2-chloro-ethyl)-dimethyl-amine hydrochloride (1.33 g 9.23 mmol) was added. The reaction mixture was heated to 60° C. for 6 hours, then cooled to room temperature. The reaction mixture was filtered through a plug of silica gel and rinsed with triethylamine/ethyl acetate (1/4). The filtrate was concentrated in vacuo to remove N,N-dimethylformamide and the residue purified by flash chromatography (silica gel, triethylamine/ethyl acetate 1/30). $^1$H NMR (300 MHz, DMSO-$d_6$) ppm 2.18 (s, 6H), 2.82 (t, 2H, J=6.44), 4.63 (t, 2H, J=6.44), 7.80 (m, 1H), 7.98 (m, 1H), 8.62 (s, 1H), 8.65 (m, 1H); MS (DCI/$NH_3$) m/z 235 [M+H]$^+$.

Example 48B

2-(2-pyrrolidin-1-yl-ethyl)-2H-indazol-6-ylamine

Dimethyl-[2-(5-nitro-indazol-2-yl)-ethyl]-amine (0.275 g, 1.17 mmol), iron powder (0.656 g, 11.7 mmol) and ammonium chloride (0.0314 g, 0.587 mmol) was suspended in a 4:1 ethanol/$H_2O$ solution. The reaction mixture was heated to reflux for 3 hours and then cooled to room temperature. The solvent was removed in vacuo and the residue stirred in triethylamine/ethyl acetate (1/4, 30 mL) for 15 minutes and then filtered through a plug of silica gel. After rinsing with triethylamine/ethyl acetate (1/4), the filtrate was concentrated to provide the title product. $^1$H NMR (300 MHz, DMSO-$d_6$) ppm 2.16 (s, 6H), 2.71 (t, 2H, J=6.44), 4.31 (t, 2H, J=6.44), 4.98 (s, 2H), 6.46 (m, 1H), 6.50 (m, 1H), 7.33 (s, 1H), 8.03 (s, 1H); MS (DCI/$NH_3$) m/z 205 [M+H]$^+$.

Example 48

2-[4-(benzyloxy)phenyl]-N-{2-[2-(dimethylamino)ethyl]-2H-indazol-6-yl}acetamide The titled compound was prepared according to the procedure described in Example 1 substituting 2-(2-Dimethylamino-ethyl)-2H-indazol-6-ylamine for 2-(2-Pyrrolidin-1-yl-ethyl)-2H-indazol-4-ylamine. $^1$H NMR (300 MHz, DMSO-$d_6$) ppm 2.16 (s, 6H), 2.75 (t, 2H, J=6.44), 3.58 (s, 2H), 4.44 (t, 2H, J=6.44), 5.08 (s, 2H), 6.97 (m, 2H), 7.05 (m, 1H), 7.25–7.45 (m, 8H), 7.59 (m, 1H), 8.02 (s, 1H), 9.26 (s, 1H); MS (DCI/$NH_3$) m/z 429 [M+H]$^+$.

Example 49

N-{2-[2-(dimethylamino)ethyl]-2H-indazol-6-yl}-2-(3-phenoxyphenyl)acetamide

The title compound was prepared according to the procedure for Example 48 substituting (3-phenoxy-phenyl)-acetic acid for (4-phenoxy-phenyl)-acetic acid. $^1$H NMR (500 MHz, dmso-$d_6$) δ ppm 2.16 (s, 6H), 2.76 (t, 2H), 3.65 (s, 2H), 4.44 (t, 2H), 6.88 (m, 1H), 7.04 (m, 4H), 7.14 (m, 2H), 7.37 (m, 3H), 7.60 (m, 1H), 8.00 (s, 1H), 8.26 (s, 1H), 10.09 (s, 1H); MS (ESI) m/z 415 [M+H]$^+$.

Example 50

N-{2-[2-(dimethylamino)ethyl]-2H-indazol-6-yl}-3-phenoxybenzamide

The title compound was prepared according to the procedure for Example 48 substituting 3-phenoxy-benzoic acid for (4-phenoxy-phenyl)-acetic acid. 1H NMR (500 MHz, DMSO-D6) δ ppm 2.18 (s, 6 H), 2.78 (t, J=6.55 Hz, 2 H), 4.47 (t, J=6.55 Hz, 2 H), 7.08 (m, 2 H), 7.21 (m, 2 H), 7.30 (m, 1 H), 7.44 (m, 2 H), 7.55 (m, 1 H), 7.63 (m, 2 H), 7.77 (m, 1 H), 8.12 (s, 1 H), 8.30 (s, 1 H), 10.22 (s, 1 H); MS (ESI) m/z 401 [M+H]$^+$.

Example 51

4-(1,1'-biphenyl-4-yl)-N-{2-[2-(dimethylamino)ethyl]-2H-indazol-6-yl}-4-oxobutanamide The title compound was prepared according to the procedure for Example 48 substituting 4-biphenyl-4-yl-4-oxo-butyric acid for (4-phenoxy-phenyl)-acetic acid. $^1$H NMR (500 MHz, dmso-$d_6$) δ ppm 2.17 (s, 6H), 2.77 (m, 4H), 3.40 (t, 2H), 4.44 (t, 2H), 7.08 (m, 1H), 7.44 (m, 1H), 7.51 (m, 2H), 7.60 (m, 1H), 7.76 (m, 2H), 7.85 (m, 2H), 8.03 (s, 1H), 8.10 (m, 2H), 8.26 (s, 1H), 10.00 (s, 1H); MS (ESI) m/z 441 [M+H]$^+$.

Example 52

2-(1,1'-biphenyl-4-yl)-N-{2-[2-(dimethylamino)ethyl]-2H-indazol-6-yl}acetamide The title compound was prepared according to the procedure for Example 48 substituting 4-oxo-4-(4-phenoxy-phenyl)-butyric acid for (4-phenoxy-phenyl)-acetic acid. $^1$H NMR (500 MHz, dmso-$d_6$) δ ppm 2.16 (s, 6H), 2.76 (t, 2H), 3.71 (s, 2H), 4.44 (t, 2H), 7.09 (m, 1H), 7.35 (m, 1H), 7.46 (m, 4H), 7.63 (m, 5H), 8.04 (s, 1H), 8.27 (s, 1H), 10.15 (s, 1H); MS (ESI) m/z 399 [M+H]$^+$.

Example 53

N-{2-[2-(dimethylamino)ethyl]-2H-indazol-6-yl}-4-oxo-4-(4-phenoxyphenyl)butanamide The title compound was prepared according to the procedure for Example 48 substituting biphenyl-4-yl-acetic acid for (4-phenoxy-phenyl)-acetic acid. $^1$H NMR (500 MHz, dmso-d$_6$) δ ppm 2.17 (s, 6H), 2.74 (m, 4H), 3.33 (m, 2H), 4.43 (t, 2H), 7.07 (m, 3H), 7.13 (m, 2H), 7.25 (m, 1H), 7.47 (m, 2H), 7.59 (m, 1H), 8.03 (m, 3H), 8.25 (s, 1H), 9.97 (s, 1H); MS (ESI) m/z 457 [M+H]$^+$.

Example 54

4-(4-chlorophenyl)-N-{2-[2-(dimethylamino)ethyl]-2H-indazol-6-yl}cyclohexanecarboxamide The title compound was prepared according to the procedure for Example 48 substituting 4-(4-chloro-phenyl)-cyclohexanecarboxylic acid for (4-phenoxy-phenyl)-acetic acid. $^1$H NMR (500 MHz, dmso-d$_6$) δ ppm 1.48 (m, 2H), 1.63 (m, 2H), 1.89 (m, 2H), 1.97 (m, 2H), 2.17 (s, 6H), 2.43 (m, 1H), 2.57 (m, 1H), 2.76 (t, 2H), 4.44 (t, 2H), 7.09 (m, 1H), 7.29 (m, 2H), 7.35 (m, 2H), 7.58 (m, 1H), 8.06 (s, 1H), 8.25 (s, 1H), 9.82 (s, 1H); MS (ESI) m/z 457 [M+H]$^+$.

Example 55

4-benzyl-N-{2-[2-(dimethylamino)ethyl]-2H-indazol-6-yl}benzamide

The title compound was prepared according to the procedure for Example 48 substituting 4-benzyl-benzoic acid for (4-phenoxy-phenyl)-acetic acid. $^1$H NMR (500 MHz, dmso-d$_6$) δ ppm 2.18 (s, 6H), 2.78 (t 2H), 4.04 (s, 2H), 4.46 (t, 2H), 7.20 (m, 1H), 7.29 (m, 5H), 7.39 (m, 2H), 7.63 (m, 1H), 7.89 (m, 2H), 8.13 (s, 1H), 8.29 (s, 1H), 10.11 (s, 1H); MS (ESI) m/z 399 [M+H]$^+$.

Example 56

N-{2-[2-(dimethylamino)ethyl]-2H-indazol-6-yl}-2-(4-phenoxyphenyl)acetamide

The titled compound was prepared according to the procedure described in Example 5 substituting 2-(2-Dimethylamino-ethyl)-2H-indazol-6-ylamine for 2-(2-Pyrrolidin-1-yl-ethyl)-2H-indazol-4-ylamine. $^1$H NMR (300 MHz, DMSO-d$_6$) ppm 2.84 (s, 6H), 3.66 (s, 2H), 3.71 (t, 2H, J=6.24), 4.80 (t, 2H, J=6.24), 6.97–7.01(m, 4H), 7.10 (m, 1H), 7.13 (m, 1H), 7.36–7.39 (m, 4H), 7.67 (m, 1H), 8.17 (s, 1H), 8.38(s, 1H), 9.46 (s, 1H); MS (DCI/NH$_3$) m/z 415 [M+H]$^+$.

Example 57

N-{2-[2-(dimethylamino)ethyl]-2H-indazol-6-yl}-N'-(4-phenoxyphenyl)urea

The titled compound was prepared according to the procedure described in Example 10 substituting 2-(2-Dimethylamino-ethyl)-2H-indazol-6-ylamine for 2-(2-Dimethylamino-ethyl)-2H-indazol-5-ylamine. $^1$H NMR (300 MHz, DMSO-d$_6$) ppm 2.86 (s, 6H), 3.71 (m, 2H), 4.79 (m, 2H), 6.90–7.12 (m, 6H), 7.35–7.68 (m, 6H), 7.97 (m, 1H), 8.36 (s, 1H), 8.95 (s, 1H), 9.46 (s, 1H); MS (DCI/NH$_3$) m/z 416 [M+H]$^+$.

Example 58

N-{2-[2-(cyclopentylamino)ethyl]-2H-indazol-6-yl}-N'-(4-phenoxyphenyl)urea

Example 58A 2-(2,2-dimethoxyethyl)-6-nitro-2H-indazole

To a stirred suspension of 6-nitroindazole (10 g, 61 mmol) and K$_2$CO$_3$ (9.31 g, 67.5 mmol) in N,N-dimethylformamide (60 mL) at room temperature was added bromoacetaldehyde dimethylacetal (8.0 mL, 67.5 mmol) and the reaction was heated to 55 C for 18 ours. The mixture was allowed to cool and was diluted with diethyl ether (30 mL) and H$_2$O (60 mL). The layers were separated and the aqueous was extracted with additional diethyl ether (3×30 mL). The combined organic layers were dried with anhydrous Na$_2$SO$_4$, filtered and concentrated under reduced pressure to an orange oil. The residue was purified by MPLC (SiO$_2$, 9:1 Hx:Ethyl acetateto 4:1 Hx:EtoAc) to yield the titled product as a yellow solid. $^1$H NMR (300 MHz, DMSO-d$_6$) δ ppm 3.31 (m, 6 H), 4.67 (d, J=5.42 Hz, 2 H), 4.91 (t, J=5.42 Hz, 1H), 7.82 (m1 H), 7.99 (m, 1 H) and 8.63 (s, 2 H); MS (ESI) 252 (M+H)$^+$.

Example 58B 2-(2,2-dimethoxyethyl)-2H-indazol-6-ylamine

To a stirred solution of 2-(2,2-dimethoxyethyl)-6-nitro-2H-indazole (1.89 g, 7.52 mmol) and NH$_4$Cl (337 mg, 6.01 mmol) in ethanol/H$_2$O (2:1, 75 mL) at room temperature was added Fe (1.28 g, 23.7 mmol) and the resulting mixture was heated for 2 hours at 70 C. The mixture was allowed to cool and was filtered through celite. The residue was washed with hot Methanol (5×20 mL) and the combined eluent was concentrated under reduced pressure. The residue was diluted with ethyl acetate (50 mL) and filtered. Concentration of the organic layer under reduced pressure provided 2-(2,2-dimethoxyethyl)-2H-indazol-6-ylamine as an amber oil. $^1$H NMR (300 MHz, DMSO-d$_6$) δ ppm 3.25 (m, 6 H), 4.34 (d, J=5.43 Hz, 2 H), 4.81 (t, J=5.59 Hz, 1 H), 5.22 (s, 2 H), 6.52 (m, 2 H), 7.37 (m, 1 H) and 8.02 (s, 1 H); MS (ESI) 222 (M+H)$^+$.

Example 58C

1-[2-(2,2-dimethoxyethyl)-2H-indazol-6-yl]-3-(4-phenoxyphenyl)urea

To a stirred solution of name (1.04 g, 4.74 mmol) in THF (16 mL) was added 4-phenoxyphenylisocyanate (1.0 g, 4.74 mmol) and the reaction was heated to 40 C for 3 h. The heating bath was removed and the reaction was concentrated under reduced pressure to a dark oil. The oil was dissolved in ethyl acetate and passed through a small plug of SiO$_2$ gel, eluting with additional ethyl acetate. The eluent was then concentrated under reduced pressure to provide 1-[2-(2,2-dimethoxyethyl)-2H-indazol-6-yl]-3-(4-phenoxyphenyl)urea as a beige solid. $^1$H NMR (300 MHz, DMSO-d$_6$) δ ppm 3.28 (s, 6 H), 4.46 (d, J=5.43 Hz, 2 H), 4.86 (t, J=5.43 Hz, 1 H), 6.97 (m, 5 H), 7.09 (m, 1 H), 7.36 (m, 2H), 7.49 (m, 2 H), 7.61 (m, 1 H), 7.84 (s, 1 H), 8.23 (s, 1 H) and 8.66 (m, 2 H); MS (ESI) 433 (M+H)$^+$.

Example 58D

1-[2-(2-oxo-ethyl)-2H-indazol-6-yl]-3-(4-phenoxyphenyl)urea

To a stirred solution of 1-[2-(2,2-dimethoxyethyl)-2H-indazol-6-yl]-3-(4-phenoxyphenyl)urea (1.5 g, 3.47 mmol) in acetone (250 mL) was added 2N aqueous HCl (10 mL) and the reaction was heated to reflux for 72 hours. The mixture was allowed to cool and was concentrated under reduced pressure to a volume of 30 mL. Ethyl acetate (300 mL) was added to the slurry with stirring and the mixture was filtered. The solid was washed with additional ethyl acetate (10 mL) and air-dried to provide 1-[2-(2-oxo-ethyl)-2H-indazol-6-yl]-3-(4-phenoxyphenyl)urea. 1H NMR (300 MHz, DMSO-D6) δ ppm 5.38 (s, 2 H), 6.98 (m, 5 H), 7.09 (m, 1 H), 7.36 (m, 2 H), 7.49 (m, 2 H), 7.65 (m, 1 H), 7.87 (s, 1 H), 8.27 (s, 1 H), 8.87 (m, 2 H), 9.66 (s, 1 H); MS (ESI) 385 (M−H)−.

Example 58

N-{2-[2-(cyclopentylamino)ethyl]-2H-indazol-6-yl}-N'-(4-phenoxyphenyl)urea

A mixture of 1-[2-(2-oxo-ethyl)-2H-indazol-6-yl]-3-(4-phenoxy-phenyl)urea (20 mg, 0.05 mmol) and cyclopentylamine (10 mL, 0.10 mmol) in THF (0.5 mL) was shaken at room temperature for 30 minutes. 1M Sodium cyanoborohydride in THF (104 µL, 0.10 mmol) was added and the solution was shaken at room temperature for 16 hours. The sample was diluted with ethyl acetate, washed with water, concentrated under reduced pressure and purified by RP-HPLC. $^1$H NMR (300 MHz, DMSO-$d_6$) δ ppm 1.6 (m, 6 H), 2.0 (m, 2 H), 3.55 (m, 2 H), 4.35 (m, 2 H), 4.70 (t, 2 H), 6.97 (m, 5 H), 7.12 (m, 1 H), 7.35 (m, 2 H), 7.52 (m, 2 H), 7.65 (d, 1 H), 7.95 (s, 1 H), 8.35 (s, 1 H) and 8.70 (m, 2 H.); MS (ESI) 456 (M+H)$^+$.

Example 59

N-(4-phenoxyphenyl)-N'-(2-{2-[(tetrahydrofuran-2-ylmethyl)amino]ethyl}-2H-indazol-6-yl)urea The titled compound was prepared by the method described for Example 58, substituting 2-methylamino-tetrahydrofuran for cyclopentylamine. $^1$H NMR (300 MHz, DMSO-$d_6$) δ ppm 1.50 (m, 1 H), 1.85(m, 2 H), 2.0(m, 1 H), 3.0 (m, 1 H), 3.15 (m, 1 H), 3.55 (m, 2 H), 3.75 (m, 2 H), 4.10 (m, 2 H), 4.70 (t, 2 H), 6.98 (m, 5 H), 7.85 (m, 1 H), 7.30 (m, 2 H), 7.53 (m, 2 H), 7.65 (d, 1 H), 7.95 (s, 1 H), 8.35 (s, 1 H) and 8.70 (m, 2 H); MS (ESI) 472 (M+H)$^+$.

Example 60

N-{2-[2-(4-methylpiperidin-1-yl)ethyl]-2H-indazol-6-yl}-N'-(4-phenoxyphenyl)urea The titled compound was prepared by the method described for Example 58, substituting 4-methylpiperidine for cyclopentylamine. $^1$H NMR (300 MHz, DMSO-$d_6$) δ ppm 0.9 (d, 3 H), 1.30 (m, 2 H), 1.6 (m, 1 H), 1.8 (m, 2 H), 3.0 (m, 2 H), 3.5 (m, 2 H), 3.7 (m, 2 H), 4.8 (t, 2 H), 7.05 (m, 5 H), 7.13 (m, 1 H), 7.30 (m, 2 H), 7.53 (m, 2 H), 7.65 (d, 1 H), 7.95 (s, 1 H), 8.35 (s, 1 H) and 8.8 (m, 2 H); MS (ESI) 470.2 (M+H)$^+$.

Example 61

N-{2-[2-(3-methylpiperidin-1-yl)ethyl]-2H-indazol-6-yl}-N'-(4-phenoxyphenyl)urea The titled compound was prepared by the method described for Example 58, substituting 3-methylpiperidine for cyclopentylamine. $^1$H NMR (300 MHz, DMSO-$d_6$) δ ppm 1.25 (d, 3 H), 1.7 (m, 6 H), 3.0 (m, 2 H), 3.3 (m, 3 H), 4.8 (m, 2 H), 6.98 (m, 5 H), 7.12 (m, 1 H), 7.35 (m, 2 H), 7.54 (m, 2 H), 7.65 (d, 1 H), 7.95 (s, 1 H), 8.35 (s, 1 H), 8.75 (m, 2 H); MS (ESI) 470.2 (M+H)$^+$.

Example 62

N-{2-[2-(2-methylpyrrolidin-1-yl)ethyl]-2H-indazol-6-yl}-N'-(4-phenoxyphenyl)urea The titled compound was prepared by the method described for Example 58, substituting 2-methylpyrrolidine for cyclopentylamine. $^1$H NMR (300 MHz, DMSO-$d_6$) δ ppm 1.3 (d, 3 H), 1.6 (m, 1 H), 1.9 (m, 2 H), 2.2 (m, 1 H), 3.15 (m, 1 H), 3.5 (m, 2 H), 4.0 (m, 1 H), 4.8 (t, 2 H), 6.97 (m, 5 H), 7.13 (m, 1 H), 7.35 (m, 2 H), 7.54 (m, 2 H), 7.65 (d, 1 H), 7.95(s, 1 H), 8.35 (s, 1 H) and 8.8 (m, 2 H), 9.2 (m, 1 H); MS (ESI) 456 (M+H)$^+$.

Example 63

N-(2-{2-[(2-morpholin-4-ylethyl)amino]ethyl}-2H-indazol-6-yl)-N'-(4-phenoxyphenyl)urea The titled compound was prepared by the method described for Example 58, substituting 2-morpholin-2-yl-ethylamine for cyclopentylamine. $^1$H NMR (300 MHz, DMSO-$d_6$) δ ppm 3.03 (m, 6 H), 3.35 (m, 2 H), 3.58 (m, 2 H), 3.77 (m, 4 H), 4.8 (t, 2 H), 5.0 (m, 1 H), 6.97 (m, 5 H), 7.15 (m, 1 H), 7.35 (m, 2 H), 7.53 (m, 2 H), 7.65 (d, 1 H), 7.95 (s, 1 H), 8.35 (s, 1 H) and 8.8 (d, 2 H); MS (ESI) 501 (M+H)$^+$.

Example 64

N-{2-[2-(2-methylpiperidin-1-yl)ethyl]-2H-indazol-6-yl}-N'-(4-phenoxyphenyl)urea The titled compound was prepared by the method described for Example 58, substituting 2-methylpiperidine for cyclopentylamine. $^1$H NMR (300 MHz, DMSO-$d_6$) δ ppm 0.88 (d, 3 H), 0.98 (m, 1 H), 1.8 (m, 4 H), 2.9 (m, 2 H), 3.3 (m, 2 H), 3.7 (m, 2 H), 4.8 (t, 2 H), 6.97 (m, 5 H), 7.12 (m, 1 H), 7.35 (m, 2 H), 7.54 (m, 2 H), 7.65 (d, 1 H), 7.95 (s, 1 H), 8.35 (s, 1 H) and 8.8 (m, 2 H); MS (ESI) 470.2 (M+H)$^+$.

Example 65

N-{2-[2-(methylamino)ethyl]-2H-indazol-6-yl}-N'-(4-phenoxyphenyl)urea

The titled compound was prepared by the method described for Example 58, substituting methylamine for cyclopentylamine. $^1$H NMR (300 MHz, DMSO-$d_6$) δ ppm 2.65 (m, 3 H), 3.85 (m, 2 H), 4.4 (m, 1 H), 4.7 (m, 2 H), 6.97 (m, 5 H), 7.12 (m, 1 H), 7.35 (m, 2 H), 7.53 (m, 2 H), 7.65 (d, 1 H), 7.95 (s, 1 H), 8.35 (s, 1 H) and 8.8 (d, 2 H); MS (ESI) 402 (M+H)$^+$.

Example 66

N-{2-[2-(2,5-dimethylpyrrolidin-1-yl)ethyl]-2H-indazol-6-yl}-N'-(4-(phenoxyphenyl)urea The titled compound was prepared by the method described for Example 58, substituting 2,5-dimethylpyrrolidine for cyclopentylamine. $^1$H NMR (300 MHz, DMSO-d$_6$) δ ppm 1.3 (m, 6 H), 1.7 (m, 2 H), 2.2 (m, 2 H), 3.55 (m, 2 H), 3.8 (m, 2 H), 4.8 (m, 2 H), 6.98 (m, 5 H), 7.13 (m, 1 H), 7.35 (m, 2 H), 7.53 (m, 2 H), 7.65 (d, 1 H), 7.95 (s, 1 H), 8.35 (s, 1 H) and 8.8 (m, 2 H); MS (ESI) 470.2 (M+H)$^+$.

Example 67

N-(2-{3-[3-(hydroxymethyl)piperidin-1-yl]propyl}-2H-indazol-6-yl)-N'-(4-phenoxyphenyl)urea

Example 67A 2-(3,3-dimethoxypropyl)-6-nitro-2H-indazole

To a stirred suspension of 6-nitroindazole (4.05 g, 24.8 mmol), K$_2$CO$_3$ (4.45 g, 32.2 mmol) and KI (411 mg, 2.48 mmol) in N,N-dimethylformamide (25 mL) at room temperature was added 3-bromopropoinaldehyde dimethylacetal (5 g. 27.3 mmol) and the reaction was heated to 70 C for 18 h. The heating bath was removed and upon reaching room temperature the reaction was diluted with Et$_2$O (25 mL) and H$_2$O (25 mL). The layers were separated and the aqueous was extracted with additional Et2O (3×25 mL). The combined organic layers were dried with anhydrous Na$_2$SO$_4$, filtered and concentrated under reduced pressure to an orange oil. The residue was purified by MPLC (SiO2, 9:1 Hx:Ethyl acetateto 4:1 Hx:EtOAc) to yield 2-(3,3-dimethoxypropyl)-6-nitro-2H-indazole as an orange oil. $^1$H NMR (300 MHz, DMSO-D6) δ ppm 2.24 (m, 2 H), 3.25 (s, 6 H), 4.39 (t, J=5.59 Hz, 1 H), 4.56 (m, 2 H), 7.81 (m, 1 H), 7.97 (d, J=9.15 Hz, 1 H), 8.63 (m, 1 H) and 8.66 (m, 1 H); MS (ESI) 266 (M+H)$^+$.

Example 67B 2-(3,3-dimethoxypropyl)-2H-indazole-6-ylamine

To a stirred solution of 2-(3,3-dimethoxypropyl)-6-nitro-2H-indazole (1.5 g, 5.66 mmol) and NH$_4$Cl (254 mg, 4.53 mmol) in EtOH/H$_2$O (2:1, 56 mL) at room temperature was added Fe (962 mg, 17.8 mmol) in a single poroom temperature ion and the resulting mixture was heated for 2 h at 70 C. The heating bath was removed and upon reaching room temperature the mixture was filtered through a pad of celite. The residue was washed with hot Methanol (5×20 mL) and the combined eluent was concentrated under reduced pressure. The residue was diluted with Ethyl acetate (30 mL) and filtered. Concentration of the organic layer under reduced pressure gave 2-(3,3-dimethoxypropyl)-2H-indazole-6-ylamine as an amber oil. $^1$H NMR (300 MHz, DMSO-D6) δ ppm 2.12 (m, 2 H), 3.24 (s, 6 H), 4.26 (m, 2 H), 4.32 (t, J=5.59 Hz, 1 H), 5.18 (m, 2 H), 6.52 (m, 2 H), 7.35 (d, J=8.48 Hz, 1 H) and 8.04 (s, 1 H).

Example 67C

1-[2-(3,3-dimethoxypropyl)-2H-indazol-6-yl]-3-(4-phenoxyphenyl)urea

To a stirred solution of 2-(3,3-dimethoxypropyl)-2H-indazole-6-ylamine (582 mg, 2.48 mmol) in THF (9 mL) was added 4-phenoxyphenylisocyanate (523 mg, 2.48 mmol) and the reaction was heated to 40 C for 3 h. The heating bath was removed and the reaction was then concentrated under reduced pressure to a dark oil. The oil was dissolved in Ethyl acetate and passed through a small plug of SiO2 gel, eluting with additional EtOAc. The eluent was concentrated under reduced pressure to give 1-[2-(3,3-dimethoxypropyl)-2H-indazol-6-yl]-3-(4-phenoxyphenyl)urea as a beige solid. $^1$H NMR (300 MHz, DMSO-D6) δ ppm 2.50 (m, 2 H), 3.32 (m, 6 H), 4.36 (m, 3 H), 6.97 (m, 6 H), 7.09 (t, J=7.46 Hz, 1 H), 7.36 (m, 2 H), 7.48 (m, 2 H), 7.59 (d, J=8.82 Hz, 1 H), 7.83 (s, 1 H) and 8.66 (m, 2 H); MS(ESI) 445 (M–H)$^-$.

Example 67D

1-[2-(3-oxopropyl)-2H-indazol-6-yl]-3-(4-phenoxyphenyl)urea

To a stirred solution of 1-[2-(3,3-dimethoxypropyl)-2H-indazol-6-yl]-3-(4-phenoxyphenyl)urea (832 mg, 1.87 mmol) in acetone (15 mL) was added 2N aqueous HCl (7.5 mL) and the reaction was heated to 50 C for 3h. The heating bath was removed and the reaction was concentrated under reduced pressure to a volume of ~5 mL. Et$_2$O was added to the slurry with stirring and the mixture was filtered. The solid was washed with additional Et$_2$O (10 mL) and air-dried to give 1-[2-(3-oxopropyl)-2H-indazol-6-yl]-3-(4-phenoxyphenyl)urea as a beige solid. $^1$H NMR (300 MHz, DMSO-D6) δ ppm 3.11 (t, J=6.27 Hz, 2 H), 4.67 (t, J=6.61 Hz, 2 H), 6.97 (m, 5 H), 7.10 (m, 1 H), 7.36 (m, 2 H), 7.48 (m, 2 H), 7.59 (m, 1 H), 7.82 (s, 1 H), 8.26 (s, 1 H), 8.70 (m, 2 H) and 9.75 (s, 1 H); MS (ESI) 399 (M–H)$^-$.

Example 67

N-(2-{3-[3-(hydroxymethyl)piperidin-1-yl]propyl}-2H-indazol-6-yl)-N'-(4-phenoxyphenyl)urea To a solution of 1-[2-(3-oxopropyl)-2H-indazol-6-yl]-3-(4-phenoxyphenyl)urea (20 mg, 0.05 mmol) in Methanol containing 2% v/v AcOH (1 mL) was added 3-piperidinemethanol (10 mg, 0.10 mmol) and MS-CNBH$_3$ (52 mg, 0.065 mmol). The reaction was shaken vigorously at 40 C for 18h. The reaction was filtered, eluting with additional Methanol (3×0.5 mL). The sample was directly purified by RP-HPLC to afford the titled product. $^1$H NMR (300 MHz, DMSO-D6) δ ppm 1.15 (m, 1 H), 1.65 (m, 2 H), 1.83 (m, 2 H), 2.30 (m, 2 H), 2.63 (m, 1 H), 2.77 (m, 1 H), 3.10 (m, 2 H), 3.24 (dd, J=10.68, 6.61 Hz, 1 H), 3.36 (m, 1 H), 3.44 (m, 2 H), 4.47 (t, J=6.27 Hz, 2 H), 6.97 (m, 5 H), 7.09 (m, 1 H), 7.36 (m, 2 H), 7.49 (m, 2 H), 7.62 (m, 1 H), 7.90 (s, 1 H), 8.29 (s, 1 H), 8.76 (m, 2 H) and 9.16 (s, 1 H); MS (ESI) 500 (M+H)$^+$.

Example 68

N-{2-[3-(cyclopentylamino)propyl]-2H-indazol-6-yl}-N'-(4-phenoxyphenyl)urea

The titled compound was prepared by the method described for Example 67, substituting cyclopentylamine for 3-piperidinemethanol. $^1$H NMR (300 MHz, DMSO-D6) δ ppm 1.53 (s, 4 H), 1.68 (m, 2 H), 1.93 (m, 2 H), 2.26 (m, 2 H), 2.93 (m, 2 H), 4.49 (t, J=6.44 Hz, 2 H), 6.95 (m, 5 H), 7.09 (m, 1 H), 7.36 (m, 2 H), 7.48 (m, 2 H), 7.62 (m, 1 H), 7.90 (s, 1 H), 8.28 (s, 1 H), 8.43 (s, 2 H) and 8.72 (s, 2 H); MS (ESI) 470 (M+H)$^+$.

Example 69

N-(4-phenoxyphenyl)-N'-[2-(3-pyrrolidin-1-ylpropyl)-2H-indazol-6-yl]urea

The titled compound was prepared by the method described for Example 67, substituting pyrrolidine for 3-piperidinemethanol. $^1$H NMR (300 MHz, DMSO-D6) δ ppm 1.85 (m, 2 H), 1.99 (m, 2 H), 2.27 (m, 2 H), 2.98 (m, 2 H), 3.13 (m, 2 H), 3.54 (m, 2 H), 4.47 (t, J=6.27 Hz, 2 H), 6.96 (m, 5 H), 7.09 (m, 1 H), 7.36 (m, 2 H), 7.48 (m, 2 H), 7.62 (m, 1 H), 7.90 (s, 1 H), 8.29 (s, 1 H) and 8.74 (m, 2 H); MS (ESI) 456 (M+H)$^+$.

Example 70

N-(2-{3-[(2S)-2-(methoxymethyl)pyrrolidin-1-yl]propyl}-2H-indazol-6-yl)-N'-(4-phenoxyphenyl)urea The titled compound was prepared by the method described for Example 67, substituting (S)-2-methoxymethylpyrrolidine for 3-piperidinemethanol. $^1$H NMR (300 MHz, DMSO-D6) δ ppm 1.66 (m, 1 H), 1.82 (m, 1 H), 1.97 (m, 1 H), 2.09 (m, 1 H), 2.27 (m, 2 H), 3.06 (m, 4 H), 3.25 (s, 3 H), 3.31 (m, 2 H), 4.47 (m, 2 H), 6.96 (m, 5 H), 7.09 (m, 1 H), 7.36 (m, 2 H), 7.48 (m, 2 H), 7.62 (m, 1 H), 7.91 (s, 1 H), 8.28 (s, 1 H), 8.72 (s, 2 H), 9.41 (s, 1 H); MS (ESI) 500 (M+H)$^+$.

Example 71

N-(2-{3-[(2S)-2-(hydroxymethyl)pyrrolidin-1-yl]propyl}-2H-indazol-6-yl)-N'-(4-phenoxyphenyl)urea The titled compound was prepared by the method described for Example 67, substituting (S)-2-lpyrrolidinemethanol for 3-piperidinemethanol. $^1$H NMR (300 MHz, DMSO-D6) δ ppm 1.75 (s, 2 H), 1.95 (s, 2 H), 2.29 (m, 2 H), 3.07 (m, 4 H), 3.38 (m, 3 H), 4.46 (m, 2 H), 6.96 (m, 5 H), 7.09 (m, 1 H), 7.36 (m, 2 H), 7.48 (m, 2 H), 7.62 (m, 1 H), 7.90 (s, 1 H), 8.28 (s, 1 H), 8.73 (m, 2 H) and 9.23 (s, 1 H); MS (ESI) 486 (M+H)$^+$.

Example 72

N-(2-{3-[2-(2-hydroxyethyl)piperidin-1-yl]propyl}-2H-indazol-6-yl)-N'-(4-phenoxyphenyl)urea The titled compound was prepared by the method described for Example 67, substituting 2-piperidineethanol for 3-piperidinemethanol. $^1$H NMR (300 MHz, DMSO-D6) δ ppm 1.45 (m, 1 H), 1.60 (m, 2 H), 1.76 (m, 3 H), 1.99 (m, 1 H), 2.30 (m, 2 H), 3.10 (m, 3 H), 3.28 (m, 2 H), 3.45 (m, 2 H), 3.60 (m, 2 H), 4.47 (m, 2 H), 6.96 (m, 5 H), 7.09 (m, 1 H), 7.36 (m, 2 H), 7.49 (m, 2 H), 7.62 (m, 1 H), 7.91 (s, 1 H), 8.29 (s, 1 H) and 8.74 (s, 2 H); MS (ESI) 514 (M+H)$^+$.

Example 73

N-{2-[3-(4-hydroxypiperidin-1-yl)propyl]-2H-indazol-6-yl}-N'-(4-phenoxyphenyl)urea The titled compound was prepared by the method described for Example 67, substituting 4-hydroxypiperidine for 3-piperidinemethanol. $^1$H NMR (300 MHz, DMSO-D6) δ ppm 1.51 (m, 1 H), 1.75 (m, 2 H), 1.94 (m, 1 H), 2.31 (m, 2 H), 2.97 (m, 1 H), 3.09 (m, 3 H), 3.28 (m, 1 H), 3.43 (m, 1 H), 3.59 (m, 1 H), 3.93 (m, 1 H), 4.46 (t, J=6.44 Hz, 2 H), 6.97 (m, 5 H), 7.09 (m, 1 H), 7.36 (m, 2 H), 7.49 (m, 2 H), 7.62 (m, 1 H), 7.90 (s, 1 H), 8.29 (m, 1 H) and 8.82 (m, 2 H); MS (ESI) 486 (M+H)$^+$.

Example 74

N-{2-[3-(3-hydroxypyrrolidin-1-yl)propyl]-2H-indazol-6-yl}-N'-(4-phenoxyphenyl)urea The titled compound was prepared by the method described for Example 67, substituting 3-hydroxypyrrolidine for 3-piperidinemethanol. $^1$H NMR (300 MHz, DMSO-D6) δ ppm 1.91 (m, 2 H), 2.27 (m, 2 H), 3.17 (m, 7 H), 3.60 (br s, 1 H), 4.46 (m, 2 H), 6.96 (m, 5 H), 7.09 (m, 1 H), 7.37 (m, H), 7.48 (m, 2 H), 7.62 (m, 1 H), 7.90 (s, 1 H), 8.28 (s, 1 H), 8.71 (m, 2 H); MS (ESI) 472 (M+H)$^+$.

Example 75

N-(4-phenoxyphenyl)-N'-[2-(3-piperidin-1-ylpropyl)-2H-indazol-6-yl]urea

The titled compound was prepared by the method described for Example 67, substituting piperidine for 3-piperidinemethanol. $^1$H NMR (300 MHz, DMSO-D6) δ ppm 1.37 (m, 1 H), 1.63 (m, 3 H), 1.78 (m, 2 H), 2.30 (m, 2 H), 2.88 (m, 2 H), 3.06 (m, 2 H), 3.42 (m, 2 H), 4.47 (t, J=6.61 Hz, 2 H), 6.96 (m, 5 H), 7.09 (m, 1 H), 7.36 (m, 2 H), 7.48 (m, 2 H), 7.62 (m, 1 H), 7.91 (s, 1 H), 8.29 (s, 1 H) and 8.74 (m, 2 H); MS (ESI) 470 (M+H)$^+$.

Example 76

N-[2-(3-morpholin-4-ylpropyl)-2H-indazol-6-yl]-N'-(4-phenoxyphenyl)urea

The titled compound was prepared by the method described for Example 67, substituting morpholine for 3-piperidinemethanol. $^1$H NMR (300 MHz, DMSO-D6) δ ppm 2.30 (m, 2 H), 3.14 (m, 4 H), 3.42 (m, 4 H), 3.96 (m, 2 H), 4.48 (t, J=6.61 Hz, 2 H), 6.97 (m, 5 H), 7.09 (t, J=7.29 Hz, 1 H), 7.36 (m, 2 H), 7.49 (m, 2 H), 7.62 (m, 1 H), 7.91 (s, 1 H), 8.29 (s, 1 H) and 8.74 (m, 2 H); MS (ESI) 472 (M+H)$^+$.

Example 77

N-{2-[3-(cyclohexylamino)propyl]-2H-indazol-6-yl}-N'-(4-phenoxyphenyl)urea

The titled compound was prepared by the method described for Example 67, substituting cyclohexylamine for 3-piperidinemethanol. $^1$H NMR (300 MHz, DMSO-D6) δ ppm 1.20 (m, 5 H), 1.57 (m, 1 H), 1.74 (m, 2 H), 1.96 (m, 2 H), 2.23 (m, 2 H), 2.95 (m, 3 H), 4.48 (t, J=6.44 Hz, 2 H), 6.96 (m, 5 H), 7.09 (m, 1 H), 7.36 (m, 2 H), 7.49 (m, 2 H), 7.62 (m, 1 H), 7.90 (s, 1 H), 8.27 (m, 2 H) and 8.74 (m, 2 H); MS (ESI) 483 (M+H)$^+$.

Example 78

N-(1-{3-[6-({[(4-phenoxyphenyl)amino]carbonyl}amino)-2H-indazol-2-yl]propyl}pyrrolidin-3-yl)acetamide The titled compound was prepared by the method described for Example 67, substituting 3-acetamidopyrrolidine for 3-piperidinemethanol. $^1$H NMR (300 MHz, DMSO-D6) δ ppm 1.83 (m, 3 H), 2.27 (m, 2 H), 3.17 (m, 4 H), 3.62 (m, 3 H), 4.27 (m, 2 H), 4.47 (m, 2 H), 6.96 (m, 5 H), 7.09

(m, 1 H), 7.37 (m, 2 H), 7.48 (m, 2 H), 7.62 (m, 1 H), 7.90 (s, 1 H), 8.28 (s, 1 H), 8.72 (m, 2 H) and 9.69 (s, 1 H); MS (ESI) 513 (M+H)+.

Example 79

N-{2-[3-(2-methylpyrrolidin-1-yl)propyl]-2H-indazol-6-yl}-N'-(4-phenoxyphenyl)urea The titled compound was prepared by the method described for Example 67, substituting 2-methylpyrrolidine for 3-piperidinemethanol. $^1$H NMR (300 MHz, DMSO-D6) δ ppm 1.31 (d, J=6.44 Hz, 3 H), 1.61 (m, 1 H), 1.92 (m, 2 H), 2.22 (m, 3 H), 3.06 (m, 2 H), 3.40 (m, 3 H), 4.49 (m, 2 H), 6.96 (m, 5 H), 7.09 (m, 1 H), 7.36 (m, 2 H), 7.49 (m, 2 H), 7.62 (m, 1 H), 7.90 (s, 1 H), 8.28 (s, 1 H) and 8.73 (m, 2H); MS (ESI) 470 (M+H)+.

Example 80

N-{2-[3-(2-methylpiperidin-1-yl)propyl]-2H-indazol-6-yl}-N'-(4-phenoxyphenyl)urea The titled compound was prepared by the method described for Example 67, substituting 2-methylpiperidine for 3-piperidinemethanol. $^1$H NMR (300 MHz, DMSO-D6) δ ppm 1.20 (d, J=6.44 Hz, 3 H), 1.56 (m, 6 H), 2.27 (m, 2 H), 3.05 (m, 2 H), 3.17 (m, 2 H), 3.40 (m, 1 H), 4.48 (t, J=6.44 Hz, 2 H), 6.97 (m, 5 H), 7.09 (t, J=7.46 Hz, 1 H), 7.36 (m, 2 H), 7.49 (m, 2 H), 7.62 (m, 1 H,) 7.91 (s, 1 H), 8.30 (s, 1 H) and 8.74 (s, 2 H); MS (ESI) 484 (M+H)+.

Example 81

N-{2-[3-(diisopropylamino)propyl]-2H-indazol-6-yl}N'-(4-phenoxyphenyl)urea

The titled compound was prepared by the method described for Example 67, substituting diisopropylamine for 3-piperidinemethanol. $^1$H NMR (300 MHz, DMSO-D6) δ ppm 1.21 (m, 12 H), 2.29 (m, 2 H), 3.14 (m, 2 H), 3.63 (m, 2 H), 4.49 (t, J=6.27 Hz, 2 H), 6.96 (m, 5 H), 7.09 (m, 1 H), 7.36 (m, 2 H), 7.49 (m, 2 H), 7.63 (m, 1 H), 7.92 (s, 1 H), 8.29 (s, 1 H) and 8.76 (s, 2 H); MS (ESI) 486 (M+H)+.

Example 82

N-{2-[3-(2-ethylpiperidin-1-yl)propyl]-2H-indazol-6-yl}-N'-(4-phenoxyphenyl)urea The titled compound was prepared by the method described for Example 67, substituting 2-ethylpiperidine for 3-piperidinemethanol. $^1$H NMR (300 MHz, DMSO-D6) δ ppm 0.86 (m, 3 H), 1.56 (m, 7 H), 1.91 (m, 1 H), 2.28 (m, 2 H), 3.17 (m, 3 H), 3.40 (m, 2 H), 4.48 (s, 2 H), 6.97 (m, 5 H), 7.09 (m, 1 H), 7.36 (m, 2 H), 7.49 (m, 2 H), 7.62 (m, 1 H), 7.91 (s, 1 H), 8.30 (s, 1 H) and 8.75 (s, 2 H); MS (ESI) 498 (M+H)+.

Example 83

N-(2-{3-[benzyl(2-hydroxyethyl)amino]propyl}-2H-indazol-6-yl)-N'-(4-phenoxyphenyl)urea The titled compound was prepared by the method described for Example 67, substituting N-benzylethanolamine for 3-piperidinemethanol. $^1$H NMR (300 MHz, DMSO-D6) δ ppm 2.37 (m, 2 H), 3.17 (m, 4 H), 3.69 (s, 2 H), 4.36 (s, 2 H), 4.46 (t, J=6.27 Hz, 2 H), 5.32 (s, 1 H), 6.97 (m, 5 H), 7.09 (m, 1 H), 7.38 (m, 7 H), 7.49 (m, 2 H), 7.61 (m, 1 H,) 7.91 (s, 1 H), 8.25 (s, 1 H) and 8.76 (m, 2 H); MS (ESI) 536 (M+H)+.

Example 84

1-(4-phenoxyphenyl)-3-[2-(2-pyrrolidin-1-ylethyl)-2H-indazol-5-yl]-1,3-dihydro-2H-imidazol-2-one

Example 84a

N-(2,2-dimethoxyethyl)-2-(2-pyrrolidin-1-ylethyl)-2H-indazol-5-amine

To a solution of 2-(2-pyrrolidin-1-ylethyl)-2H-indazol-5-amine (1.14 g, 0.497 mmol) in 62 mL of dry THF was added 2.04 mL of dimethyl glyoxal in ether (45% glyoxal by weight). A slurry of NaBH(OAc)$_3$ (1.66 g, 7.83 mmol) in THF (10 mL) was slowly added via addition funnel over 60 minutes, and the mixture stirred at room temperature for 12 hours, after which an additional equivalent of NaBH(OAc)$_3$ was added. After an additional 12 hours, the mixture was quenched with saturated NaHCO$_3$, filtered, and the solvents removed under reduced pressure. The residue was purified via column chromatography eluting with 5–15% Et$_3$N in EtOAc to provide 650 mg (2.04 mmol) of the title compound. $^1$H NMR (300 MHz, DMSO-D6) δ ppm 1.55–1.73 (m, 4 H) 2.39–2.49 (m, 4 H) 2.85–2.96 (m, 2 H) 3.05–3.20 (m, 2 H) 3.28–3.33 (m, 6 H) 4.31–4.45 (m, 2 H) 4.48–4.61 (m, 1 H) 5.14–5.32 (m, 1 H) 6.37–6.50 (m, 1 H) 6.74–6.91 (m, 1 H) 7.21–7.42 (m, 1 H) 7.83–8.02 (m, 1 H); MS (ESI) m/z 319 [M+H]+.

Example 84

1-(4-phenoxyphenyl)-3-[2-(2-pyrrolidin-1-ylethyl)-2H-indazol-5-yl]-1,3-dihydro-2H-imidazol-2-one A mixture of N-(2,2-dimethoxyethyl)-2-(2-pyrrolidin-1-ylethyl)-2H-indazol-5-amine (0.400 g, 1.25 mmol) and 0.265 g of phenoxyphenylisocyanate (1.25 mmol) in 8.4 mL THF was heated to reflux for one hour, after which the mixture was cooled to room temperature and 5 equivalents of 1M HCl was added and the mixture heated to reflux for 2 hours. The mixture was concentrated under reduced pressure taken up in EtOAc and washed with saturated aqueous NaHCO3 (×3), brine, water, dried (MgSO$_4$) and filtered. The solvents were removed under reduced pressure and the residue was purified by RP-HPLC to provide the title compound. $^1$H NMR (300 MHz, DMSO-d$_6$) ppm 8.47 (s, 1H), 7.96 (d, 1H, J=1.35), 7.75 (d, 2H, J=8.81), 7.70 (d, 1H, J=9.16), 7.54 (dd, 1H, J$_1$=9.16, J$_2$=2.03), 7.42 (m, 2H), 7.23 (s, 2H), 7.03–7.09 (m, 5H), 4.55 (t, 2H, J=6.45), 2.97 (t, 2H, J=6.45), 2.47 (m, 4H), 1.65 (m, 4H); MS (ESI) m/z 466 [M+H]+.

Example 85

1-(4-phenoxyphenyl)-3-[2-(2-pyrrolidin-1-ylethyl)-2H-indazol-5-yl]imidazolidin-2-one 1-(4-phenoxyphenyl)-3-[2-(2-pyrrolidin-1-ylethyl)-2H-indazol-5-yl]-1,3-dihydro-2H-imidazol-2-one (Example 84) (0.100 g, 0.215 mmol) was taken up in 20 mL of AcOH along with 100 mg of Pd/C (10% mol/mol) and the mixture was subjected to an atmosphere of hydrogen gas at a pressure of 60 psi in a Parr shaker apparatus. The mixture was shaken at room temperature for 6 hours after which the mixture was filtered through a bed of celite, and the solvents removed under reduced pressure. $^1$H NMR (300 MHz, DMSO-D6) δ ppm 1.75–2.06 (m, 4 H) 3.02–3.15 (m, 2 H) 3.47–3.63 (m, 2 H) 3.74–3.87 (m, 2 H) 3.93–4.12 (m, 4 H) 4.82 (t, J=5.76 Hz, 2 H) 6.94–7.01 (m, 2 H) 7.03–7.14 (m, 3 H) 7.34–7.34 (m, 2 H) 7.62–7.70 (m, 4 H) 7.86 (dd, J=9.49, 2.03 Hz, 1 H) 8.39–8.46 (m, 1 H); MS (ESI) m/z 468 [M+H]$^+$.

What is claimed is:

1. A compound of formula (I),

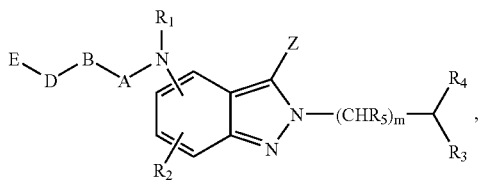

or a therapeutically acceptable salt or prodrug thereof, wherein

A is selected from the group consisting of —C(O)—, —S(O)—, —S(O)$_2$—, —C(=NR$_a$)— and —C(=S)—;

B is a bond or is selected from the group consisting of alkylene, alkenyl, carbonylalkyl, cycloalkyl, —NR$_b$— and —NR$_b$-alkyl;

D is a bond or is selected from the group consisting of alkylene, aryl, arylalkyl, heterocycle and heterocyclealkyl;

E is selected from the group consisting of alkyl, alkyl-C(O)—, alkyl-C(O)—NH—, alkyl-NH—, alkyl-NH—C(O)—, alkyl-NH—S(O)$_2$—, alkoxy, alkyl-S—, alkyl-S(O)$_2$—, alkyl-S(O)$_2$—NH—, aryl, aryl-C(O)—, aryl-C(O)—NH—, aryl-C=N—O—, aryl-NH—, aryl-NH—C(O)—, aryl-NH—S(O)$_2$—, aryloxy, aryl-S—, aryl-S-alkyl-C(O)—, aryl-S(O)$_2$—, aryl-S(O)$_2$—NH—, arylalkyl-C(O)—, arylalkyl-C(O)—NH—, arylalkyl-NH—, arylalkyl-NH—C(O)—, arylalkyl-NH—S(O)$_2$—, arylalkoxy, arylalkyl-S—, arylalkyl-S(O)$_2$—, arylalkyl-S(O)$_2$—NH—, cycloalkyl, cycloalkyl-C(O)—, cycloalkyl-C(O)—NH—, cycloalkyl-NH—, cycloalkyl-NH—C(O)—, cycloalkyl-NH—S(O)$_2$—, cycloalkoxy, cycloalkyl-S—, cycloalkyl-S(O)$_2$—, cycloalkyl-S(O)$_2$—NH—, cycloalkenyl, cycloalkenylalkyl, cycloalkenyl-C(O)—, cycloalkenyl-C(O)—NH—, cycloalkenyl-NH—, cycloalkenyl-NH—C(O)—, cycloalkenyl-NH—S(O)$_2$—, cycloalkenyloxy, cycloalkenyl-S—, cycloalkenyl-S(O)$_2$—, cycloalkenyl-S(O)$_2$—NH—, heterocycle, heterocycle-C(O)—, heterocycle-C(O)—NH—, heterocycle-NH—, heterocycle-NH—C(O)—, heterocycle-NH—S(O)$_2$—, heterocycle-O—, heterocycle-S—, heterocycle-S(O)$_2$—, heterocycle-S(O)$_2$—NH—, heterocycle-alkyl-C(O)—, heterocycle-alkyl-C(O)—NH—, heterocycle-alkyl-NH—, heterocycle-alkyl-NH—C(O)—, heterocycle-alkyl-NH—S(O)$_2$—, heterocycle-alkyl-O—, heterocycle-alkyl-S—, heterocycle-alkyl-S(O)$_2$— and heterocycle-alkyl-S(O)$_2$—NH—;

R$_1$ is selected from the group consisting of hydrogen and alkyl;

R$_2$ is selected from the group consisting of hydrogen, halogen, alkyl and alkoxy;

R$_3$ is R$_c$R$_d$N—;

R$_4$ is selected from the group consisting of hydrogen and alkyl, or R$_4$ and R$_c$ taken together with any intervening atoms form a heterocycle;

each occurrence of R$_5$ is independently selected from the group consisting of hydrogen and alkyl;

R$_a$ is selected from the group consisting of hydrogen and alkyl;

R$_b$ is selected from the group consisting of hydrogen and alkyl, or R$_b$ and R$_1$ taken together with any intervening atoms form a heterocycle;

R$_c$ and R$_d$ are each independently selected from the group consisting of hydrogen, alkyl, aryl, arylalkyl, cycloalkyl, cycloalkenylalkyl, heterocycle, heterocycle-alkyl and hydroxyalkyl, or R$_c$ and R$_d$ taken together with any intervening atoms form a heterocycle;

Z is selected from the group consisting of hydrogen, alkyl and halogen; and m is 1, 2 or 3;

provided that:

if B is NR$_b$—, NR$_b$-alkyl or —O—, then

D is selected from the group consisting of alkyl, aryl, arylalkyl, heterocycle and heterocyclealkyl.

2. The compound according to claim 1 wherein

A is —C(O)—;

B is a bond or is selected from the group consisting of alkylene, alkenyl, —NRb- and —NR$_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, alkyl-S(O)$_2$—, aryl-C(O)—, aryl-C=N—O—, aryl-NH—, aryloxy, aryl-S—, aryl-S-alkyl-C(O)—, aryl-S(O)$_2$—, arylalkyl-C(O)—, arylalkyl-NH—, arylalkoxy, arylalkyl-S(O)$_2$—, cycloalkyl, cycloalkyl-C(O)—, cycloalkyl-NH—, cycloalkoxy, cycloalkyl-S(O)$_2$—, cycloalkenylalkyl, heterocycle-C(O)—, heterocycle-NH—, heterocycle-O—, heterocycle-S(O)$_2$—, heterocycle-alkyl-C(O)—, heterocycle-alkyl-NH—, heterocycle-alkyl-O— and heterocycle-alkyl-S(O)$_2$—;

R$_1$ is selected from the group consisting of hydrogen and alkyl;

R$_2$ is selected from the group consisting of hydrogen, halogen, alkyl and alkoxy;

R$_3$ is R$_c$R$_d$N—;

R$_4$ is selected from the group consisting of hydrogen and alkyl, or R$_4$ and R$_c$ taken together with any intervening atoms form a heterocycle;

each occurrence of R$_5$ is independently selected from the group consisting of hydrogen and alkyl;

R$_a$ is selected from the group consisting of hydrogen and alkyl;

together with any intervening atoms form a heterocycle;

R$_c$ and R$_d$ are each independently selected from the group consisting of hydrogen, alkyl, aryl, arylalkyl, cycloalkyl, cycloalkenylalkyl, heterocycle, heterocycle-alkyl and hydroxyalkyl or R$_c$ and R$_d$ taken together with any intervening atoms form a heterocycle;

Z is selected from the group consisting of hydrogen, alkyl and halogen; and m is 1, 2 or 3;

provided that:
if B is NR$_b$—, NR$_b$-alkyl or —O—, then
D is selected from the group consisting of alkyl, aryl, arylalkyl, heterocycle and heterocyclealkyl.

3. The compound according to claim 1 wherein
A is —C(O)—;
B is a bond or is selected from the group consisting of alkylene, alkenyl, —NRb- and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;
R$_1$ is selected from the group consisting of hydrogen and alkyl;
R$_2$ is selected from the group consisting of hydrogen, halogen, alkyl and alkoxy;
R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_a$ is selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ are each independently selected from the group consisting of hydrogen, alkyl, aryl, arylalkyl, cycloalkyl, cycloalkenylalkyl, heterocycle, heterocycle-alkyl and hydroxyalkyl or R$_c$ and R$_d$ taken together with any intervening atoms form a heterocycle;
Z is selected from the group consisting of hydrogen, alkyl and halogen; and
m is 1, 2 or 3;
provided that:
if B is NR$_b$—, NR$_b$-alkyl or —O—, then
D is selected from the group consisting of alkyl, aryl, arylalkyl, heterocycle and heterocyclealkyl.

4. The compound according to claim 1 wherein
A is —C(O)—;
B is a bond or is selected from the group consisting of alkylene, alkenyl, —NRb- and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;
R$_1$ is selected from the group consisting of hydrogen and alkyl;
R$_2$ is selected from the group consisting of hydrogen, halogen, alkyl and alkoxy;
R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_a$ is selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ are each independently selected from the group consisting of hydrogen, alkyl, aryl, arylalkyl, cycloalkyl, cycloalkenylalkyl, heterocycle, heterocycle-alkyl and hydroxyalkyl;
Z is selected from the group consisting of hydrogen, alkyl and halogen; and
m is 1, 2 or 3;
provided that:
if B is NR$_b$—, NR$_b$-alkyl or —O—, then
D is selected from the group consisting of alkyl, aryl, arylalkyl, heterocycle and heterocyclealkyl.

5. The compound according to claim 4, wherein the compound is selected from the group consisting of 2-[4-(benzyloxy)phenyl]-N-{2-[2-(dimethylamino)ethyl]-2H-indazol-4-yl}acetamide;
N-{2-[2-(dimethylamino)ethyl]-2H-indazol-5-yl}-N'-(4-phenoxyphenyl)urea;
N-{2-[2-(dimethylamino)ethyl]-2H-indazol-5-yl}-2-(4-phenoxyphenyl)acetamide;
(2E)-3-[4-(benzyloxy)phenyl]-N-{2-[2-(dimethylamino)ethyl]-2H-indazol-5-yl}acrylamide;
(2E)-3-(1,1'-biphenyl-4-yl)-N-{2-[2-(dimethylamino)ethyl]-2H-indazol-5-yl}acrylamide;
4-benzyl-N-{2-[2-(dimethylamino)ethyl]-2H-indazol-5-yl}benzamide;
N-{2-[2-(dimethylamino)ethyl]-2H-indazol-5-yl}-3-phenoxybenzamide;
4-(4-chlorophenyl)-N-{2-[2-(dimethylamino)ethyl]-2H-indazol-5-yl}cyclohexanecarboxamide;
N-{2-[2-(dimethylamino)ethyl]-2H-indazol-5-yl}-2-(3-phenoxyphenyl)acetamide;
N-(2-{2-[isobutyl(methyl)amino]ethyl}-2H-indazol-5-yl)-N'-(4-phenoxyphenyl)urea;
N-(2-{2-[isopropyl(methyl)amino]ethyl}-2H-indazol-5-yl)-N'-(4-phenoxyphenyl)urea;
N-{2-[2-(cyclohexylamino)ethyl]-2H-indazol-5-yl}-N'-(4-phenoxyphenyl)urea;
N-{2-[2-(cyclopentylamino)ethyl]-2H-indazol-5-yl}-N'-(4-phenoxyphenyl)urea;
N-(2-{2-[cyclohexyl(methyl)amino]ethyl}-2H-indazol-5-yl)-N'-(4-phenoxyphenyl)urea;
2-[4-(benzyloxy)phenyl]-N-{2-[2-(dimethylamino)ethyl]-2H-indazol-6-yl}acetamide;
N-{2-[2-(dimethylamino)ethyl]-2H-indazol-6-yl}-2-(3-phenoxyphenyl)acetamide;
N-{2-[2-(dimethylamino)ethyl]-2H-indazol-6-yl}-3-phenoxybenzamide;
4-(1,1'-biphenyl-4-yl)-N-{2-[2-(dimethylamino)ethyl]-2H-indazol-6-yl}-4-oxobutanamide;
2-(1,1'-biphenyl-4-yl)-N-{2-[2-(dimethylamino)ethyl]-2H-indazol-6-yl}acetamide;
N-{2-[2-(dimethylamino)ethyl]-2H-indazol-6-yl}-4-oxo-4-(4-phenoxyphenyl)butanamide;
4-(4-chlorophenyl)-N-{2-[2-(dimethylamino)ethyl]-2H-indazol-6-yl}cyclohexanecarboxamide;
4-benzyl-N-{2-[2-(dimethylamino)ethyl]-2H-indazol-6-yl}benzamide;

N-{2-[2-(dimethylamino)ethyl]-2H-indazol-6-yl}-2-(4-phenoxyphenyl)acetamide;
N-{2-[2-(dimethylamino)ethyl]-2H-indazol-6-yl}-N'-(4-phenoxyphenyl)urea;
N-{2-[2-(cyclopentylamino)ethyl]-2H-indazol-6-yl}-N'-(4-phenoxyphenyl)urea;
N-(4-phenoxyphenyl)-N'-(2-{2-[(tetrahydrofuran-2-ylmethyl)amino]ethyl}-2H-indazol-6-yl)urea;
N-(2-{2-[(2-morpholin-4-ylethyl)amino]ethyl}-2H-indazol-6-yl)-N'-(4-phenoxyphenyl)urea;
N-{2-[2-(methylamino)ethyl]-2H-indazol-6-yl}-N-(4-phenoxyphenyl)urea;
N-{2-[3-(cyclopentylamino)propyl]-2H-indazol-6-yl}-N'-(4-phenoxyphenyl)urea;
N-{2-[3-(cyclohexylamino)propyl]-2H-indazol-6-yl}-N'-(4-phenoxyphenyl)urea;
N-{2-[3-(diisopropylamino)propyl]-2H-indazol-6-yl}-N'-(4-phenoxyphenyl)urea; and
N-(2-{3-[benzyl(2-hydroxyethyl)amino]propyl}-2H-indazol-6-yl)-N'-(4-phenoxyphenyl)urea.

6. The compound according to claim 1 wherein
A is —C(O)—;
B is a bond or is selected from the group consisting of alkylene, alkenyl, —NRb- and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;
$R_1$ is selected from the group consisting of hydrogen and alkyl;
$R_2$ is selected from the group consisting of hydrogen, halogen, alkyl and alkoxy;
$R_3$ is $R_cR_dN$—;
$R_4$ is selected from the group consisting of hydrogen and alkyl, or $R_4$ and $R_c$ taken together with any intervening atoms form a heterocycle;
each occurrence of $R_5$ is independently selected from the group consisting of hydrogen and alkyl;
$R_a$ is selected from the group consisting of hydrogen and alkyl;
$R_b$ is selected from the group consisting of hydrogen and alkyl, or $R_b$ and $R_1$ taken together with any intervening atoms form a heterocycle;
$R_c$ and $R_d$ taken together with the atoms to which they are attached form a 4 membered heterocycle;
Z is selected from the group consisting of hydrogen, alkyl and halogen; and
m is 1, 2 or 3;
provided that:
if B is $NR_b$—, $NR_b$-alkyl or —O—, then
D is selected from the group consisting of alkyl, aryl, arylalkyl, heterocycle and heterocyclealkyl.

7. The compound according to claim 1 that is N-[2-(2-azetidin-1-ylethyl)-2H-indazol-5-yl]-N'-(4-phenoxyphenyl)urea.

8. The compound according to claim 1 wherein
A is —C(O)—;
B is a bond or is selected from the group consisting of alkylene, alkenyl, —NRb- and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;
$R_1$ is selected from the group consisting of hydrogen and alkyl;
$R_2$ is selected from the group consisting of hydrogen, halogen, alkyl and alkoxy;
$R_3$ is $R_cR_dN$—;
$R_4$ is selected from the group consisting of hydrogen and alkyl, or $R_4$ and $R_c$ taken together with any intervening atoms form a heterocycle;
each occurrence of $R_5$ is independently selected from the group consisting of hydrogen and alkyl;
$R_a$ is selected from the group consisting of hydrogen and alkyl;
$R_b$ is selected from the group consisting of hydrogen and alkyl, or $R_b$ and $R_1$ taken together with any intervening atoms form a heterocycle;
$R_c$ and $R_d$ taken together with the atoms to which they are attached form a 5 membered heterocycle;
Z is selected from the group consisting of hydrogen, alkyl and halogen; and
m is 1, 2 or 3;
provided that:
if B is $NR_b$—, $NR_b$-alkyl or —O—, then
D is selected from the group consisting of alkyl, aryl, arylalkyl, heterocycle and heterocyclealkyl.

9. The compound according to claim 1 wherein
A is —C(O)—;
B is a bond or is selected from the group consisting of alkylene, alkenyl, —NR$_b$— and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;
$R_1$ is selected from the group consisting of hydrogen and alkyl;
$R_2$ is selected from the group consisting of hydrogen, halogen, alkyl and alkoxy;
$R_3$ is $R_cR_dN$—;
$R_4$ is selected from the group consisting of hydrogen and alkyl, or $R_4$ and $R_c$ taken together with any intervening atoms form a heterocycle;
each occurrence of $R_5$ is independently selected from the group consisting of hydrogen and alkyl;
$R_a$ is selected from the group consisting of hydrogen and alkyl;
$R_b$ is selected from the group consisting of hydrogen and alkyl, or $R_b$ and $R_1$ taken together with any intervening atoms form a heterocycle;
$R_c$ and $R_d$ taken together with the atoms to which they are attached form

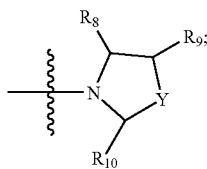

Y is selected from the group consisting of —O—, —NRj-, —CHRj- and —C(O)—;

Z is selected from the group consisting of hydrogen, alkyl and halogen;

$R_8$ is selected from the group consisting of hydrogen and alkyl;

$R_9$ and $R_{10}$ are each individually selected from the group consisting of oxo, hydrogen and alkyl; and m is 1, 2 or 3;

provided that:

if B is $NR_b$—, $NR_b$-alkyl or —O—, then

D is selected from the group consisting of alkyl, aryl, arylalkyl, heterocycle and heterocyclealkyl.

10. The compound according to claim 9 wherein the compound is selected from the group consisting of 2-[4-(benzyloxy)phenyl]-N-[2-(2-pyrrolidin-1-ylethyl)-2H-indazol-4-yl]acetamide;

4-oxo-4-(4-phenoxyphenyl)-N-[2-(2-pyrrolidin-1-yl-ethyl)-2H-indazol-4-yl]butanamide;

4-(1,1'-biphenyl-4-yl)-4-oxo-N-[2-(2-pyrrolidin-1-yl-ethyl)-2H-indazol-4-yl]butanamide;

2-(3-phenoxyphenyl)-N-[2-(2-pyrrolidin-1-ylethyl)-2H-indazol-4-yl]acetamide;

2-(4-phenoxyphenyl)-N-[2-(2-pyrrolidin-1-ylethyl)-2H-indazol-4-yl]acetamide;

N-(4-phenoxyphenyl)-N'-[2-(2-pyrrolidin-1-ylethyl)-2H-indazol-5-yl]urea;

N-(4-bromophenyl)-N'-[2-(2-pyrrolidin-1-ylethyl)-2H-indazol-5-yl]urea;

N-(4'-fluoro-1,1'-biphenyl-4-yl)-N-[2-(2-pyrrolidin-1-yl-ethyl)-2H-indazol-5-yl]urea;

2-(4-phenoxyphenyl)-N-[2-(2-pyrrolidin-1-ylethyl)-2H-indazol-5-yl]acetamide;

N-{2-[2-(2-methylpyrrolidin-1-yl)ethyl]-2H-indazol-5-yl}-N'-(4-phenoxyphenyl)urea;

N-(2-{2-[(2S)-2-(methoxymethyl)pyrrolidin-1-yl]ethyl}-2H-indazol-5-yl)-N'-(4-phenoxyphenyl)urea;

N-{2-[2-(3-hydroxypyrrolidin-1-yl)ethyl]-2H-indazol-5-yl}-N-(4-phenoxyphenyl)urea;

N-((2S)-1-{2-[5-({[(4-phenoxyphenyl)amino]carbonyl}amino)-2H-indazol-2-yl]ethyl}pyrrolidin-2-yl)acetamide;

N-(2-{2-[(2S)-2-(hydroxymethyl)pyrrolidin-1-yl]ethyl}-2H-indazol-5-yl)-N'-(4-phenoxyphenyl)urea;

2-[4-(benzyloxy)phenyl]-N-[2-(2-pyrrolidin-1-ylethyl)-2H-indazol-6-yl]acetamide;

N-{2-[2-(2-methylpyrrolidin-1-yl)ethyl]-2H-indazol-6-yl}-N'-(4-phenoxyphenyl)urea;

N-{2-[2-(2,5-dimethylpyrrolidin-1-yl)ethyl]-2H-indazol-6-yl}-N'-(4-phenoxyphenyl)urea;

N-(4-phenoxyphenyl)-N'-[2-(3-pyrrolidin-1-ylpropyl)-2H-indazol-6-yl]urea;

N-(2-{3-[(2S)-2-(methoxymethyl)pyrrolidin-1-yl]propyl}-2H-indazol-6-yl)-N'-(4-phenoxyphenyl)urea;

N-(2-{3-[(2S)-2-(hydroxymethyl)pyrrolidin-1-yl]propyl}-2H-indazol-6-yl)-N-(4-phenoxyphenyl)urea;

N-{2-[3-(3-hydroxypyrrolidin-1-yl)propyl]-2H-indazol-6-yl}-N'-(4-phenoxyphenyl)urea;

N-(1-{3-[6-({[(4-phenoxyphenyl)amino]carbonyl}amino)-2H-indazol-2-yl]propyl}pyrrolidin-3-yl)acetamide;

N-{2-[3-(2-methylpyrrolidin-1-yl)propyl]-2H-indazol-6-yl}-N'-(4-phenoxyphenyl)urea;

1-(4-phenoxyphenyl)-3-[2-(2-pyrrolidin-1-ylethyl)-2H-indazol-5-yl]-1,3-dihydro-2H-imidazol-2-one; and 1-(4-phenoxyphenyl)-3-[2-(2-pyrrolidin-1-ylethyl)-2H-indazol-5-yl]imidazolidin-2-one.

11. The compound according to claim 1 wherein

A is —C(O)—;

B is a bond or is selected from the group consisting of alkylene, alkenyl, —$NR_b$— and —$NR_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;

$R_1$ is selected from the group consisting of hydrogen and alkyl;

$R_2$ is selected from the group consisting of hydrogen, halogen, alkyl and alkoxy;

$R_3$ is $R_cR_dN$—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_a$ is selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ taken together with the atoms to which they are attached form a 6 membered heterocycle;

Z is selected from the group consisting of hydrogen, alkyl and halogen; and m is 1, 2 or 3;

provided that:

if B is $NR_b$—, $NR_b$-alkyl or —O—, then

D is selected from the group consisting of alkyl, aryl, arylalkyl, heterocycle and heterocyclealkyl.

12. The compound according to claim 1 wherein

A is —C(O)—;

B is a bond or is selected from the group consisting of alkylene, alkenyl, —$NR_b$— and —$NR_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;

$R_1$ is selected from the group consisting of hydrogen and alkyl;

$R_2$ is selected from the group consisting of hydrogen, halogen, alkyl and alkoxy;

R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_a$ is selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ taken together with the atoms to which they are attached form

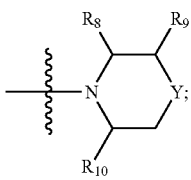

Y is selected from the group consisting of —O—, —NRj-, —CHRj- and —C(O)—;
Z is selected from the group consisting of hydrogen, alkyl and halogen;
R$_8$ is selected from the group consisting of hydrogen and alkyl;
R$_9$ and R$_{10}$ are each individually selected from the group consisting of oxo, hydrogen and alkyl; and
m is 1, 2 or 3;
provided that:
if B is NR$_b$—, NR$_b$-alkyl or —O—, then
D is selected from the group consisting of alkyl, aryl, arylalkyl, heterocycle and heterocyclealkyl.

13. The compound according to claim 12, wherein the compound is selected from the group consisting of 2-[4-(benzyloxy)phenyl]-N-[2-(2-piperidin-1-ylethyl)-2H-indazol-4-yl]acetamide;
2-(3-phenoxyphenyl)-N-[2-(2-piperidin-1-ylethyl)-2H-indazol-4-yl]acetamide;
4-(1,1'-biphenyl-4-yl)-4-oxo-N-[2-(2-piperidin-1-ylethyl)-2H-indazol-4-yl]butanamide;
2-(4-phenoxyphenyl)-N-[2-(2-piperidin-1-ylethyl)-2H-indazol-5-yl]acetamide;
N-(4-phenoxyphenyl)-N'-[2-(2-piperidin-1-ylethyl)-2H-indazol-5-yl]urea;
N-{2-[2-(4-methylpiperidin-1-yl)ethyl]-2H-indazol-5-yl}-N'-(4-phenoxyphenyl)urea;
N-{2-[2-(3-methylpiperidin-1-yl)ethyl]-2H-indazol-5-yl}-N'-(4-phenoxyphenyl)urea;
1-{2-[5-({[(4-phenoxyphenyl)amino]carbonyl}amino)-2H-indazol-2-yl]ethyl}piperidine-4-carboxamide;
N-(2-{2-[(3R)-3-hydroxypiperidin-1-yl]ethyl}-2H-indazol-5-yl)-N'-(4-phenoxyphenyl)urea;
N-{2-[2-(2-methylpiperidin-1-yl)ethyl]-2H-indazol-5-yl}-N'-(4-phenoxyphenyl)urea;
1-{2-[5-({[(4-phenoxyphenyl)amino]carbonyl}amino)-2H-indazol-2-yl]ethyl}piperidine-3-carboxamide;
N-{2-[2-(3,3-difluoropiperidin-1-yl)ethyl]-2H-indazol-5-yl}-N'-(4-phenoxyphenyl)urea;
N-{2-[2-(4-hydroxypiperidin-1-yl)ethyl]-2H-indazol-5-yl}-N'-(4-phenoxyphenyl)urea;
N-{2-[2-(1,4-dioxa-8-azaspiro[4.5]dec-8-yl)ethyl]-2H-indazol-5-yl}-N'-(4-phenoxyphenyl)urea;
N-{2-[2-(2,6-dimethylmorpholin-4-yl)ethyl]-2H-indazol-5-yl}-N'-(4-phenoxyphenyl)urea;
N-{2-[2-(2,6-dimethylmorpholin-4-yl)ethyl]-2H-indazol-5-yl}-N'-(4-phenoxyphenyl)urea;
N-{2-[2-(4-methylpiperidin-1-yl)ethyl]-2H-indazol-6-yl}-N'-(4-phenoxyphenyl)urea;
N-{2-[2-(3-methylpiperidin-1-yl)ethyl]-2H-indazol-6-yl}-N'-(4-phenoxyphenyl)urea;
N-{2-[2-(2-methylpiperidin-1-yl)ethyl]-2H-indazol-6-yl}-N'-(4-phenoxyphenyl)urea;
N-(2-{3-[3-(hydroxymethyl)piperidin-1-yl]propyl}-2H-indazol-6-yl)-N-(4-phenoxyphenyl)urea;
N-(2-{3-[2-(2-hydroxyethyl)piperidin-1-yl]propyl}-2H-indazol-6-yl)-N'-(4-phenoxyphenyl)urea;
N-{2-[3-(4-hydroxypiperidin-1-yl)propyl]-2H-indazol-6-yl}-N'-(4-phenoxyphenyl)urea;
N-(4-phenoxyphenyl)-N'-[2-(3-piperidin-1-ylpropyl)-2H-indazol-6-yl]urea;
N-[2-(3-morpholin-4-ylpropyl)-2H-indazol-6-yl]-N-(4-phenoxyphenyl)urea;
N-{2-[3-(2-methylpiperidin-1-yl)propyl]-2H-indazol-6-yl}-N'-(4-phenoxyphenyl)urea; and
N-{2-[3-(2-ethylpiperidin-1-yl)propyl]-2H-indazol-6-yl}-N'-(4-phenoxyphenyl)urea.

14. The compound according to claim 1 wherein
A is —C(O)—;
B is a bond or is selected from the group consisting of alkylene, alkenyl, —NR$_b$— and —NR$_b$alkyl;
D is a bond or is selected from the group consisting of alkylene, aryl, arylalkyl, heterocycle and heterocyclealkyl;
E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;
R$_1$ is selected from the group consisting of hydrogen and alkyl;
R$_2$ is selected from the group consisting of hydrogen, halogen, alkyl and alkoxy;
R$_3$ is R$_c$R$_d$N—;
R$_4$ is selected from the group consisting of hydrogen and alkyl, or R$_4$ and R$_c$ taken together with any intervening atoms form a heterocycle;
each occurrence of R$_5$ is independently selected from the group consisting of hydrogen and alkyl;
R$_a$ is selected from the group consisting of hydrogen and alkyl;
R$_b$ is selected from the group consisting of hydrogen and alkyl, or R$_b$ and R$_1$ taken together with any intervening atoms form a heterocycle;
R$_c$ and R$_d$ taken together with the atoms to which they are attached form a 7 membered heterocycle;
Z is selected from the group consisting of hydrogen, alkyl and halogen; and
m is 1, 2 or 3;
provided that:
if B is NR$_b$—, NR$_b$-alkyl or —O—, then
D is selected from the group consisting of alkyl, aryl, arylalkyl, heterocycle and heterocyclealkyl.

15. The compound according to claim 1 wherein
A is —C(O)—;
B is a bond or is selected from the group consisting of alkylene, alkenyl, —NR$_b$— and —NR$_b$alkyl;

D is a bond or is selected from the group consisting of alkylene, aryl, arylalkyl, heterocycle and heterocyclealkyl;

E is selected from the group consisting of alkyl, alkyl-C(O)—, alkyl-NH—, alkoxy, aryl-C(O)—, aryl-C=N—O—, aryl-NH—, aryloxy, aryl-S—, aryl-S-alkyl-C(O)—, arylalkyl-C(O)—, arylalkyl-NH—, arylalkoxy, cycloalkyl, cycloalkenylalkyl, heterocycle-C(O)—, heterocycle-NH—, heterocycle-O—, heterocycle-alkyl-NH— and heterocycle-alkyl-O—;

$R_1$ is selected from the group consisting of hydrogen and alkyl;

$R_2$ is selected from the group consisting of hydrogen, halogen, alkyl and alkoxy;

$R_3$ is $R_c R_d N$—;

$R_4$ is selected from the group consisting of hydrogen and alkyl, or $R_4$ and $R_c$ taken together with any intervening atoms form a heterocycle;

each occurrence of $R_5$ is independently selected from the group consisting of hydrogen and alkyl;

$R_a$ is selected from the group consisting of hydrogen and alkyl;

$R_b$ is selected from the group consisting of hydrogen and alkyl, or $R_b$ and $R_1$ taken together with any intervening atoms form a heterocycle;

$R_c$ and $R_d$ taken together with the atoms to which they are attached form

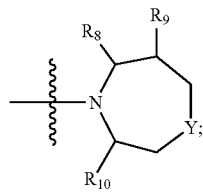

Y is selected from the group consisting of —O—, —NRj-, —CHRj- and —C(O)—;

Z is selected from the group consisting of hydrogen, alkyl and halogen;

$R_8$ is selected from the group consisting of hydrogen and alkyl;

$R_9$ and $R_{10}$ are each individually selected from the group consisting of oxo, hydrogen and alkyl; and m is 1, 2 or 3;

provided that:

if B is $NR_b$—, $NR_b$-alkyl or —O—, then

D is selected from the group consisting of alkyl, aryl, arylalkyl, heterocycle and heterocyclealkyl.

16. The compound according to claims 15, that is

N-[2-(2-azepan-1-ylethyl)-2H-indazol-5-yl]-N'-(4-phenoxyphenyl)urea.

17. A pharmaceutical composition comprising a therapeutically effective amount of a compound of formula (I) in combination with a pharmaceutically suitable carrier.

18. A method of treating obesity by inhibiting the effects of melanin concentrating hormone (MCH) through the melanin concentrating hormone receptor, comprising administering a therapeutically effective amount of a compound of formula (I).

19. A method of treating abnormalities in reproduction and sexual behavior, thyroid hormone secretion, diuresis and water/electrolyte homeostasis, sensory processing, memory, sleeping and arousal, anxiety and depression, and seizure by inhibiting the effects of melanin concentrating hormone (MCH) through the melanin concentrating hormone receptor, comprising administering a therapeutically effective amount of a compound of formula (I).

\* \* \* \* \*